US006025333A

United States Patent [19]
Schwab et al.

[11] Patent Number: 6,025,333
[45] Date of Patent: Feb. 15, 2000

[54] TREATMENT OF CNS TUMORS WITH METALLOPROTEASE INHIBITORS

[75] Inventors: Martin E. Schwab; Pierenrico W. Caroni, both of Zurich; Paolo A. Paganetti, Birmensdorferstr., all of Switzerland

[73] Assignee: Erziehungsdirektion of the Canton Zurich, Zurich, Switzerland

[21] Appl. No.: 08/462,312

[22] Filed: Jun. 5, 1995

Related U.S. Application Data

[60] Division of application No. 07/401,212, Aug. 30, 1989, which is a continuation-in-part of application No. 07/267,941, Nov. 4, 1988, abandoned.

[51] Int. Cl.⁷ ......................... A61K 38/06; A61K 38/05; A61K 38/55
[52] U.S. Cl. .............................. 514/18; 514/19; 514/292; 424/DIG. 6; 424/94.67
[58] Field of Search .................................. 514/2, 18, 19, 514/292, 566, 738; 424/DIG. 6, 94.67

[56] References Cited

U.S. PATENT DOCUMENTS

| | | | |
|---|---|---|---|
| 4,230,691 | 10/1980 | Young | 424/85 |
| 4,287,184 | 9/1981 | Young | 424/177 |
| 4,407,744 | 10/1983 | Young | 260/112 R |
| 4,444,760 | 4/1984 | Thomas, Jr. | 424/177 |
| 4,803,163 | 2/1989 | Fahey et al. | 435/68 |
| 4,923,696 | 5/1990 | Appel et al. | 424/548 |
| 5,250,414 | 10/1993 | Schwab et al. | 435/7.72 |

FOREIGN PATENT DOCUMENTS

| | | |
|---|---|---|
| 046 523A1 | 3/1982 | European Pat. Off. . |
| 155 433 | 9/1985 | European Pat. Off. . |
| 159 289 | 10/1985 | European Pat. Off. . |
| 233 838 | 8/1987 | European Pat. Off. . |
| WO 90/05191 | 5/1990 | WIPO . |

OTHER PUBLICATIONS

Aguayo et al., 1978, Ensheathment and myelination of regenerating PNS fibres by transplanted optic nerve glia, Neurosci. Lett. 9:97–104.

Westall et al., 1978, Brain–derived fibroblast growth factor: Identity with a fragment of the basic protein of myelin, Proc. Natl. Acad. Sci. USA 75:4675–78.

Boggust et al., 1979, Inhibition of collagen peptidase in HeLa cells and human tumors by compounds including drugs used in cancer therapy, Chem. Abst. 90:66525q.

Bjorklund and Stenevi, 1979, Regeneration of monoaminergic and cholinergic neurons in the mammalian central nervous system, Physiolog. Rev. 59:62–100.

Weinberg and Spencer, 1979, Studies on the control of myelinogenesis. 3. Signalling of oligodendrocyte myelination by regenerating peripheral axons, Brain Res. 162:273–79.

Sonnenfeld and Ishii, 1982, Nerve growth factor effects and receptors in cultured human neuroblastoma cell lines, J. Neurosci. Res. 8:375–91.

Kato et al., 1982, Inhibition of growth of mouse neuroblastoma cells by protein factor derived from rat glioblasts, Dev. Brain Res. 3:645–51.

Thoenen et al., 1982, Factors involved in the regulation of the survival and differentiation of neurons, in Repair and Regeneration of the Nervous System (Nicholls, ed.; Springer–Verlag), pp. 173–185.

McConnell and Berry, 1982, Regeneration of ganglion cell axons in the adult mouse retina, Brain Res. 241:362–65.

Benfey and Aguayo, 1982, Extensive elongation of axons from rat brain into peripheral nerve grafts, Nature 296:150–52.

Schwartz and Spirman, 1982, Sprouting from chicken embryo dorsal root ganglia induced by nerve growth factor is specifically inhibited by affinity–purified antiganglioside antibodies, Proc. Natl. Acad. Sci. USA 79:6080–83.

Coleman et al., 1982, Synthesis and incorporation of myelin polypeptides into CNS myelin, J. Cell Biol. 95:598–608.

Sakazaki et al., 1983, Characterization and partial purification of neuroblastoma growth inhibitory factor from the culture medium of glioblasts, Brain Res. 262:125–35.

Turner et al., 1983, Extract from brain stimulates neurite outgrowth from fetal rat retinal explants, Dev. Brain Res. 6:77–83.

Nornes et al., 1983, Reinnervation of the denervated adult spinal cord of rats by intraspinal transplants of embryonic brain stem neurons, Cell Tissue Res. 230:15–35.

Sanes, 1983, Roles of extracellular matrix in neural development, Ann. Rev. Physiol. 45:581–600.

Cornbrooks et al., 1983, In vivo and in vitro observations on laminin production by Schwann cells, Proc. Natl. Acad. Sci. USA 80:3850–54.

Richardson et al., 1984, Regeneration of long spinal axons in the rat, J. Neurocytol. 13:165–82.

Edelman, 1984, Expression of cell adhesion molecules during embryogenesis and regeneration, Exp. Cell Res. 161:1–16.

Commissiong, 1984, Fetal locus coeruleus transplanted into the transected spinal cord of the adult rat some observations and implications, Neurosic. 12:839–53.

(List continued on next page.)

*Primary Examiner*—Marianne P. Allen
*Assistant Examiner*—Robert C. Hayes
*Attorney, Agent, or Firm*—Pennie & Edmonds LLP

[57] ABSTRACT

The present invention relates to genes and their encoded proteins which regulate neurite growth and the diagnostic and therapeutic use of such proteins (termed herein neurite growth regulatory factors). The proteins of the present invention include central nervous system myelin associated proteins and metalloproteases associated with glioblastoma cells and other malignant tumors which can metastasize to the brain. The metalloproteases of the invention have value in the treatment of nerve damage and of degenerative disorders of the nervous system. The present invention is also directed to inhibitors of the metalloproteases. Such inhibitors in combination with the CNS myelin associated inhibitory proteins can be used in the treatment of malignant tumors.

10 Claims, 32 Drawing Sheets

OTHER PUBLICATIONS

Carlson et al., 1984, Synaptic vesicles and the synaptic extracellular matrix contain an identical proteo–glycan–like antigen, J. Cell Biochem. 8 Part B:293.

Schwab and Thoenen, 1984, Factors influencing axonal growth: central vs. peripheral nerve explants as substrates in vitro, in Experimental Brain Research, Suppl. 13: Process of Recovery From Neural Trauma, International Symposium, Israel, Jun. 1984 (Gilad et al., eds.; Springer–Verlag, pp. 205–214.

Schwab et al., 1984, Growth factors and substrate pathways for peripheral nerve cells,—an overview, Neurosci. Lett., Suppl. 18:S423.

Schwab, 1985, Interaction of neurons with nerve explants and dissociated glial cells in culture, Neurosci. Lett., Suppl. 22:S365.

Guenther et al., 1985, A glia–derived neurite–promoting factor with protease inhibitory activity, Chem. Abst. 103:270640z.

Tobey et al., 1985, Neurite extension by neuroblastoma cells on substratum–bound fibronectin's cell binding fragment but not on the heparin sulfate–binding protein, platelet factor–4, Exp. Cell Res. 158:395–412.

So and Aguayo, 1985, Lengthy regrowth of cuts axons from ganglion cells after peripheral nerve transplantation into the retina of adult rats, Brain Res. 328:349–54.

Liesi, 1985, Do neurons in the vertebrate CNS migrate on laminin? EMBO 4:1163–70.

Liesi, 1985, Laminin–immunoreactive glia distinguish regeneration adult CNS systems from non–regenerative ones, EMBO 4:2505–11.

Caroni et al., 1985, Presynaptic neurones may contribute a unique glycoprotein to the extracellular matrix at the synapse, Nature 314:441–43.

Stallcup et al., 1985, Antibody against nerve growth factor–inducible large external (NILE) glycoprotein labels nerve fiber tracts in the developing rat nervous system, J. Neurosci. 5:1090–1101.

Schwab and Thoenen, 1985, Dissociated neurons regenerate into sciatic but not optic nerve explants in culture irrespective of neurotrophic factors, J. Neurosci. 5:2415–23.

Linder et al., 1986, Experimental modification of postnatal cerebellar granule cell migration in vitro, Brain Res. 377:298–304.

Fischer et al., 1986, Neurite outgrowth patterns in cerebellar microexplant cultures are affected by antibodies to the cell surface glycoprotein L1, J. Neurosci. 6:605–12.

Mirsky et al., 1986, Distribution of the adhesion molecules N–CAM and L1 on peripheral neurons and glia in adult rats, J. Neurocytol. 15:799–815.

Schwab, 1986, A subtype of oligodendroglial cells represents a non–permissive substrate for neuronal attachment and fiber growth, Experientia 42:632.

Daniloff et al., 1986, Altered expression of neuronal cell adhesion molecules induced by nerve injury and repair, J. Cell Biol. 103:929–45.

Schwab and Caroni, 1986, Rat CNS myelin and a subtype of oligodendrocytes in culture represent a non–permissive substrate for neurite outgrowth, Neurosci. Lett. Suppl., (0)26:S19.

Chiu et al., 1986, A monoclonal antibody that blocks the activity of a neurite regeneration–promoting factor: studies on the binding site and its localization in vivo, J. Cell Biol. 103:1383–98.

Johnson et al., 1986, Brain–derived neurotrophic factor supports the survival of cultured rat retinal ganglion cells, J. Neurosci. 6:3031–38.

Chiquet–Ehrismann et al., 1986, Tenascin: an extracellular matrix protein involved in tissue interactions during fetal development and oncogenesis, Cell 47:131–39.

Schwab, 1986, Rat CNS myelin and a subtype of oligodendrocytes in culture represent a non–permissive substrate for neurite growth and fibroblast spreading, Soc. Neurosci. Abstr. 12:12.

Johnson et al., 1986, Expression and structure of the human NGF receptor, Cell 47:545–54.

Caroni et al., 1986, A cell surface molecule that inhibits neurite outgrowth and cell locomotion, J. Cell Biol. 103 (5 Part 2):407a.

Caputo et al., 1987, Proteoglycan degradation by a chondrocyte metalloprotease. Effects of synthetic protease inhibitors, Biochem. Pharmacol. 36:995–1002.

Schwartz, 1987, Molecular and cellular aspects of nerve regeneration, CRC Crit. Rev. Biochem. 22:89–110.

Bregman, 1987, Spinal cord transplants permit the growth of serotonergic axons across the site of neonatal spinal cord transection, Dev. Brain Res. 34:265–79.

Carbonetto et al., 1987, Nerve fiber growth in culture on tissue substrata from central and peripheral nervous systems, J. Neurosci. 7:610–20.

Caroni and Schwab, 1987, Two membrane proteins of myelin and oligodendrocytes inhibit neurite outgrowth and fibroblast migration, Experientia 43:654.

Schwab et al., 1987, Oligodendrocytes and myelin as non–permissive substrates for neurite regeneration, J. Neurochem. 48(Suppl.):S17.

Caroni and Schwab, 1987, Protins of rat CNS white matter and of myelin forming oligodendrocytes are potent inhibitors of neurite outgrowth and of cell locomotion, Soc. Neurosci. Abstr. 13:1040.

Caroni et al., 1988, Central nervous system regeneration: oligodendrocytes and myelin as non–permissive substrates for neurite growth, in Progress in Brain Research, vol. 78 (Gash et al, eds.; Elsevier), pp. 363–70.

Caroni et al., 1988, Two membrane protein fractions from rat central myelin with inhibitory properties for neurite growth and fibroblast spreading, J. Cell Biol. 106:1281–88.

Caroni et al., 1988, Antibody against myelin–associated inhibitor of neurite growth neutralizes nonpermissive substrate properties of CNS white matter, Neuron 1:85–96 ([Conference, Mar. of ] 1988).

Savio and Schwab, 1988, CNS white matter is a non–permissive substrate for neuron adhesion and neurite growth, Experientia 44 (Abstr.):A27.

Savio and Schwab, 1988, Rat CNS white matter is a non–permissive substrate for neuronal cell adhesion and neurite growth, Neurosci. Lett., Suppl. 33:S172.

Savio and Schwab, 1988, CNS white matter, but not gray matter, is a non–permissive substrate for neuron adhesion and neurite growth, Eur. J. Neurosci., Suppl. 1:207.

Caroni and Schwab, 1988, Oligodendrocytes and CNS myelin contain inhibitory substrates for neurite growth, Experientia 44(Abstr.):A28.

Schwab et al., 1988, Oligodendrocytes and myelin inhibit growth of neurites in the mammalian CNS, Psychopharmacol. 96 (Suppl.):15.

Caroni et al., 1988, Potent membrane–bound inhibitors of neurite growth on the surface of cultured oligodendrocytes and in CNS white matter, Europ. J. Neurosci., Suppl. 1:103.

Schwab and Caroni, 1988, Oligodendrocytes and CNS myelin are nonpermissive substrates for neurite growth and fibroblast spreading in vitro, J. Neurosci. 8:2381–93.

Dutly and Schwab, 1988, How is oligodendrocyte differentiation and myelin formation regulated? Schweizer Archiv. Neurol. Psych. 140:19–21.

Bastmeyer et al., 1988, Rat CNS–myelin and oligodendrocytes impair the growth of goldfish retinal axons in vitro, Soc. Neurosci. Abstr. 14:452.

Bastmeyer et al., 1988, Encounter of goldfish retinal axons with rat CNS–myelin and oligodendrocytes, Eur. J. Neurosci., Suppl. 1:207.

Vanselow et al., 1988, Interactions between fibers from chick embryonic retinal explants and central glial cells from the postnatal rat optic nerve, Eur. J. Neurosci., Suppl. 1:240.

Schwab and Savio, 1988, Regional appearance of myelin constituents in the developing rat spinal cord, Soc. Neurosci. Abstr. 14:1200.

Caroni et al., 1988, Cell surface inhibitors of neurite growth on differentiated oligodendrocytes: appearance after nerve fiber growth and before myelination, Soc. Neurosci. Abstr. 14:497.

Paganetti et al., 1988, Glioblastoma infiltration into central nervous system tissue in vitro: involvement of metalloprotease, J. Cell Biol. 107:2281–91.

Schwab, 1988, Inhibitors of nerve fiber growth in the central nervous system, A.A.A.S. Publ. (88–30):63.

Schwab and Schnell, 1989, Region–specific appearance of myelin constituents in the developing rat spinal cord, J. Neurocytol. 18:161–69.

Schwab et al., 1989, Symposium. Inhibitory influences on growth cones and cells, Soc. Neurosci. Abstr. 15:1106.

Schwab et al., 1989, Myelin–associated inhibitors of nerve fiber growth, J. Neuro–Oncology 7(Suppl.):S26.

Hammerschlag et al., 1989, Metalloendoprotease inhibitors block fast axonal transport, J. Neurochem. 52:268–73.

Caroni and Schwab, 1989, Codistribution of neurite growth inhibitors and oligodendrocytes in rat CNS: appearance follows nerve fiber growth and precedes myelination, Dev. Biol. 136:287–95.

Schwab, 1989, Substrates inhibiting neurite growth in the CNS, Experientia 45(Abstr.):A1.

Schwab, 1989, Neuron–glia interations in the development and regeneration of the central nervous system, Neurosci Lett., Suppl. 36.

Bandtlow et al., 1989, Oligodendrocytes inhibit neuronal growth cone movement, Experientia 45(Abstr.):A30.

Savio and Schwab, 1989, Rat CNS white matter, but not gray matter, is nonpermissive for neuronal cell adhesion and fiber outgrowth, J. Neurosci. 9:1126–33.

Schwab, 1989, Neurite growth inhibitors in the mammalian central nervous system, I.B.R.O. News 17:7.

Dutly et al., 1990, Purified oligodendrocyte precursor cells: interactions with neurons in culture, in Differentiation and Functions of Glial Cells: Proceedings of a Satellite Meeting of the International Society for Neurochemistry held in Rome, Italy, Apr. 19–21, 1989 (G. Levi, ed.; Wiley–Liss), pp. 149–150.

Savio et al., 1989, Cortico–spinal tract regeneration occurs in x–irradiated, myelin–free rat spinal cord, or by application of an antibody against myelin–associated neurite growth inhibitors, Soc. Neurosci. Abstr. 15:317.

Schwab et al., 1987, Oligodendrocytes and CNS myelin are nonpermissive substrates for neurite growth and fibroblast spreading, Chem. Abst. 109:108200y.

Boggust et al., 1978, Inhibition of collagen peptidase in hela cells and human tumours by compounds including drugs used in cancer therapy, Br. J. Cancer 38(2):329–34.

Guenther et al., 1985, A glia–derived neurite–promoting factor with protease inhibitory activity, EMBO 4:1963–66.

Barinage M., Science 264:772–774 (1994).

Saneto et al., in Neurochemistry: a practical approach (Turner ed.; IRL Press, 1987) pp. 28–63.

Hood et al., in Immunology (The Benjamin/Cummings Publishing Company, Inc., 1978),pp. 214–219.

Benacerraf et al., in Textbook of Immunology (Williams & Wilkins, 1979), pp. 32.

Caroni et al., Chem. Abst. 108: 219574X (1988).

Milstein, in Handbook of Experimental Immunology 4th Ed. (Blackwell Scientific Publications, 1986) Chap. 107, pp. 107.1–107.13.

Matrisian et al., 1986, The mRNA coding for the secreted protease transin is expressed more abundantly in malignant than in benign tumors, Proc. Natl. Acad. Sci. USA 83:9314–17.

Mignatti et al., 1986, Tumor invasion through the human amniotic membrane: requirement for a proteinase cascade, Cell 47:487–98.

Mullins and Rohrlich, 1983, The role of proteinases in cellular invasiveness, Biochim. Biophys. Acta 695:177–214.

Quigley, 1976, Association of a protease (plasminogen activator) with a specific membrane fraction isolated from transformed cells, J. Cell Biol. 71:472–86.

Mahdavi and Hynes, 1979, Proteolytic enzymes in normal and transformed cells, Biochim. Biophys. Acta 583:167–78.

Chen et al., 1984, Expression of transformation–associated protease(s) that degrade fibronectin at cell contact sites, J. Cell Biol. 98:1546–55.

Wilhem et al., 1987, Human skin fibroblast stromelysin: structure, glycosylation, substrate specificity, and differential expression in normal and tumorigenic cells, Proc. Natl. Acad. Sci. USA 84:6725–29.

Couch and Strittmatter, 1983, Rat myoblast fusion requires metalloendoprotease activity, Cell 32:257–65.

Mundy and Strittmatter, 1985, Requirement for metalloendoprotease in exocytosis: evidence in mast cells and adrenal chromaffin cells, Cell 40:645–56.

Almenoff and Orlowski, 1983, Membrane–bound kidney metalloendopeptidase: interaction with synthetic substrates, natural peptides, and inhibitors, Biochem. 22:590–99.

Chen and Chen, 1987, Fibronectin–degrading proteases from the membranes of transformed cells, Cell 48:193–203.

Monard et al., 1983, Inhibition of protease activity can lead to neurite extension in neuroblastoma cells, Prog. Brain Res. 58:359–64.

Hawkins and Seeds, 1986, Effect of proteases and their inhibitors on neurite outgrowth from neonatal mouse sensory ganglia in culture, Brain Res. 398:63–70.

Pittman, 1985, Release of plasminogen activator and a calcium–dependent metalloprotease from cultured sympathetic and sensory neurons, Dev. Biol. 110:91–101.

Caroni et al., 1988, CNS regeneration: oligodendrocytes and myelin as non–permissive substrates for neurite growth, Prog. Brain Res. 78:363–70.

Schwab, 1990, Myelin–associated inhibitors of neurite growth, Ex. Neurol. 109:2–5.

Schwab, 1991, Neurite growth inhibitors in the central nervous system: roles in development and regeneration, in Discussions in Neuroscience, T. Wiesel et al, eds., vol. VII, pp. 49–50.

Schwab et al., 1991, Neurite growth inhibitors in the adult mammalian central nervous system, in Neurogenerative Disorders: Mechanisms and Prospects for Therapy, Price et al., eds., J. Wiley & Sons Ltd., Life Sci. Res. Report LS51, pp. 157–164.

Schwab and Caroni, 1986, Rat CNS myelin and a subtype of oligodendrocytes in culture represent a non–permissive substrate for neurite growth and fibroblast spreading, Soc. Neurosci. 12:12A.

Schwab and Caroni, 1986, Rat CNS myelin and a subtype of oligodendrocytes in culture represent a non–permissive substrate for neurite outgrowth, Neurosci. Lett. 26:S19.

Bandtlow et al., 1987, Cellular localization of nerve growth factor synthesis by in situ hybridization, Soc. Neurosci. Abstr. 13:1616.

Pagnetti and Schwab, 1988, Glioblastoma cells overcome CNS tissue inhibitory substrate properties by means of metalloproteases, Europ. J. Neurosci., Suppl. 1, p. 240.

Pagnetti and Schwab, 1989, Glioblastoma infiltration into CNS tissue in vitro: involvement of two distinct proteases, J. Neuro–Oncology 7, Suppl., p. 24.

Pagnetti and Schwab, 1989, Glioblastoma infiltration into CNS tissue in vitro: involvement of two distinct proteases, Soc. Neurosci. Abstr. 15:507.

Pagnetti et al., 1989, Brain macrophage migration in CNS tissue in vitro, involvement of a metalloprotease, Experentia 45, A30.

Pagnetti and Schwab, 1990, Glioblastoma infiltration into CNS tissue in vitro: the role of a metalloprotease, Europ. J. Neurosci. Suppl. 3, 206.

Amberger et al., 1990, C6 rat glioblastoma cells use a specific proteolytic mechanism to overcome the inhibitory substrate effect of CNS white matter for invasive cell migration, Experientia 47, A2.

L. Schnell and M. E. Schwab, 1990, "Axonal regeneration in the rat spinal cord produced by an antibody against myelin–associated neurite growth inhibitors", Nature, vol. 343, pp. 269–272.

Bregman et al., 1995, "Recovery from spinal cord injury mediated by antibodies to neurite growth inhibitors", Nature, vol. 378, pp. 498–501.

Kromer et al., 1980, "Innervation of embryonic hippocampal implants by regenerating axons of cholinergic septal neurons in the adult rat", Brain Res vol. 210, p. 153.

Tuszynski et al., 1990, "Nerve Growth Factor Infusions Combined With Fetal Hippocampal Grafts Enhance Reconstruction of the Lesioned Septohippocampal Projection", Neurosci vol. 36, pp. 33–44.

Lieberman, 1971, "The Axon Reaction: A Review of the Principal Features of Perikaryal Responses to Axon Injury", Int J Neurol 14:49–124.

Brecknell et al., 1996, "Axonal Regeneration", Biol Rev 71:227–255.

Osband et al., 1990, "Problems in the Investigational Study and Clinical Use of Cancer Immunotherapy", Immunol. Today 11:193–195.

Harris et al., 1993 "Therapeutic Antibodies—the Coming of Age", Trends Biotechnol 11:42–44.

Brochier et al., 1995, "Immunomodulating IL–6 Activity by Murine Monoclonal Antibodies", Int J Immunopharamacol 17:41–48.

Hird et al., 1990, "Immunotherapy with Monoclonal Antibodies", in Genes and Cancers, Chapter 17, pp. 183–189, eds Carney and Sikova, John Wiley and Sons.

Zucker et al. J. of the National Cancer Inst. 75 (1985) 517–525.

Dyer "An Index of Tumor Chemotherapy" p. 69 (1951).

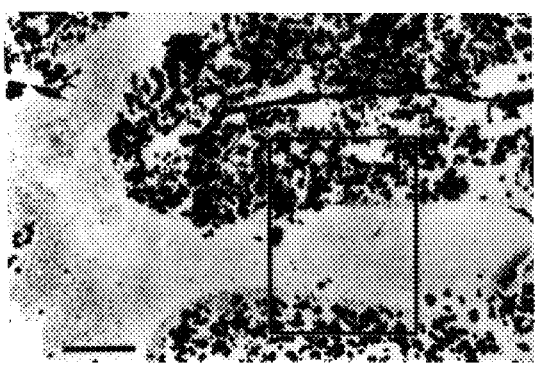
FIG. 20E
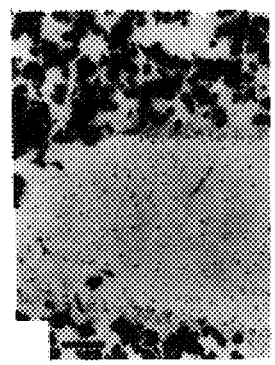
FIG. 20F
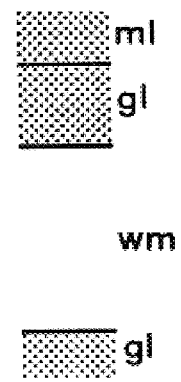

FIG. 24A
FIG. 24B
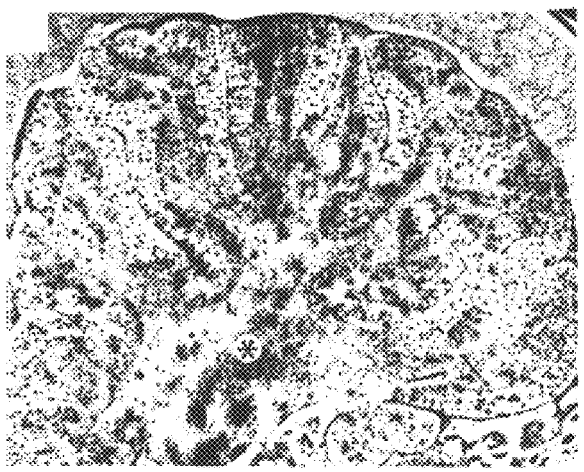
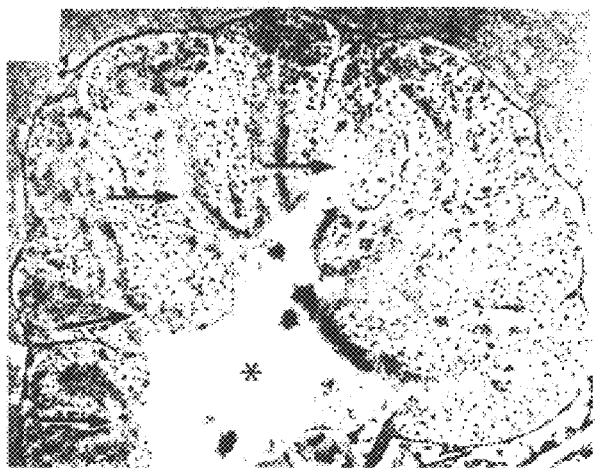

TREATMENT OF CNS TUMORS WITH METALLOPROTEASE INHIBITORS

This patent application is a divisional of application Ser. No. 07/401,212, filed Aug. 30, 1989, which is a continuation-in-part of U.S. patent application Ser. No. 07/267,941, filed Nov. 4, 1988, now abandoned, incorporated by reference herein in its entirety.

TABLE OF CONTENTS

1. Introduction
2. Background of the Invention
   2.1. Factors Influencing Neurite Growth
   2.2. Proteases and Their Inhibitors
   2.3. Neuroblastoma
   2.4. Glioblastoma
3. Summary of the Invention
   3.1. Definitions
4. Description of the Figures
5. Detailed Description of the Invention
   5.1. Isolation and Purification of Neurite Growth Regulatory Factors
      5.1.1. Isolation and Purification of CNS Myelin Associated Inhibitory Proteins
      5.1.2. Isolation and Purification of Receptors for the CNS Myelin Associated Inhibitory Proteins
      5.1.3. Isolation and Purification of Metalloproteases Associated With Malignant Tumors
   5.2. Protein Characterization
   5.3. Molecular Cloning of Genes or Gene Fragments Encoding Neurite Growth Regulatory Factors
      5.3.1. Isolation and Cloning of the Neurite Growth Regulatory Factor Genes
      5.3.2. Expression of the Cloned Neurite Growth Regulatory Factor Genes
      5.3.3. Identification and Purification of the Expressed Gene Product
      5.3.4. Characterization of the Neurite Growth Regulatory Factor Genes
   5.4. Production of Antibodies to Neurite Growth Regulatory Factors
   5.5. Neurite Growth Regulatory Factor-Related Derivatives, Analogs, and Peptides
   5.6. Uses of Neurite Growth Regulatory Factors
      5.6.1. Diagnostic Uses
         5.6.1.1. CNS Myelin Associated Inhibitory Proteins
         5.6.1.2. CNS Myelin Associated Inhibitory Protein Receptors
         5.6.1.3. Metalloproteases and their Inhibitors
      5.6.2. Therapeutic Uses
         5.6.2.1. CNS Myelin Associated Inhibitory Proteins
         5.6.2.2. CNS Myelin Associated Inhibitory Protein Receptors
         5.6.2.3. Metalloproteases and their Inhibitors
6. Oligodendrocytes and CNS Myelin are Nonpermissive Substrates for Neurite Growth and Fibroblast Spreading in Vitro
   6.1. Materials and Methods
      6.1.1. Glial Cell Cultures
      6.1.2. Glia-Nerve Cell Co-Cultures
      6.1.3. Immunofluorescence
      6.1.4. Evaluation of Co-Cultures With Nerve Cells, Neuroblastoma Cells, or 3T3 Cells
      6.1.5. Preparation of Myelin
   6.2. Results
      6.2.1. Cultures of Dissociated Young or Adult Rat Optic Nerves
      6.2.2. Subtypes of Oligodendrocytes
      6.2.3. Response of Various Cell Types to Highly Branched Oligodendrocytes
         6.2.3.1. Co-Cultures With Sympathetic or Sensory Neurons
         6.2.3.2. Co-Cultures With Fetal Rat Retinal Cells
         6.2.3.3. Response Of Other Cell Types To Highly Branched Oligodendrocytes
      6.2.4. Absence of Species Specificity
      6.2.5. Myelin as a Substrate
   6.3. Discussion
7. Two Membrane Protein Fractions From Rat Central Nervous System Myelin with Inhibitory Properties for Neurite Growth and Fibroblast Spreading
   7.1. Materials and Methods
      7.1.1. Cell Culture
      7.1.2. Sources of Tested Substrates
      7.1.3. Substrate Assaying Procedure
      7.1.4. Substrate-Processing
      7.1.5. Liposomes
      7.1.6. Gel-Extracted Protein Fractions As Substrate
   7.2. Results
      7.2.1. Nonpermissive Substrate Effect is found in CNS Myelin of Higher Vertebrates (Chick, Rat), but not Of Lower Vertebrates (Trout, Frog)
      7.2.2. Membrane-Bound Protein Fraction of Rat CNS Myelin is Responsible for its Nonpermissive Substrate Properties
      7.2.3. Identification of 35 kD and 250 kD Minor Proteins from Myelin as Nonpermissive Substrates For Fibroblast Spreading and Neurite Outgrowth
      7.2.4. Nonpermissive Substrate Property is Enriched in CNS White Matter and in Cultured Oligodendrocytes
   7.3. Discussion
8. Antibody Against Myelin-Associated Inhibitor of Neurite Growth Neutralizes Nonpermissive Substrate Properties of CNS White Matter
   8.1. Experimental Procedures
      8.1.1. Cell Culture
      8.1.2. Substrate Preparation
      8.1.3. Immunological Methods
         8.1.3.1. Radioimmunoassay
         8.1.3.2. Immunoblots
      8.1.4. Substrate Testing Procedures
      8.1.5. Neurite Growth Into Optic Nerve Explants In Vitro
   8.2. Results
      8.2.1. Antiserum Against Myelin Neutralizes the Nonpermissive Substrate Effects of CNS Myelin and of HBOs
      8.2.2. IN-1: A Monoclonal Antibody Against Gel Purified 250 kD Inhibitor from CNS Myelin Neutralizes Myelin Nonpermissiveness
      8.2.3. 250 kD and 35 kD Inhibitors from CNS Myelin Share Two Neutralizing Epitopes.
      8.2.4. IN-1 Specifically Immunoprecipitates Nonpermissive Substrated Activity from Solubilized Myelin Protein
      8.2.5. Nonpermissiveness of Adult Optic Nerve is Neutralized by Absorption With IN-1 Antibody 8.3. Discussion
9. Involvement of a Metalloprotease in Glioblastoma Infiltration Into Central Nervous System Tissue In Vitro
   9.1. Materials and Methods
      9.1.1. Cell Cultures
      9.1.2. Preparation of Nerve Explants for Infiltration Assay
      9.1.3. 5CNS Frozen Sections and Myelin as Substrates
      9.1.4. C6 Plasma Membranes and Conditioned Medium Preparation
      9.1.5. Treatment of CNS Myelin With C6 Plasma Membranes
   9.2. Results
      9.2.1. C6 Glioblastomas But Not 3T3 Fibroblasts Or B16 Melanomas Infiltrate Optic Nerve and CNS White Matter In Vitro
      9.2.2. Glioblastoma Cell Spreading is not Inhibited by CNS Myelin
      9.2.3. Specific Blockers of Metalloproteases Inhibit C6 Cell Spreading on CNS Myelin
      9.2.4. A C6 Plasma Membrane-Associated Activity Neutralizes The Inhibitory Substrate Property of CNS Myelin
      9.2.5. Inhibitors of Metalloproteases Impair C6 Cell Spreading on CNS White Matter and C6 Infiltration of CNS Explants
   9.3. Discussion
10. Long Distance Tract Regeneraction in the Lesioned Spinal Cord of Rats by a Monoclonal Antibody Against Myelin-Associated Neurite Growth Inhibitors
   10.1. Materials and Methods
      10.1.1. Pre-Operative Preparation of Animals, Including Implantation of Hybridoma Cells
      10.1.2. Procedure for Performing Spinal Cord Lesion
      10.1.3. Post-Lesion Evaluation
   10.2. Results: Regeneration of Corticospinal Tract (CST) Fibers Over Long Distances In Rats Bearing IN-1 Secreting Tumors
   10.3. Discussion
11. Deposit of Hybridomas

1. INTRODUCTION

The present invention is directed to genes and their encoded proteins which regulate neurite growth, antibodies thereto, and the therapeutic and diagnostic uses of such proteins and antibodies. The proteins of the present invention include central nervous system myelin associated inhibitory proteins, and metalloproteases associated with malignant tumors, in particular, primary brain tumors such as glioblastoma and other tumors capable of metastasizing to and spreading in the brain. The central nervous system myelin associated inhibitory proteins inhibit neurite outgrowth and fibroblast spreading and can have important uses in the treatment of malignant tumors. Antibodies to such inhibitory proteins can have uses in the diagnosis of malignant tumors and in the treatment of central nervous system damage and degenerative nerve diseases. In a specific embodiment of the invention, antibody to neurite growth inhibitor may be used to promote the regeneration of neurons over long distances following spinal cord damage. The metalloproteases of the invention allow invasive growth of glioblastomas and allow neurite outgrowth in central nervous system tissue. They may have important uses in the treatment of central nervous system damage and degenerative nerve diseases. Inhibition of the metalloprotease can be therapeutically useful in the treatment of malignant tumors.

2. BACKGROUND OF THE INVENTION

2.1. FACTORS INFLUENCING NEURITE GROWTH IN THE CENTRAL NERVOUS SYSTEM

Cell attachment, cell spreading, cell motility, and, in particular, neurite outgrowth are strongly dependent on cell-substrate interactions (Sanes, 1983, Ann. Rev. Physiol. 45:581–600; Carbonetto et al., 1987, J. Neurosci. 7:610–620). An increasing number of substrate molecules favoring neuroblast migration or neurite outgrowth have been found in central and peripheral nervous tissue (Cornbrooks et al., 1983, Proc. Natl. Acad. Sci. USA 80:3850–3854; Edelman, 1984, Exp. Cell Res. 161:1–16; Liesi, 1985, EMBO J. 4:1163–1170; Chiu, A. Y. et al., 1986, J. Cell Biol. 103:1383–1398; Fischer et al., 1986, J. Neurosci. 6:605–612; Lindner et al., 1986, Brain Res. 377:298–304; Mirsky et al., 1986, J. Neurocytol. 15:799–815; Stallcup et al., 1986, J. Neurosci. 5:1090–1101; Carbonetto et al., 1987, J. Neurosci. 7:610–620). The appearance of some of these factors can be correlated with specific developmental stages, and, in the peripheral nervous system (PNS), also with denervation (Edelman, 1984, Exp. Cell Res. 161:1–16; Liesi, 1985, EMBO J. 4:1163–1170; Stallcup et al., 1985, J. Neurosci. 5:1090–1101; Daniloff et al., 1986, J. Cell Biol. 103:929–945; Carbonetto et al., 1987, J. Neurosci. 7:610–620). The extracellular matrix protein tenascin has been shown to possess nonpermissive substrate properties (Chiquet-Ehrismann et al., 1986, Cell 47:131–139).

One of the most characterized of the soluble factors favoring neurite outgrowth is nerve growth factor (NGF). NGF promotes nerve fiber outgrowth from embryonic sensory and sympathetic ganglia in vivo and in vitro as well as neurite outgrowth (reviewed in Thoenen et al., 1982, In: Repair and Regeneration of the Nervous System, J. G. Nicholls, ed., Springer-Verlag, NY, pp. 173–185). NGF may also guide the direction of such neurite outgrowth. Three different molecular forms of NGF have been recognized. One type is a dimer (molecular weight ~26,000) composed of two noncovalently linked, identical polypeptide chains. The second form is stable at neutral pH and contains three different polypeptide chains, a, p and 7 (molecular weight ~140,000). The p chain is the biologically active chain and is identical to the first form of NGF. The third form, which is isolated primarily from mouse L cells, (see U.S. Pat. No. 4,230,691, by Young, issued Oct. 28, 1980, and references therein) has a molecular weight of about 160,000 but is unstable at neutral pH. NGF has thus far been isolated from the submandibullar glands of mice, mouse L cells, and the prostate gland of the guinea pig and bull (reviewed in Thoenen et al., 1982, supra). No differences between the biological action of mouse, guinea pig and bull NGF have been detected. In addition, NGF isolated from mice have been found to bind to the human NGF receptor (Johnson et al., 1986, Cell 47:545–554).

The differentiated central nervous system (CNS) of higher vertebrates is capable of only very limited regenerative neurite growth after lesions. Limited regeneration after lesion has been seen in the retina (McConnell and Berry, 1982, Brain Res. 241:362–365) and in aminergic unmyelinated fiber tracts after chemical (Bjorklund and Stenevi, 1979, Physiol. Rev. 59:62–95) but not mechanical lesions (Bregman, 1987, Dev. Brain Res. 34:265–279). Neurite growth from implanted embryonic CNS tissues in adult rat CNS has been found in some cases to reach up to 14 mm within some gray matter areas, but has not been found to exceed 1 mm within white matter (Nornes et al., 1983, Cell Tissue Res. 230:15–35; Bjorklund and Stenevi, 1979, Physiol. Rev. 59:62–95; Commission, 1984, Neuroscience 12:839–853). On the other hand, extensive regenerative growth has been found in the CNS of lower vertebrates and in the peripheral nervous system of all vertebrates including man. Results from transplantation experiments indicate that the lack of regeneration is not an intrinsic property of CNS neurons, as these readily extend processes into implanted peripheral nervous tissue (Benfey and Aguayo, 1982, Nature (London) 296:150–152; Richardson et al., 1984, J. Neurocytol. 13:165–182 and So and Aguayo, 1985, Brain Res. 328:349–354). PNS neurons, however, failed to extend processes into CNS tissue, thus indicating the existence of fundamental differences between the two tissues (Aguayo et al., 1978, Neurosci. Lett. 9:97–104; Weinberg and Spencer, 1979, Brain Res. 162:273–279).

One major difference between PNS and CNS tissue is the differential distribution of the neurite outgrowth promoting extracellular matrix component laminin (Liesi, 1985, EMBO J. 4:2505–2511; Carbonetto et al., 1987, J. Neurosci. 7:610–620). Other factors though may be involved. Drastic differences have been observed in neurite growth supporting properties of sciatic and of optic nerve explants in vitro, in spite of the presence of laminin immunoreactivity in both explants (Schwab and Thoenen, 1985, J. Neurosci. 5:2415–2423). These experiments were carried out in the presence of optimal amounts of neurotrophic factors and differences persisted upon freezing of tested substrates.

It has been suggested that the differentiated CNS may lack cellular or substrate constituents that are conducive for neurite growth during development (Liesi, 1985, EMBO J. 4:2505–2511; and Carbonetto et al, 1987, J. Neurosci. 7:610–620), or it may contain components which are nonpermissive or inhibitory for nerve fiber regeneration (Schwab and Thoenen, 1985, J. Neurosci. 5:2415–2423).

Recently, a growth (cell proliferation) inhibitory factor for mouse neuroblastoma cells was partially purified and characterized from the culture medium of fetal rat glioblasts as well as from C6 rat glioma cells (Sakazaki et al., 1983, Brain Res. 262:125–135). The factor was estimated to have a molecular weight of about 75,000 by gel filtration with BioGel P-20 with an isoelectric point of 5.8. The factor did not appear to alter the growth rate or morphology of glial cells (C6) or fibroblasts (3T3). In addition, no significant nerve growth inhibitory factor activity was detected towards neuroblastoma cells (Neuro La, NS-20Y and NIE-115) or cloned fibroblasts (3T3).

2.2. PROTEASES AND THEIR INHIBITORS

Different proteolytic activities have in the past been shown to be increased in tumorigenic cell lines (Matrisian et al., 1986, Proc. Natl. Acad. Sci. U.S.A. 83:9413–9417; Mignatti et al., 1986, Cell 47:487–498), in primary tumor explants (Mullins and Rohrlich, 1983, Biochem. Biophys. Acta 695:177–214), or in transformed cells (Quigley, 1976, J. Cell Biol. 71:472–486; Mahdavi and Hynes, 1979, Biochem. Biophys. Acta 583:167–178; Chen et al., 1984, J. Cell Biol. 98:1546–1555; Wilhelm et al., 1987, Proc. Natl. Acad. Sci. U.S.A. 84: 6725–6729). One such group of proteases, metalloproteases has been shown to be involved in a number of membrane events, including myoblast fusion (Couch and Stritmatter, 1983, Cell 32:256–265), and exocytosis in mast cells (Mundy and Stritmatter, 1985, Cell 40:645–656).

The isolation and characterization of a plasma membrane-bound metalloprotease (endopeptidase 24.11, enkephalinase) was reported by Almenoff and Orlowski (1983, Biochemistry 22:590–599). A metalloprotease expressed by Rous sarcoma virus transformed chick embryo fibroblasts which degrades fibronectin and which was localized at adhesion sites and on "invadopodia" was described by Chen and Chen (1987, Cell 48:193–203).

Studies indicate that proteases and their inhibitors can influence neurite extension in neuroblastoma cells (Monard et al., 1983, Prog. Brain Res. 58:359–363) and in cultured neonatal mouse sensory ganglia (Hawkins and Seeds, 1986, Brain Res. 398:63–70). Cultured glial cells and gliomas were found to release a 43 kD protein, a glia derived neurite promoting factor (GdNPF), which induces neurite outgrowth in neuroblastoma cells but inhibits cell migration (Monard, et al., 1983, supra). GdNPF was shown to be a very potent inhibitor of cell surface associated serine protease activity. Neurite outgrowth from normal mouse sensory ganglia can be enhanced by the addition of serine protease inhibitors, ovomucoid trypsin inhibitor, leupeptin, soybean trypsin inhibitor, or thrombin (Hawkins and Seeds, 1986, supra). In contrast, proteases were found to inhibit such neurite outgrowth. Results from preliminary studies indicate that such proteases possess a thrombin or trypsin like activity (Hawkins and Seeds, 1986, supra).

Other proteases have also been characterized though their functional role in neurite outgrowth is as yet unknown. These include a urokinase-like plasminogen activator and a calcium dependent metalloprotease released by sympathetic and sensory rat neurons (Pittman, 1985, Dev. Biol. 110:911–101). The metalloprotease was found to have a molecular weight of 62 kD, to require 1 mM $Ca^{2+}$ for calcium activity, and to degrade native and denatured collagen more readily than casein, albumin, or fibronectin. The plasminogen activator was found to have a molecular weight of 51 kD, and was precipitated by a rabbit antiserum produced against human urokinase. It may be converted to its active form of 32 kD.

2.3. NEUROBLASTOMA

Neuroblastoma arises from neuroectoderm and contains anaplastic sympathetic ganglion cells (reviewed in Pinkel and Howarth, 1985, In: Medical Oncology, Calabrese, P., Rosenberg, S. A., and Schein, P. S., eds., MacMillan, N.Y., pp. 1226–1257). One interesting aspect of neuroblastoma is that it has one of the highest rates of spontaneous regression among human tumors (Everson, 1964, Ann. NY Acad. Sci. 114:721–735) and a correlation exists between such regression and maturation of benign ganglioneuroma (Bolande, 1977, Am. J. Dis. Child. 122:12–14). Neuroblastoma cells have been found to retain the capacity for morphological maturation in culture. The tumors may occur anywhere along the sympathetic chain, with 50% of such tumors originating in the adrenal medulla.

Neuroblastoma affects predominantly preschool aged children and is the most common extracranial solid tumor in childhood, constituting 6.5% of pediatric neoplasms. One half are less than two years of age upon diagnosis. Metastases are evident in 60% of the patients at presentation usually involving the bones, bone marrow, liver, or skin. The presenting symptoms may be related to the primary tumor (spinal coral compression, abdominal mass), metastatic tumor (bone pain) or metabolic effects of substances such as catecholamines or vasoactive polypeptides secreted by the tumor (e.g. hypertension, diarrhea).

Experimental evidence indicates that an altered response to NGF is associated with neuroblastoma (Sonnenfeld and Ishii, 1982, J. Neurosci. Res. 8:375–391). NGF stimulated neurite outgrowth in one-half of the neuroblastoma cell lines tested; the other half was insensitive. However, NGF neither reduced the growth rate nor enhanced survival in any neuroblastoma cell line.

Present therapies for neuroblastoma involve surgery and/or chemotherapy. Radiation therapy is used for incomplete tumor responses to chemotherapy. There is a 70–100% survival rate in individuals with localized tumors, but only a 20% survival rate in those with metastatic disease even with multiagent chemotherapy. It appears that patients less than one year have a better prognosis (70%) than older children.

2.4. GLIOBLASTOMA

Glioblastoma is a highly malignant astrocytic tumor usually located in the cerebral hemisphere. Astrocytes appear to be a supporting tissue for neurons and comprise the vast majority of the intraparenchymal cells of the brain (reviewed in Cutler, 1987, In: Scientific American Medicine V. 2, Rubenstein and Federman, eds., Scientific American, Inc., NY, pp. 1–7). Results from a survey conducted by the National Institute of Neurological and Communicative Disorders and Stroke indicated that the incidence of primary brain tumors in the United States is approximately eight per 100,000, in which 20% of those tumors are glioblastomas. These tumors are generally found in individuals between 45 and 55 years of age. The tumors may also involve multiple lobes and may rupture into the ventricular system or extend across the corpus collosum to the opposite hemisphere. Due to the resulting increase in intracranial pressure, symptoms of tumor growth include headache, nausea and vomiting, mental status changes, and disturbances of consciousness. Due to their highly invasive properties, glioblastomas are associated with a poor prognosis. Chemotherapeutic agents or radiotherapies may be used. However, patients generally do not survive longer than two years even with these therapies.

3. SUMMARY OF THE INVENTION

The present invention relates to genes and their encoded proteins which regulate neurite growth and the diagnostic and therapeutic uses of such proteins. Such proteins are termed herein neurite growth regulatory factors. The neurite growth regulatory factors of the present invention include, in one embodiment, central nervous system myelin associated proteins which inhibit neurite outgrowth, and are termed herein neurite growth inhibitory factors. Another embodiment of the invention is directed to neurite growth regulatory factors which are metalloproteases associated with malignant tumors, in particular, those tumors metastatic to the brain. Such metalloproteases enable the malignant cells to overcome the inhibitory CNS environment and invade large areas of brain and spinal cord.

The CNS myelin associated proteins inhibit neurite outgrowth in nerve cells and neuroblastoma cells and also inhibit the spreading of fibroblasts and melanoma cells. Such inhibitory proteins include but are not limited to 35,000 dalton and a 250,000 dalton molecular weight proteins and analogs, derivatives, and fragments thereof. The CNS myelin associated inhibitory proteins may be used in the treatment of patients with malignant tumors which include but are not limited to melanoma and nerve tissue tumors (e.g., neuroblastoma). The absence of the myelin associated inhibitory proteins can be diagnostic for the presence of a malignant tumor such as those metastatic to the brain (e.g., glioblastoma). The present invention also relates to antagonists of the CNS myelin associated inhibitory proteins, including, but not limited to, antibodies, i.e. antibodies IN-1 or IN-2. Such antibodies can be used to neutralize the neurite growth inhibitory factors for regenerative repair after trauma, degeneration, or inflammation. In a further specific embodiment, monoclonal antibody IN-1 may be used to promote regeneration of nerve fibers over long distances following spinal cord damage.

The present invention further relates to neurite growth regulatory factor receptors and fragments thereof as well as the nucleic acid sequences coding for such neurite growth regulatory factor receptors and fragments, and their therapeutic and diagnostic uses. Substances which function as either agonists or antagonists to neurite growth regulatory factor receptors are also envisioned and within the scope of the present invention.

The metalloproteases of the present invention can be found associated with malignant tumors, in particular, those capable of metastasizing to the brain. In a specific embodiment, the metalloprotease is associated with membranes of glioblastoma cells. The metalloproteases, and analogs, derivatives, and fragments thereof can have value in the treatment of nerve damage resulting from trauma, stroke, degenerative disorders of the central nervous system, etc. In another embodiment of the invention, the metalloprotease may be used in combination with antibodies to the neurite growth inhibitory factors to treat nerve damage.

The present invention is also directed to inhibitors of and/or antibodies to the metalloproteases of the invention. Such inhibitors and/or antibodies can be used in the diagnosis and/or treatment of malignant tumors such as those which can metastasize to the brain, including but not limited to glioblastomas. Alternatively, the metalloprotease inhibitors, in combination with CNS myelin associated inhibitory protein or analogs, derivatives, or fragments thereof, may be used in the treatment and/or diagnosis of malignant tumors including but not limited to glioblastoma, neuroblastoma, and melanoma.

3.1. DEFINITIONS

As used herein, the following terms shall have the meanings indicated:
BSA: bovine serum albumin
cbz-tyr-tyr: carbobenzoxy-tryosine-tyrosine
cbz-gly-phe-$NH_2$: carbobenzoxy-glycine-phenylalanine-amide
cbz-ala-phe-$NH_2$: carbobenzoxy-alanine-phenylalanine-amide
cbz-phe-phe-$NH_2$: carbobenzoxy-phenylalanine-phenylalanine-amide
cbz-gly-phe-phe-$NH_2$: carbobenzoxy-glycine-phenylalanine-phenylalanine-amide
CNS: central nervous system
CST: Corticospinal tract
DMEM: Dulbecco's Modified Minimal Essential Media
EDTA: ethylenediamine tetracetate
EGTA: ethylene glycol-bis-($\beta$-aminoethyl ether)-N,N,N'-N'-tetracetate
FCS: fetal calf serum
FITC: fluorescein isothiocyanate
GdNPF: glial-derived neurite promoting factor
GFAP: glial fibrillary acid protein
HBO: highly branched oligodendrocyte
Hepes: N-2-hydroxyethylpiperazine-N'-2-ethanesulfonic acid IN-1: a monoclonal antibody against gel-purified 250 kD CNS myelin associated inhibitory protein IN-2: a monclonal antibody against gel-purified 35 kD CNS myelin associated inhibitory protein J1: a cell adhesion molecule of molecular weight 160–180 kD kD: kilodalton Mab: monoclonal antibody MW: molecular weight N-CAM: neural cell adhesion molecule NGF: nerve growth factor neurite growth regulatory factors: CNS myelin associated 35 kD and 250 kD inhibitory proteins, and a glioblastoma cell membrane associated metalloprotease PBS: phosphate buffered saline PLYS: poly-D-lysine PNS: peripheral nervous system PORN: polyornithine SCG: superior cervical ganglion SDS-PAGE: sodium dodecyl sulfate-polyacrylamide gel electrophoresis Tris: Tris (hydroxymethyl) aminomethane

4. DESCRIPTION OF THE FIGURES

FIGS. 1A–H. Sympathetic (A–D) or retinal (E) neurons plated into cultures of optic nerve glial cells show nonpermissive substrate effect of highly branched oligodendrocytes and the absence of such effect in immature oligodendrocytes. FIGS. 1A, C, E, G show phase contrast pictures. FIGS. 1B, D, F show immunofluorescence with antibody $O_4$. FIG. 1H shows immunofluorescence with antibody $O_1$.

FIGS. 1A and 1B show "windows" (areas free of neurites) formed by highly branched oligodendrocytes (10-day-old optic nerves, 18 days in vitro) in the neurite plexus of sympathetic neurons (A: 8 days in vitro; B: 4 days in vitro). Magnification: ×120. In FIG. 1B, a neurite changing its direction is seen (arrow-head). Schwann cells also avoid the oligodendrocyte.

FIGS. 1C and 1D show antibody $O_4$-positive oligodendrocytes (from 10-day-old optic nerves, 7 days in vitro) surrounded by plexus of sympathetic neurites (5 days in vitro). Magnification: ×220. Neurites characteristically "loop around" the oligodendrocytes. The occasional spanning of neurite bundles over nonpermissive oligodendrocytes occurs as a secondary event.

FIGS. 2A–D. A, B: Histograms showing the frequency of interactions/overlap of sympathetic neurites and Schwann cells with highly branched (A) or immature (B) oligodendrocytes. Glial cells from 8 to 10-day optic nerves (2 days in vitro) were co-cultured for an additional 2 days with dissociated neurons from superior cervical ganglia and then stained with antibody $O_4$. Oligodendrocytes were classified by morphology on coded fluorescence pictures. On phase contrast pictures, the fractional area of contact with neurites and Schwann cells was determined and classified into 3 categories: <20%, 20 to 80%, or >80% of oligodendrocyte territory covered by neurites or Schwann cells. Values represent mean frequencies of cells in 3 categories±SEM (standard error of the mean) (4 cultures; 70 to 130 systematically sampled cells per culture).

C, D: Histograms showing the interaction of retinal cells with highly branched (C) or immature (D) oligodendrocytes. Glial cultures from adult rat optic nerves (6–11 days in vitro) were co-cultured for 1–5 days with embryonic rat retinal cells. Antibody $O_4$ stained oligodendrocytes were classified morphologically, and the total area occupied by each oligodendrocyte as well as the fraction occupied by retinal cells was determined by measuring with a graphic tablet. n=109.

FIGS. 3A–D. Astrocytes represent an adhesive substrate for neurons and neurites.

Figure 3A:
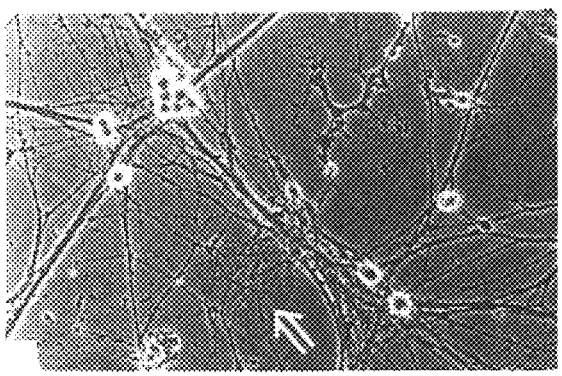
Figure 3B:
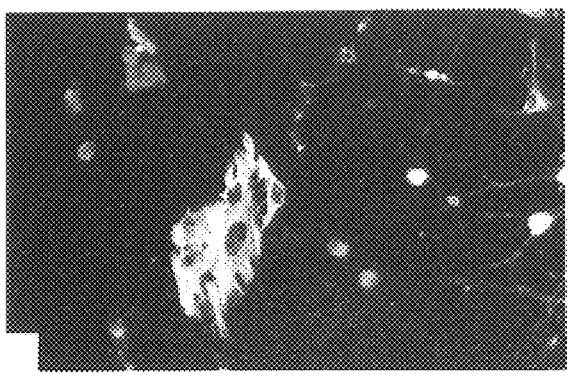

FIGS. 3A and 3B show sympathetic neurites (13 days in vitro) growing on reactive protoplasmic astrocyte (arrow in A); GFAP POSITIVE (B): from 10-day-old rat optic nerve, 23 days in vitro. Magnification: ×220.

Figure 3C:
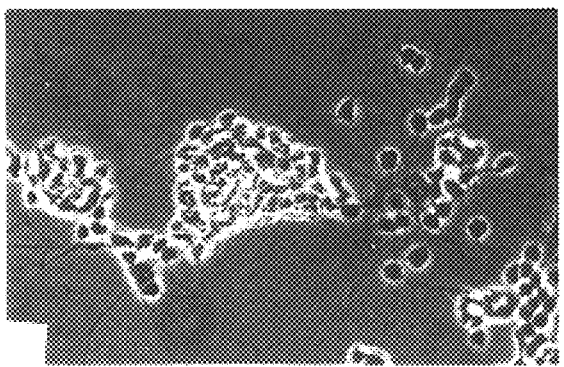
Figure 3D:
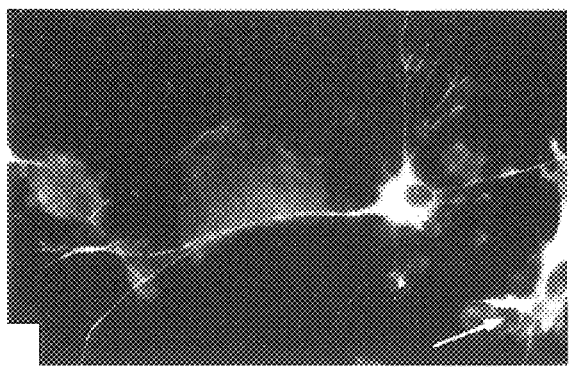

FIGS. 3C and D show retinal cells (from E17 retina, 2 days in vitro) adhering to astrocytes (GFAP-positive, FIG. 3D); from 10-day-old optic nerve, 9 days in vitro) with long and with short (arrow) processes. Magnification: ×400.

FIGS. 4A–F. A, B: Highly branched oligodendrocytes ($O_4$-positive) are non-permissive for attachment and fiber outgrowth of NB-2A neuroblastoma cells. NB-2A cells were cultured for 24 hours on optic nerve glial cells (6-day old rat optic nerves, 3 days in culture) and stimulated for neurite outgrowth by GdNPF (Guenther et al., 1985, EMBO J. 4:1963–1966). NB-2A cells adjacent to oligodendrocytes (short arrows) show assymmetric ougrowth; distant cells (long arrows) show random orientation of outgrowth. Magnification: ×260. C–F: 3T3 fibroblasts plated at high cell densities into optic nerve glial cultures show nonpermissive substrate effect of highly branched oligodendrocytes (C, E). The oligodendrocyte in C/D has large membrane areas connecting its process network. An immature oligodendrocyte (E, F: arrow; $O_4$-positive, irregular morphology) is overgrown by spreading fibroblasts. 10-(C, D) and 12-(E, F) day old optic nerves, 2 days int, vitro; 3T3 added for 3 hours. D, F: $O_4$-staining. C, D: magnification is ×300; E, F: magnification is ×250.

Figure 5:
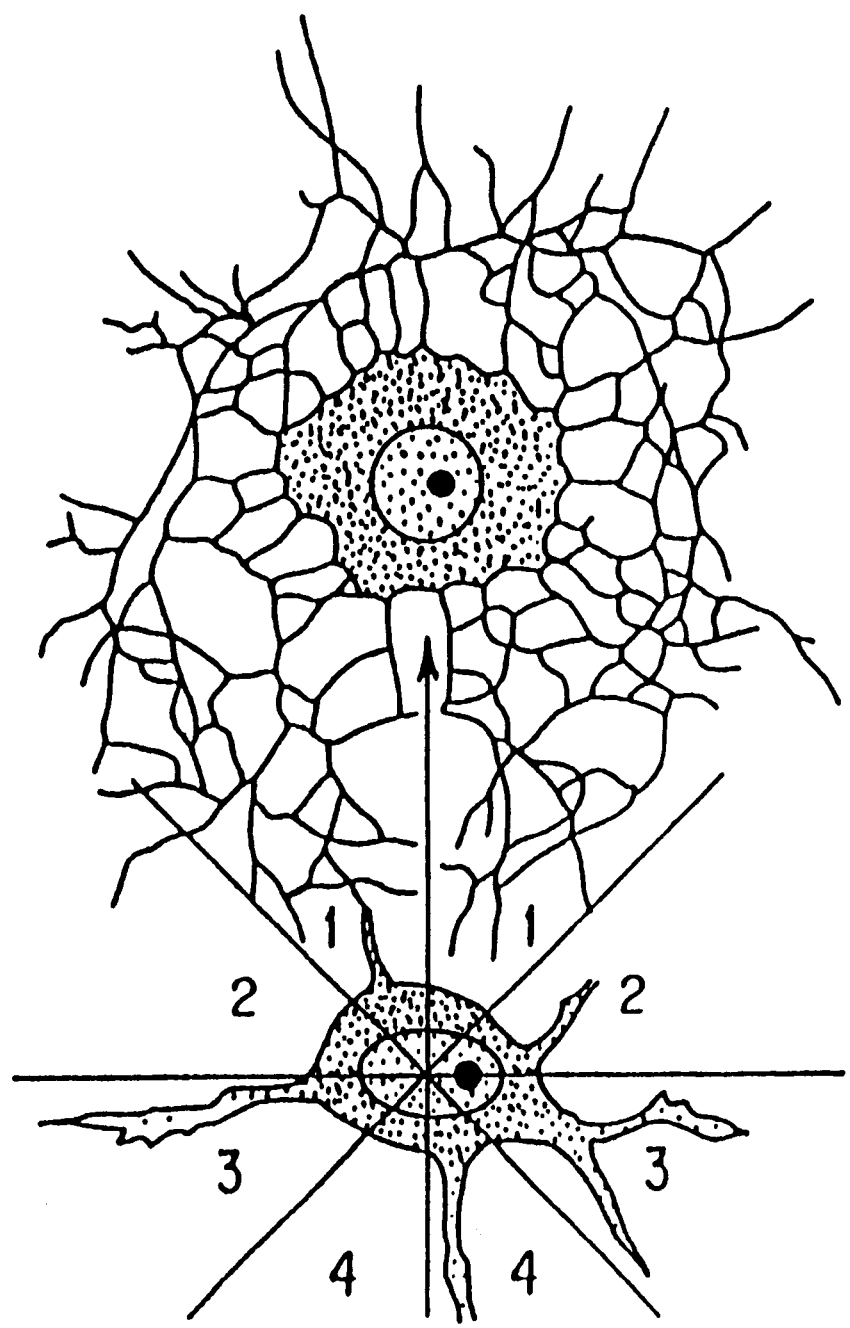

FIG. 5. Orientation of neuroblastoma process outgrowth in relation to highly branched oligodendrocytes. Optic nerve glial cells (2 or 6 days in vitro) were co-cultured with NB-2A cells for 24 hours in presence of GdNPF or dibutyryl CAMP. Antibody $O_4$-positive highly branched oligodendrocytes were systematically sampled and neighbouring neuroblastoma cells were classified as adjacent when the distance between the edge of oligodendrocyte process network and neuroblastoma cell body was less than 2 cell body diameters. Neuroblastoma cells at greater distances were classified as distant. Neuroblastoma processes were assigned to four sectors (1–4) according to their direction with regard to the closest oligodendrocyte as illustrated. Values, shown in Table IA (Section 6.2.3.3., infra) represent means±SEM of 3 experiments (60–100 neurites from 3 cultures per experiment). * $p<0.05$; * * * $p<0.001$.

Figure 6A:
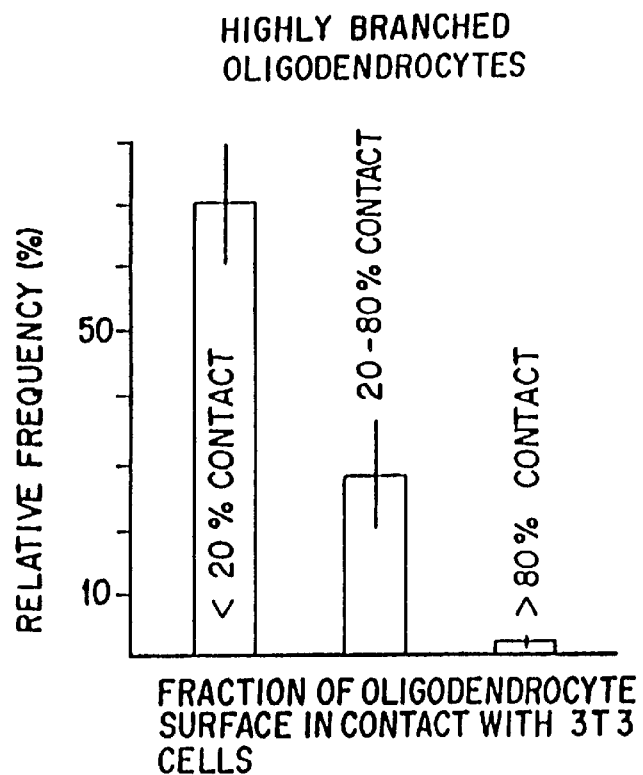
Figure 6B:
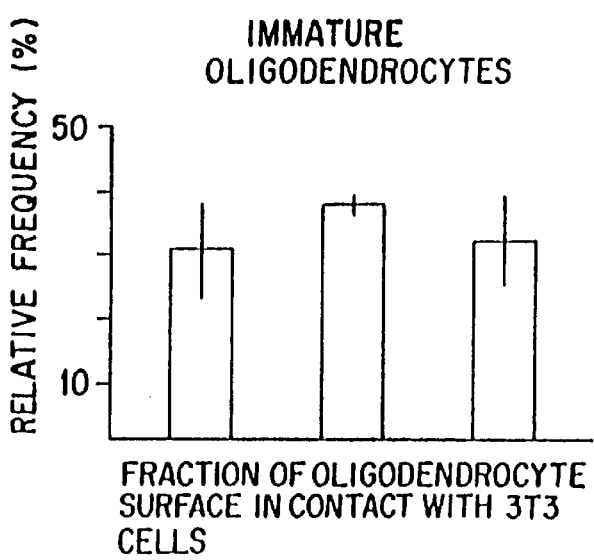

FIGS. 6A–B. Histograms showing the overlap of 3T3 cells with highly branched (A) or immature (B) oligodendrocytes. 3T3 cells were co-cultured for 3–4 hours on optic nerve glial cells at high cell density, and cultures fixed and stained with antibody $O_4$. Oligodendrocytes were sampled systematically, classified as highly branched or immature oligodendrocytes, and their overlap with 3T3 cells was determined in the 3 categories indicated. Values represent means±SEM (standard error measurement) of four experiments (70–170 cells).

FIGS. 7A–D. Inhibition of neurite outgrowth by use of CNS myelin as a substrate. Sympathetic neurons (from 1-day-old rat superior cervical ganglia) cultured in the presence of 100 ng/ml NGF for 26 hours on poly-D-lysine (PLYS)-coated culture dish containing focal spots of CNS or PNS myelin. CNS myelin (A, C) strongly inhibits neurite outgrowth; PNS myelin (B, D) is a permissive substrate. In C and D, the border of a myelin islet on the PLYS is shown. Magnification: ×75.

Figure 8A:
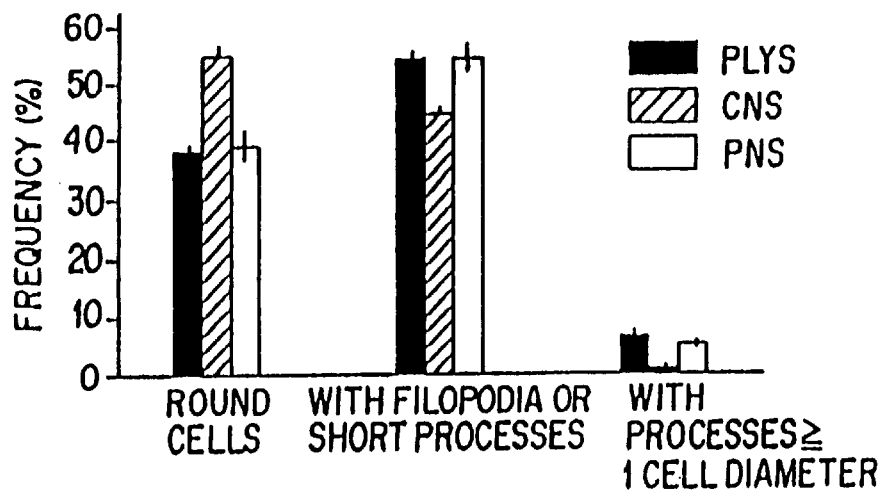
Figure 8B:
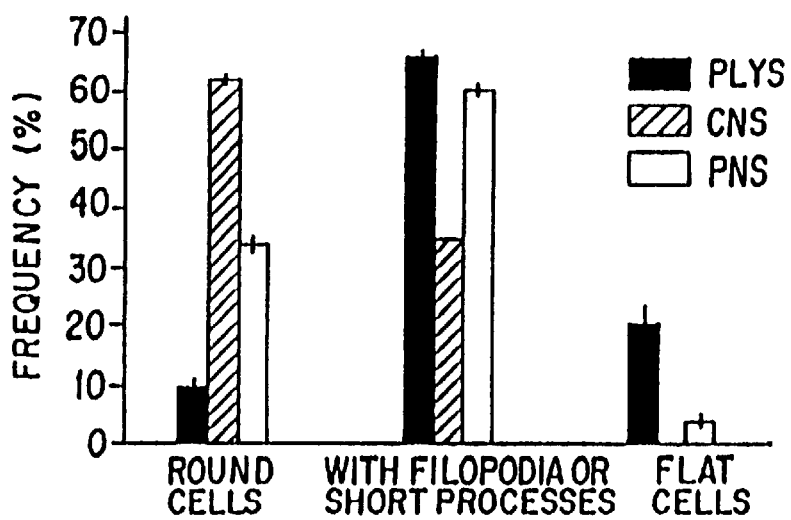

FIGS. 8A–B. Nonpermissive substrate effects of CNS myelin but not PNS myelin for neurite outgrowth from neuroblastoma cells (A) and for 3T3 cell spreading (B).

FIG. 8A shows neuroblastoma cells cultured for 5 hours in the presence of 2 mM dibutyrylcyclic AMP on PLYS (solid bars), CNS myelin coated PLYS (hatched bars), or PNS myelin-coated PLYS (open bars). Cells were classified as round cells, filopodia or short process carrying cells, or cells with processes longer than 1 cell diameter. Values represent means±SEM of 3 cultures (250–450 cells per culture).

FIG. 8B shows 3T3 cells cultured for 1 hour on PLYS, CNS myelin-coated PLYS, or PNS myelin-coated PLYS. Cells were classified as round cells, cells with filopodia or short processes, or large flat cells. Values represent means±SEM of 3 cultures (300–400 cells per culture).

Figure 9:
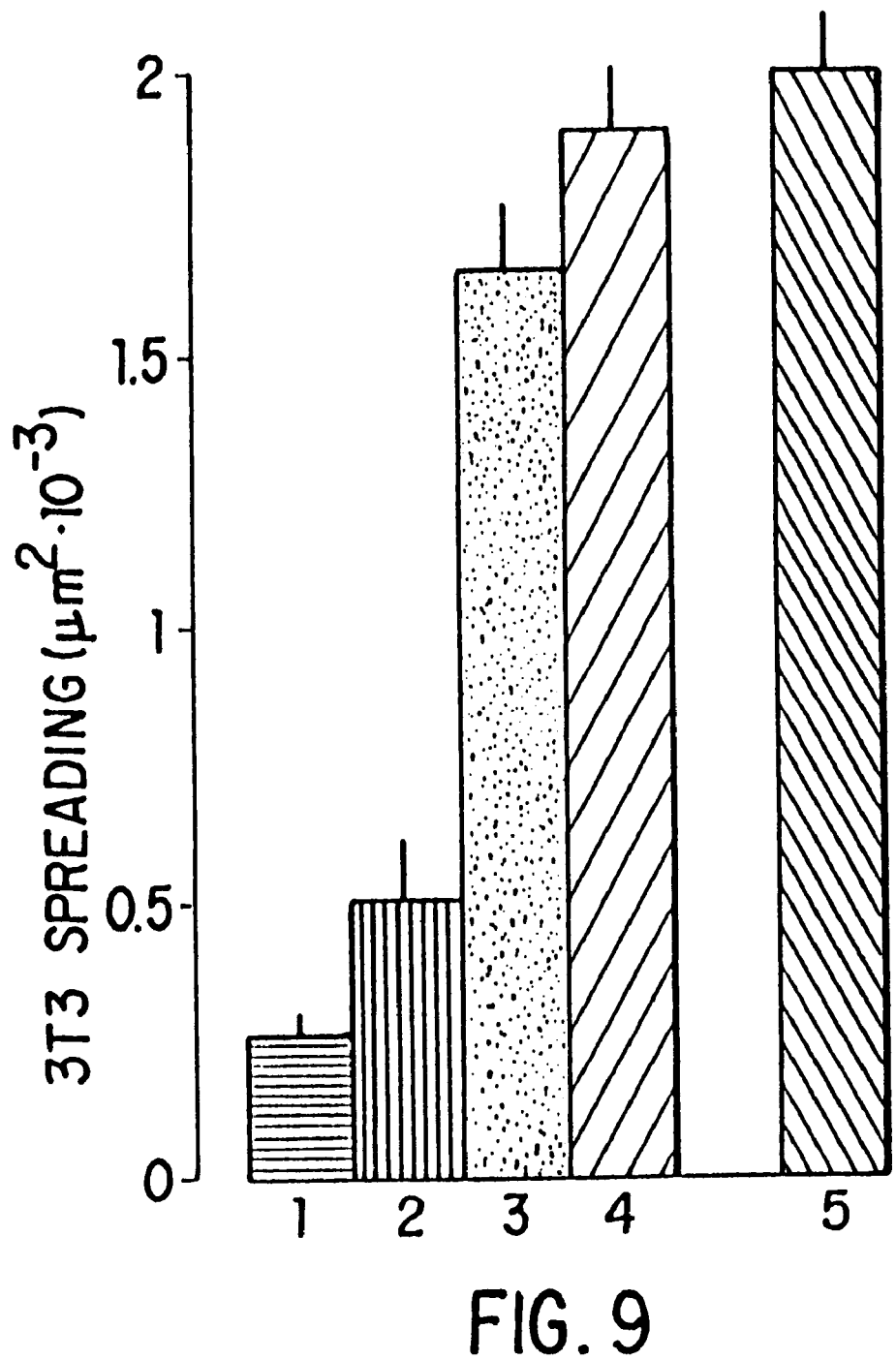

FIG. 9. Substrate properties of CNS myelin fractions from rat, chick, trout, and frog. Spinal cord myelin fractions from different species were adsorbed to PLYS-coated wells of dishes (Greiner). 3T3 cells were added and experiments were scored after 1 hour. Spreading values are given as mean±SEM. Substrates: myelin fractions from: (1) rat CNS; (2) chick CNS; (3) trout CNS; (4) frog CNS; (5) rat PNS.

Figure 10:
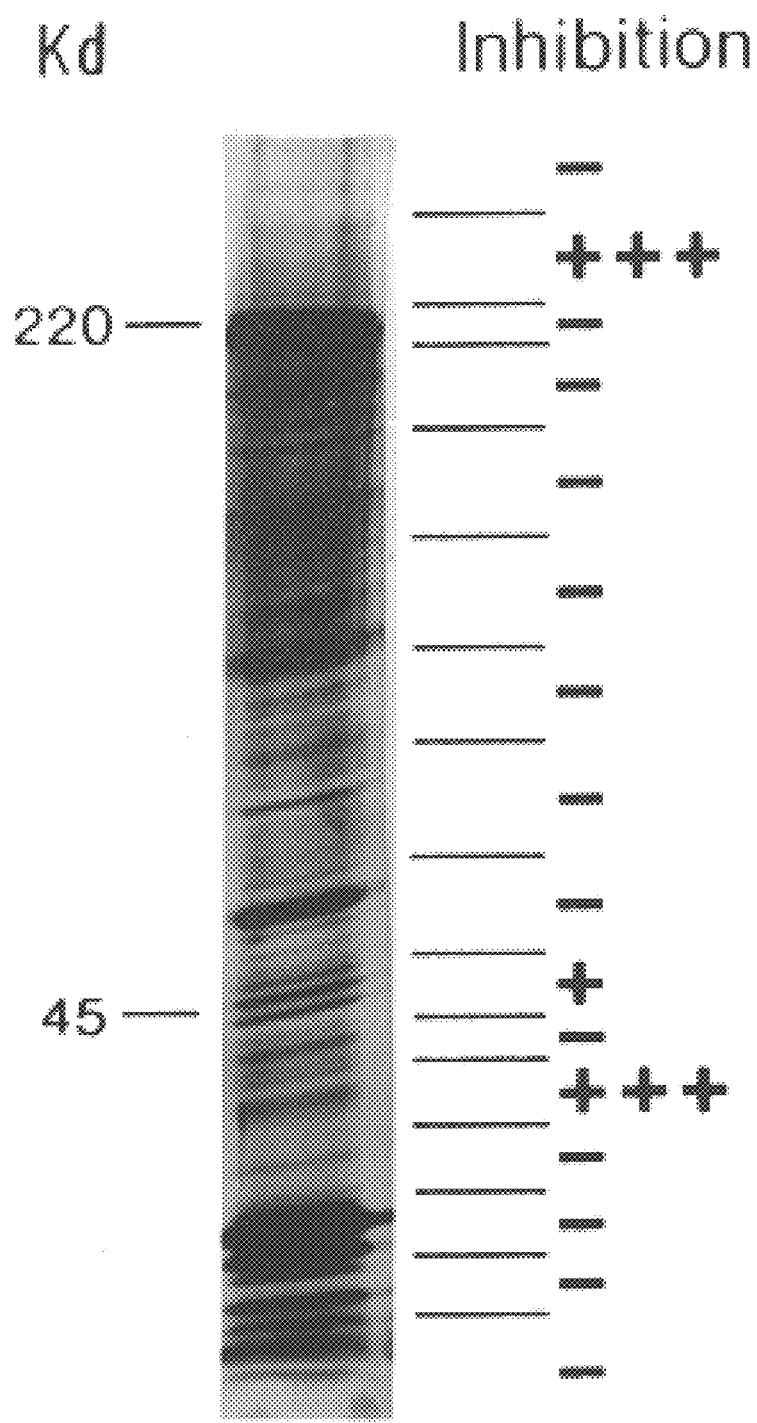

FIG. 10. SDS-PAGE fractionation of rat CNS myelin protein. Nonpermissive substrate proteins comigrates with proteins of 250 and of 35 kD on a 3–15% polyacrylamide-reducing gradient gel of rat CNS myelin protein. Protein from the indicated gel regions was extracted and activity-containing regions of ~35 and 250 kD proteins were determined by assaying the nonpermissiveness of corresponding liposomes. Molecular masses were estimated from commercial standards (Sigma Chemical Co.)

Figure 11A:
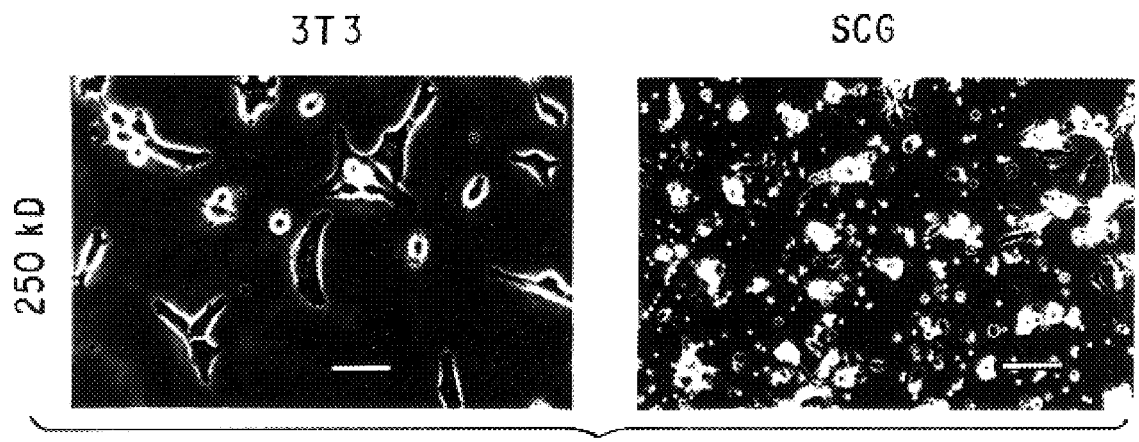
Figure 11B:
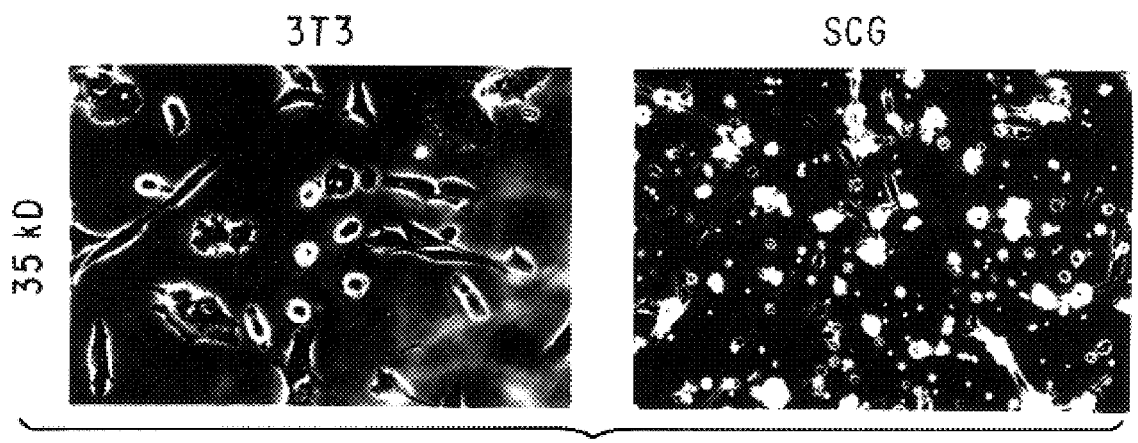
Figure 11C:
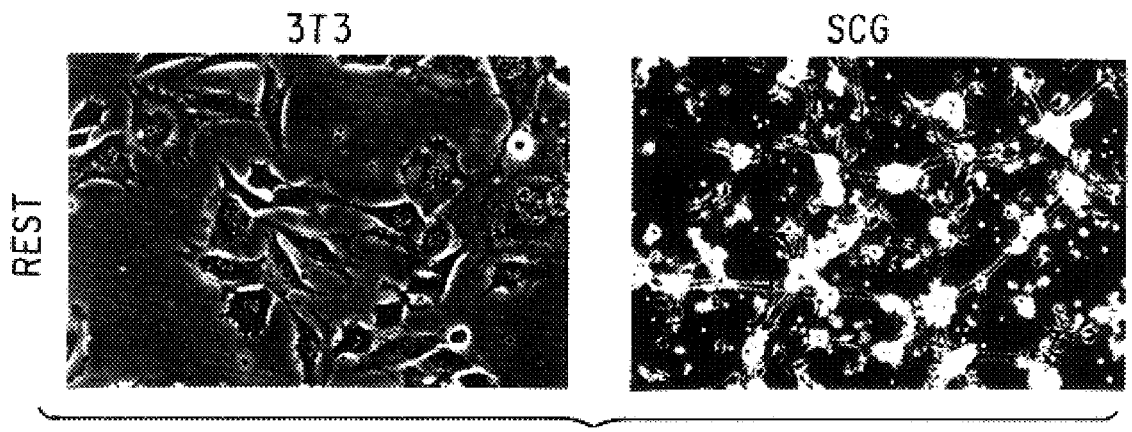

FIGS 11A–C. 35 and 250 kD (11A and 11B, respectively) protein fractions from rat CNS myelin are nonpermissive substrates for 3T3 spreading and neurite outgrowth. Liposomes formed in the presence of gel-extracted protein fractions as indicated were tested for their substrate properties. Substrate designated as rest: protein from pooled gel regions excluding the 35 kD and 250 kD fractions. Incubation times were one (3T3 cells) and 24 hours (SCG neurons in the presence of NGF), respectively. Bars: (3T3) 100 µm; (SCG) 50 µm.

Figure 12:
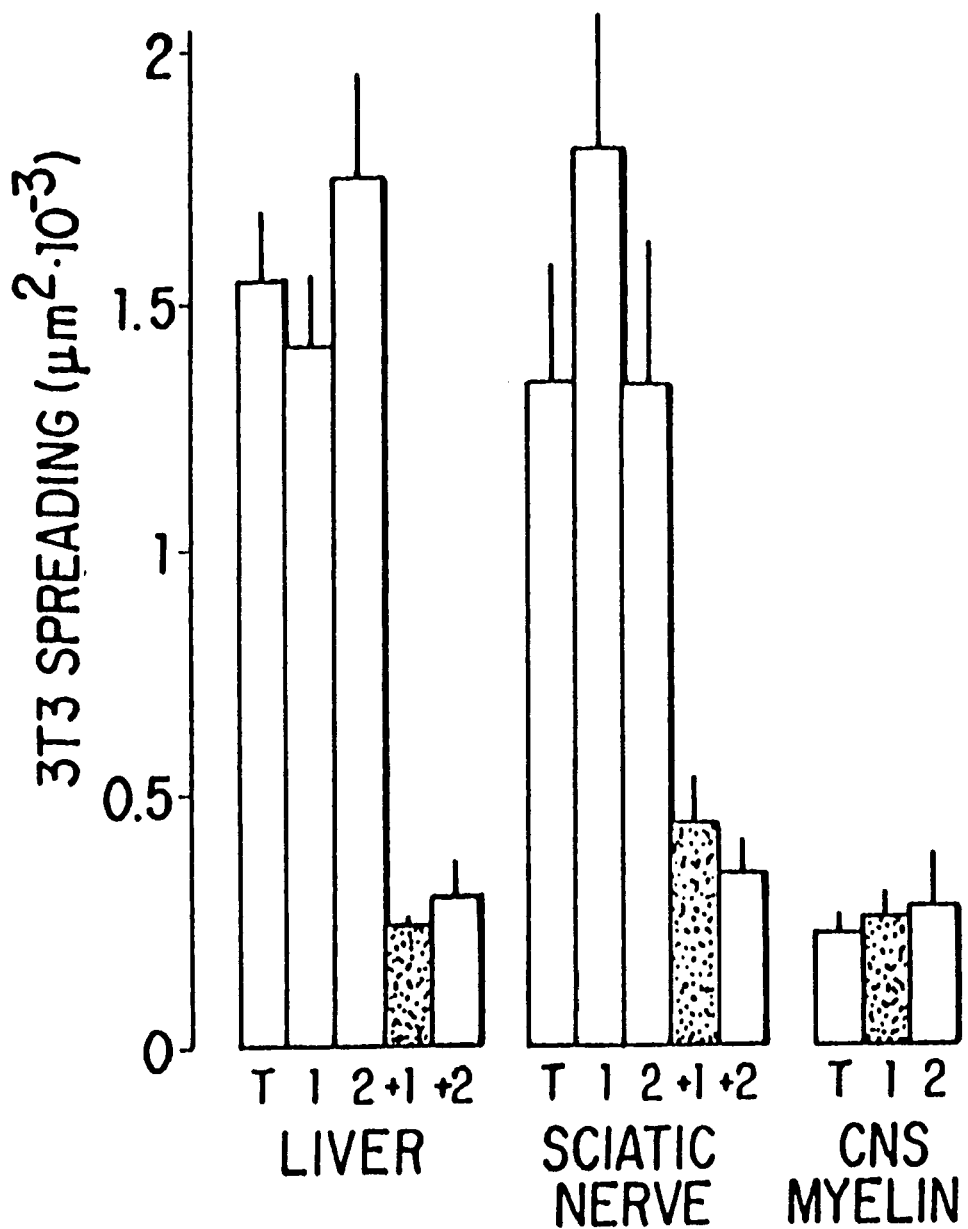
Figure 13A:
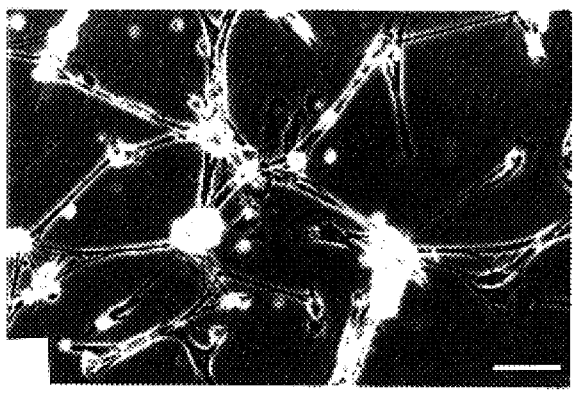
Figure 13B:
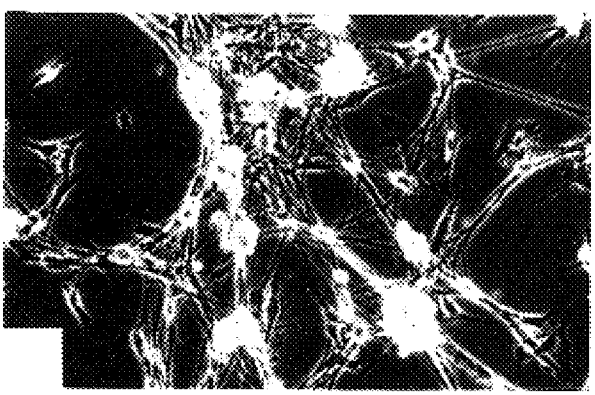
Figure 13C:
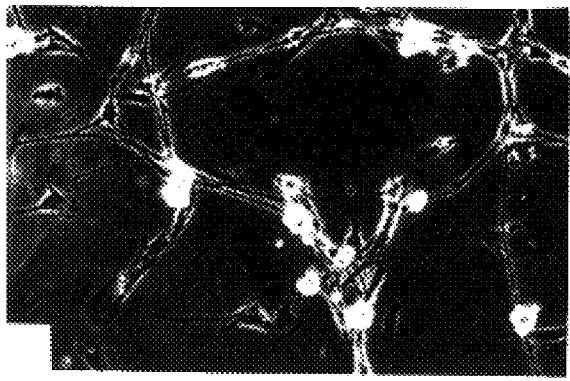
Figure 13D:
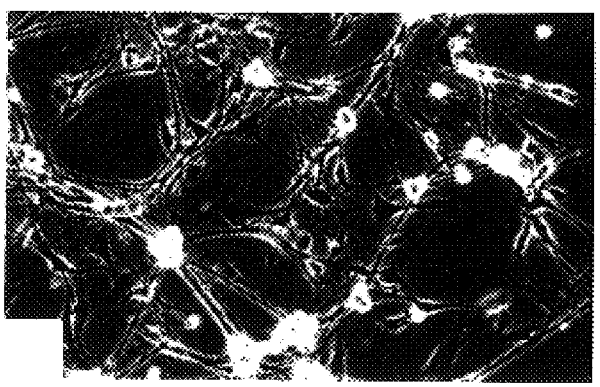
Figure 13E:
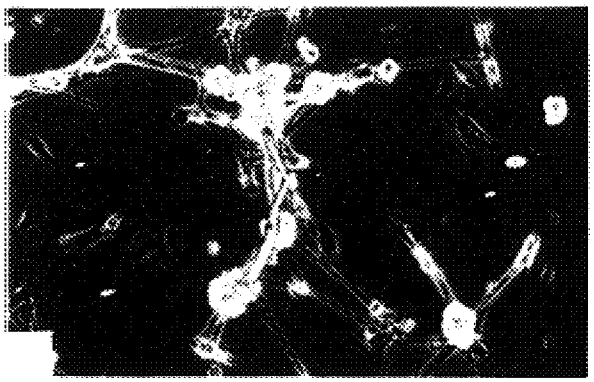
Figure 13F:
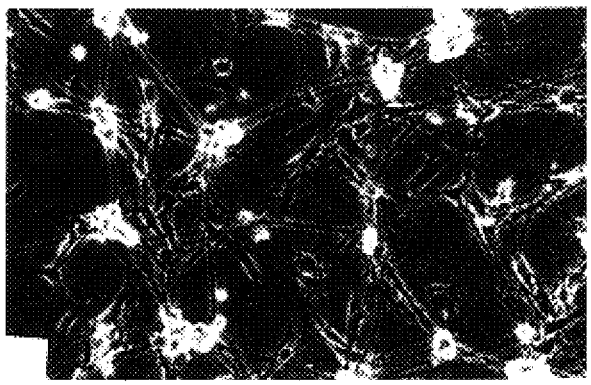
Figure 13G:
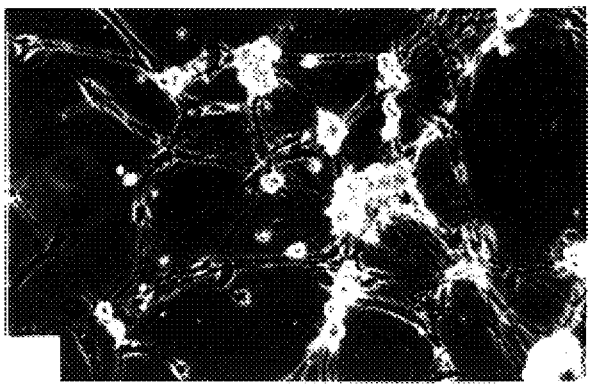
Figure 13H:
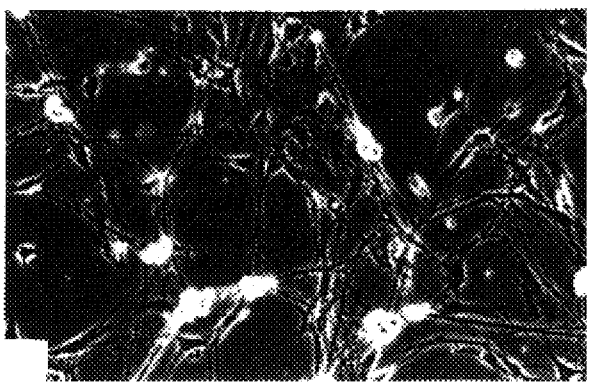
Figure 14A:
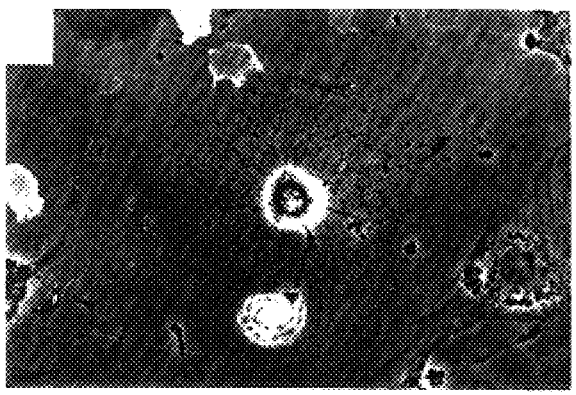
Figure 14B:
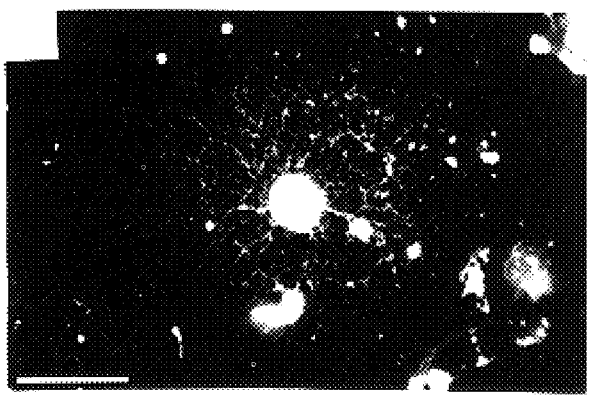
Figure 14C:
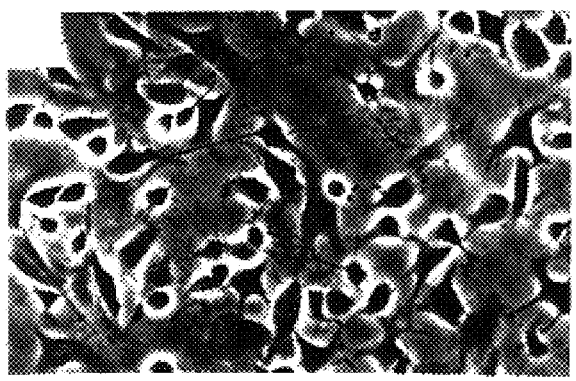
Figure 14D:
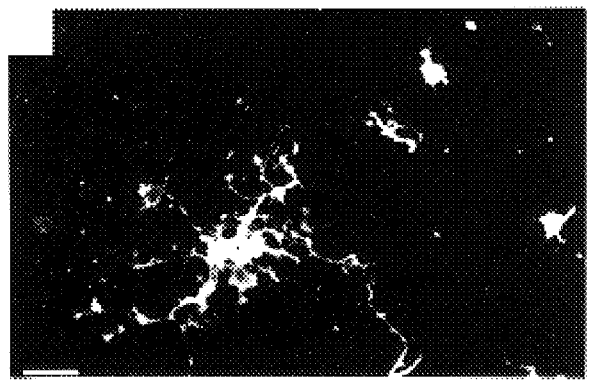
Figure 14E:
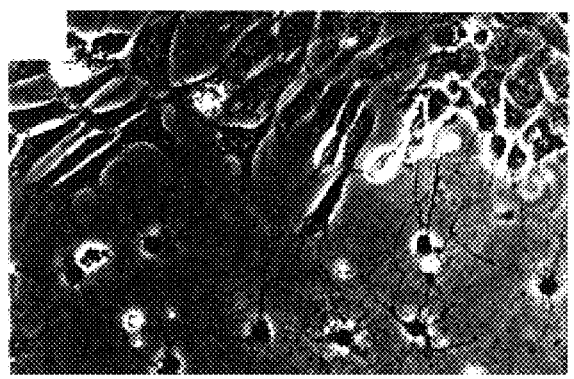
Figure 14F:
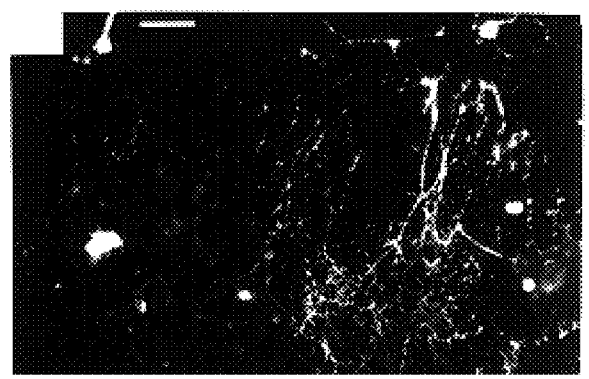

FIG. 12. 35 kD and 250 kD protein fractions from rat CNS myelin convert permissive substrates into nonpermissive substrates. Total protein (T) liposomes were formed with 100 µg of protein from each of the three sources (rat) indicated in the figure. (1) (250 kD) and (2) (35 kD) liposomes were formed with gel-extracted protein regions from 3–15% gels loaded with 500 µg protein from the same three sources. Columns labeled +1 and +2 indicate that 250 kD (1) or 35 kD (2) protein from 500 µg of rat CNS myelin were combined with 100 µg of total liver or PNS myelin protein before reconstitution.

FIGS. 13A–H. Nonpermissive substrate properties of CNS myelin and of 35 kD and 250 kD inhibitors were neutralized by monoclonal antibody IN-1. SCG neurons were cultivated on test substrates in the absence (A, C, E, and G) or the presence (B, D, F, and H) of monoclonal antibody IN-1. Cultures were photographed after 24 hours. Substrate-adsorbed wells of Greiner dishes were preincubated in the presence of hybridoma medium or IN-1 hybridoma supernatant for 30 minutes, four-fifths of the preincubation medium was then removed, and SCG neurons were added, thus replacing the removed quantity of medium. Well-adsorbed substrates were as follows: CNS myelin membranes (A and B), 250 kD inhibitor-containing liposomes (C and D), 35 kd inhibitor-containing liposomes (E and F), and liposomes containing permissive 250 kD protein fraction from rat PNS myelin (G and H). Bar, 50 µm.

FIGS. 14A–F. Monoclonal antibody IN-1 binds to the surface of HBOs and neutralizes their nonpermissive substrate properties. Two day old optic nerve cultures were either stained with IN-1 (B) or tested as substrates for 3T3 cell spreading in the presence (C,D) and absence (E,F) of IN-1. IN-1 specifically bound to the surface of HBOs (A, phase contrast; B, immunofluorescence with antibody IN-1). Frequent fibroblast spreading over HBO territories was observed when IN-1 was present in the incubation medium (C, phase contrast; D, immunofluorescence with $O_1$; cells were fixed 2 hours after the addition of 3T3 fibroblasts with fixation media containing 4% paraformaldehyde before incubation with antibody $O_1$), whereas fibroblasts did not invade the territory of HOs in the presence of control monoclonal antibody $O_1$ (E, phase contrast; F, immunofluorescence with $O_1$). In the control experiment of (E), cells were fixed 10 hours after fibroblast addition to show attachment of HBO processes to 3T3 cells; numerous $O_1^+$ processes were observed connecting oligodendrocyte and fibroblast cell bodies. Bar, 50 µm.

Figure 15:
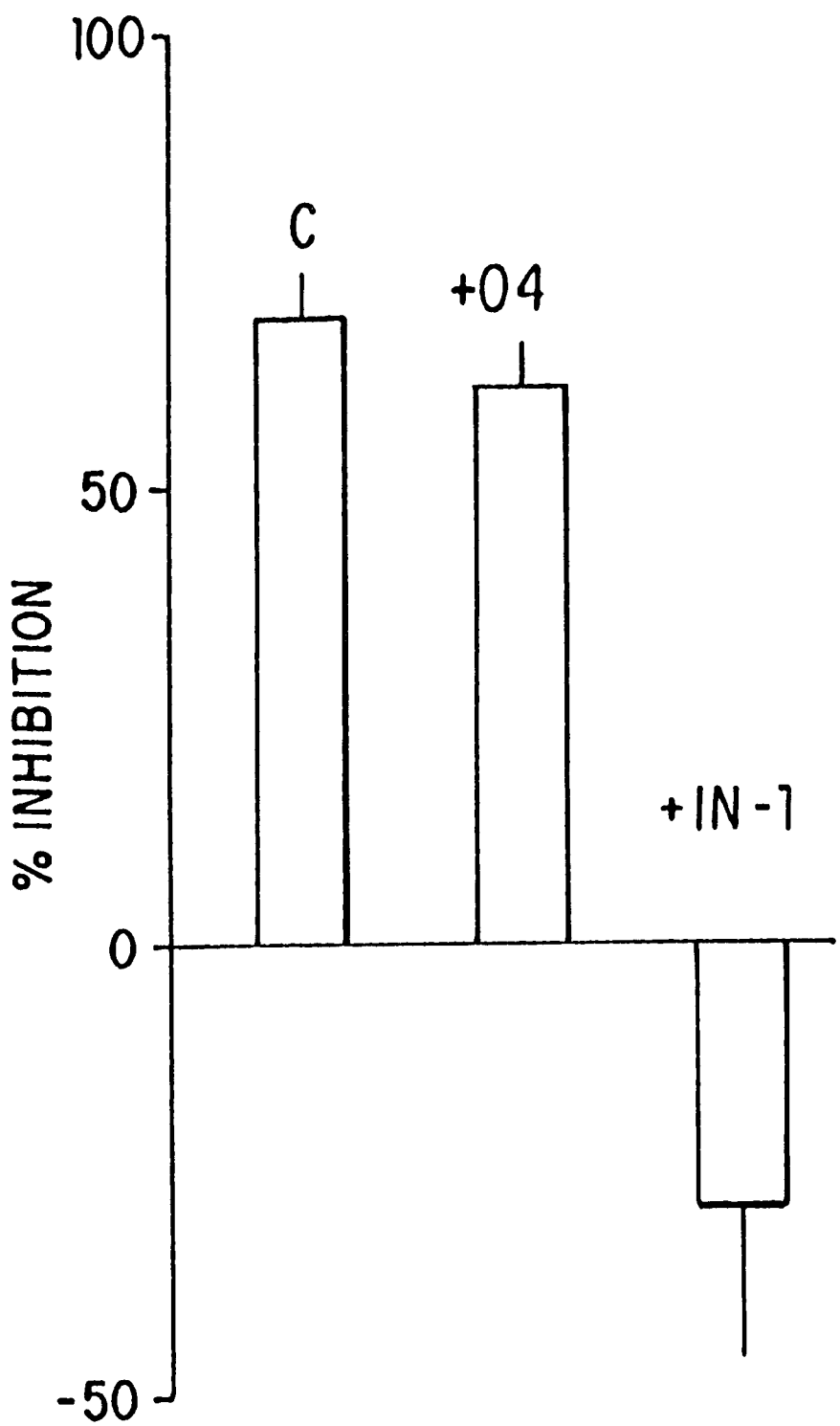

FIG. 15. Quantitative determination of IN-1-mediated neutralization of HBO nonpermissive substrate properties. 3T3 cells were added to 2 day old optic nerve cultures in the presence of either hybridoma medium (C), monoclonal antibody $O_4$ or antibody IN-1. Cultures were fixed after 2 hours, and oligodendrocytes were identified by $O_1$ staining. Preferential adhesion and spreading of 3T3 cells on a polylysine-coated culture dish and on the surface of $O_1^+$ HBOs were determined as-described infra in Section 8.1.4. A value of 100% inhibition represents no overlap of 3T3 cell surfaces with $O_1^+$ surfaces; 0% inhibition represents no apparent discrimination by 3T3 cells between the polylysine-coated culture dish and HBO surface; negative inhibition values indicate that the fraction of HBO surfaces covered by 3T3 cells was larger than the fraction of the entire culture surface covered by 3T3 cells, i.e., 3T3 cells preferentially spread on HBOs. Values are means±SEM. Twenty separate determinations from two independent experiments were analyzed.

Figure 16:
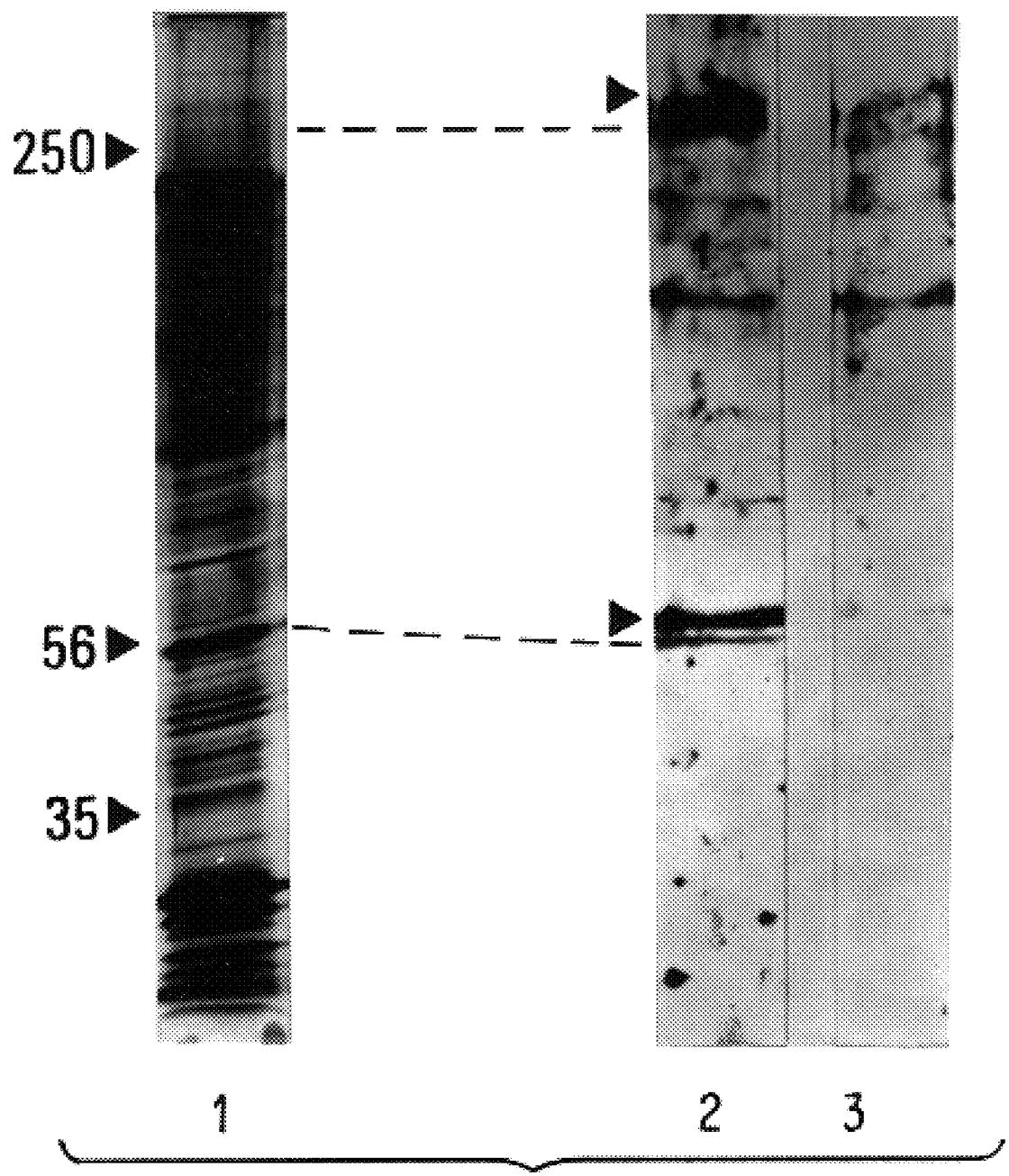

FIG. 16. Immunoblot of rat CNS myelin protein with monoclonal antibody IN-1. CNS myelin protein was separated by 3–15% SDS-PAGE under reducing conditions. Lane 1, silver-stained gel of rat CNS myelin protein; the positions of the inhibitory protein regions are indicated by arrowheads. Lanes 2 and 3, immunoblot with IN-1 (lane 2) or control antibody against horseradish peroxidase (lane 3). Lane 1 and lanes 2 and 3 are from two different gels. The approximate migration position of protein bands giving specific IN-1+ signals are indicated by arrowheads (lanes 1 and 2). IN-1 binding to protein bands in the 35 kd region was variable, weak, and not detectable on the immunoblot shown.

Figure 17A:
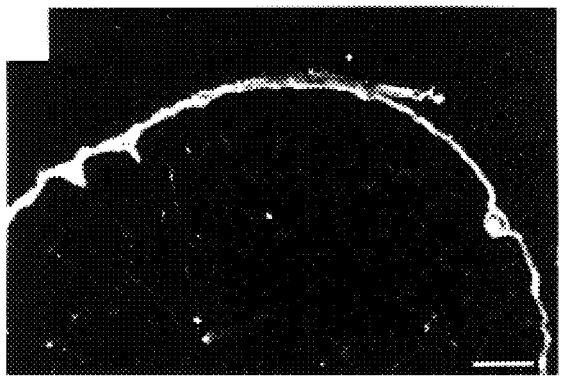
Figure 17B:
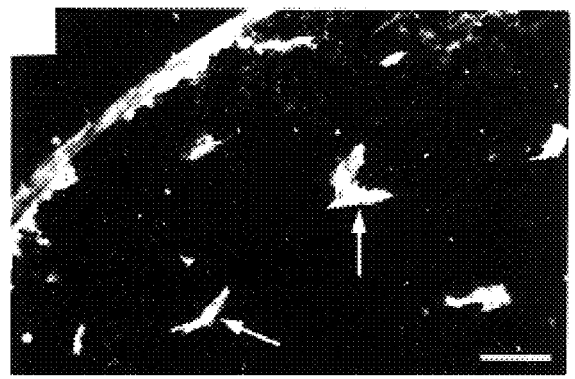

FIGS. 17A–B. Laminin immunoreactivity in adult optic nerve in vivo and in cultured optic nerve explants. In the in vivo nerve, only subpial and perivascular basement membranes showed specific laminin immunoreactivity (A). In cultured optic nerve explants (chamber culture, 4 weeks in vitro), strongly laminin-positive cells, presumably astrocytes (arrows), appeared inside the explant (B). Bar, 50 μm.

Figure 18A:
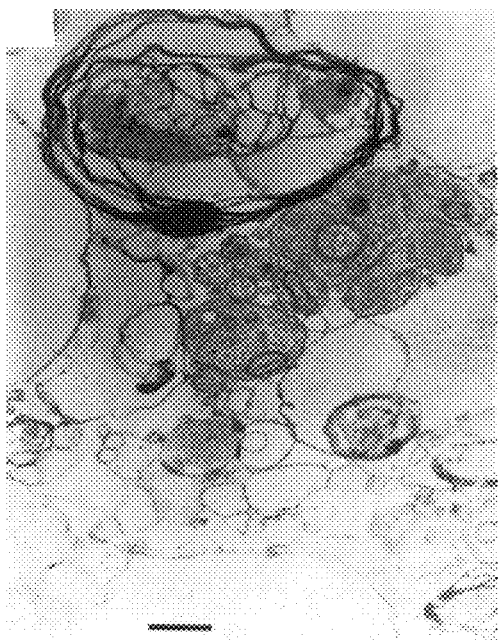
Figure 18B:

FIGS. 18A–B. Sensory axons in IN-1-injected nerve explants. Electron micrographs from representative experiments as described in Table X. (A) Electron micrograph of IN-1-injected optic nerve 1 mm from the proximal stump; an axon bundle growing in direct contact with the myelin is shown. (B) In the presence of IN-1, numerous axons grew 3 mm into the optic nerve explant. Bar, 0.5 μm.

FIGS. 19A–D. C6, but not 3T3 cells, infiltrate optic nerve explants. Phase-contrast microphotographs of μm frozen sections of rat optic (A,B) or sciatic (C,D) nerve explants, after 2 weeks incubation with C6 (A,C) or 3T3 (B,D) cells. Cells were added to one tip of the explants. Infiltrated cells can be seen after cresyl violet staining in both sciatic nerves (C,D) but only for C6 cells in the optic nerve (A). Arrows in (B) point to few 3T3 cells adjacent to blood vessels. Bar, 0.2 mm.

FIGS. 20A–F. C6, but not 3T3 or B16 cells attach and spread on CNS white matter of rat cerebellar frozen sections. Phase contrast micrographs of rat cerebellar frozen sections (25 μm) on which C6 (a,b), 3T3 (c,d) or B16 (e) cells were cultured for 2 days. A clear difference on white matter (wm) emerges for 3T3 and B16 cells compared to C6 cells. gl: granular layer, ml: molecular layer. Gray matter is composed of granular and molecular layer. Bar, 0.3 mm.

Figure 21A:
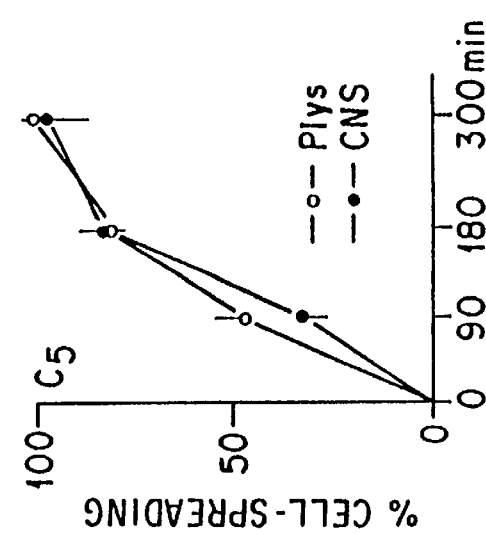
Figure 21B:
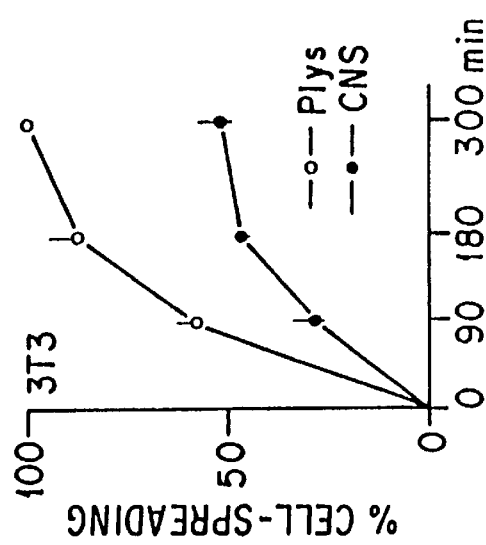
Figure 21C:
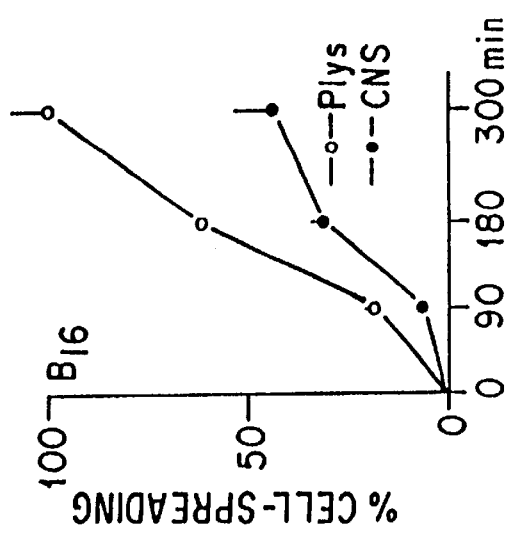

FIGS. 21A–C. C6 cells overcome the inhibitory substrate property of CNS myelin. Spreading of C6 (A), 3T3 (B) and B16 (C) cells on PLYS or CNS myelin. Spreading is calculated as described in Section 9.1.3., infra using electron micrographs. 0% spreading: round cells; 100% spreading was taken as the average value at 300 minutes.

Figure 22:
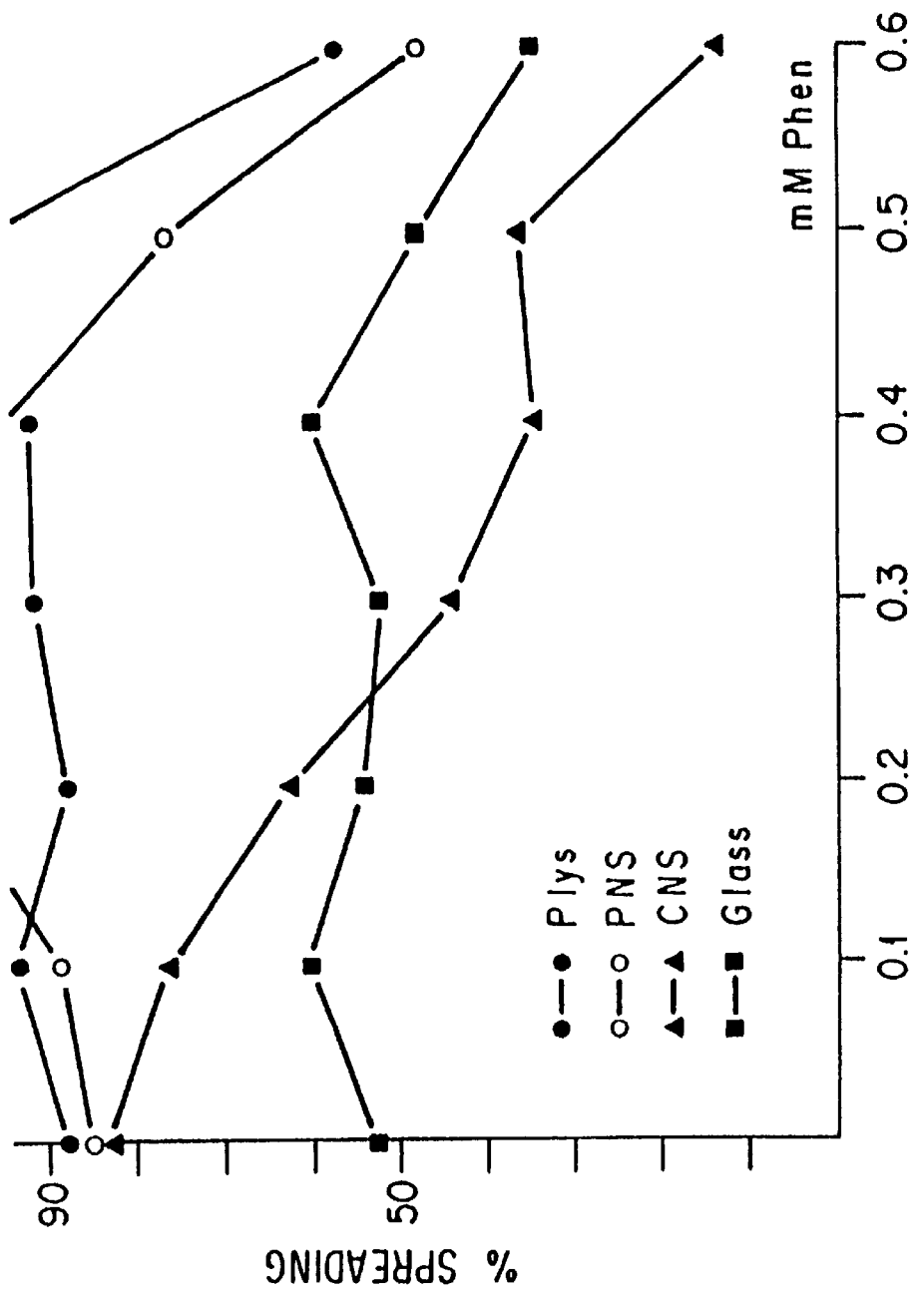
Figure 23A:
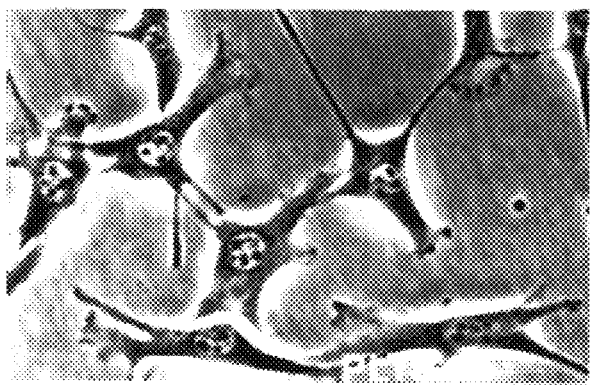
Figure 23B:
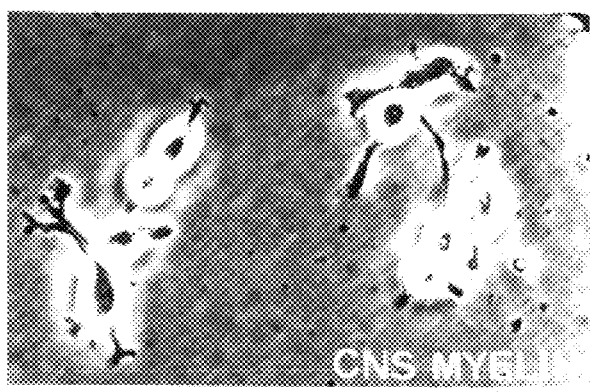
Figure 23C:
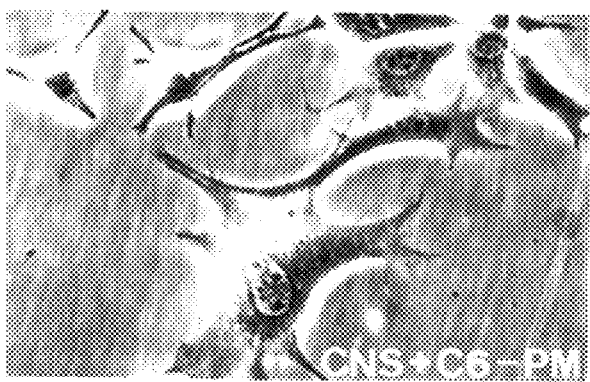
Figure 23D:
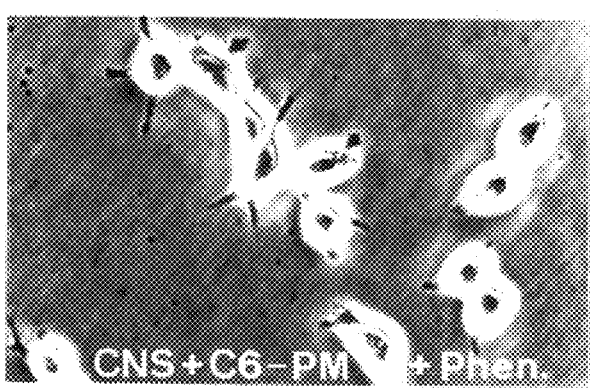

FIG. 22. 1,10-phenanthroline inhibits C6 spreading specifically on CNS myelin. C6 cells were cultured for 3 hours on the indicated substrates in the presence of increasing doses of 1,10-phenanthroline. Spreading was inhibited by low doses exclusively on CNS myelin. 1,10-phenanthroline concentrations above 0.5 mM exert a general toxic effect on all substrates. Spreading was quantified as indicated in FIG. 21.

FIGS. 23A–D. Degradation of CNS inhibitory substrate by C6 plasma membranes is 1,10-phenanthroline sensitive. Spreading of 3T3 cells on CNS myelin was induced by pretreatment of myelin with C6 plasma membranes. 1,10-phenanthroline abolished this effect. Shown are phase contrast micrographs of 3T3 cells on polylysine (PLYS) (23A), on CNS myelin (23B), on CNS myelin pretreated with C6 plasma membranes, and on CNS myelin pretreated with C6 plasma membranes (C6-PM) (23C) in the presence of 1,10-phenanthroline (23D).

FIGS. 24A–B. C6 cell attachment and spreading on CNS white matter of rat cerebellar frozen section is impaired by metalloprotease blockers. Phase contrast micrographs of C6 cells on rat cerebellar frozen sections cultivated in the presence of either 0.1 mM cbz-ala-phe (a) or 0.1 mM cbz-tyr-tyr (b). Inhibition of attachment and spreading is particularly evident in the center of the white matter (asterisks), but is also visible in the main white matter branches (arrows).

Figure 25:
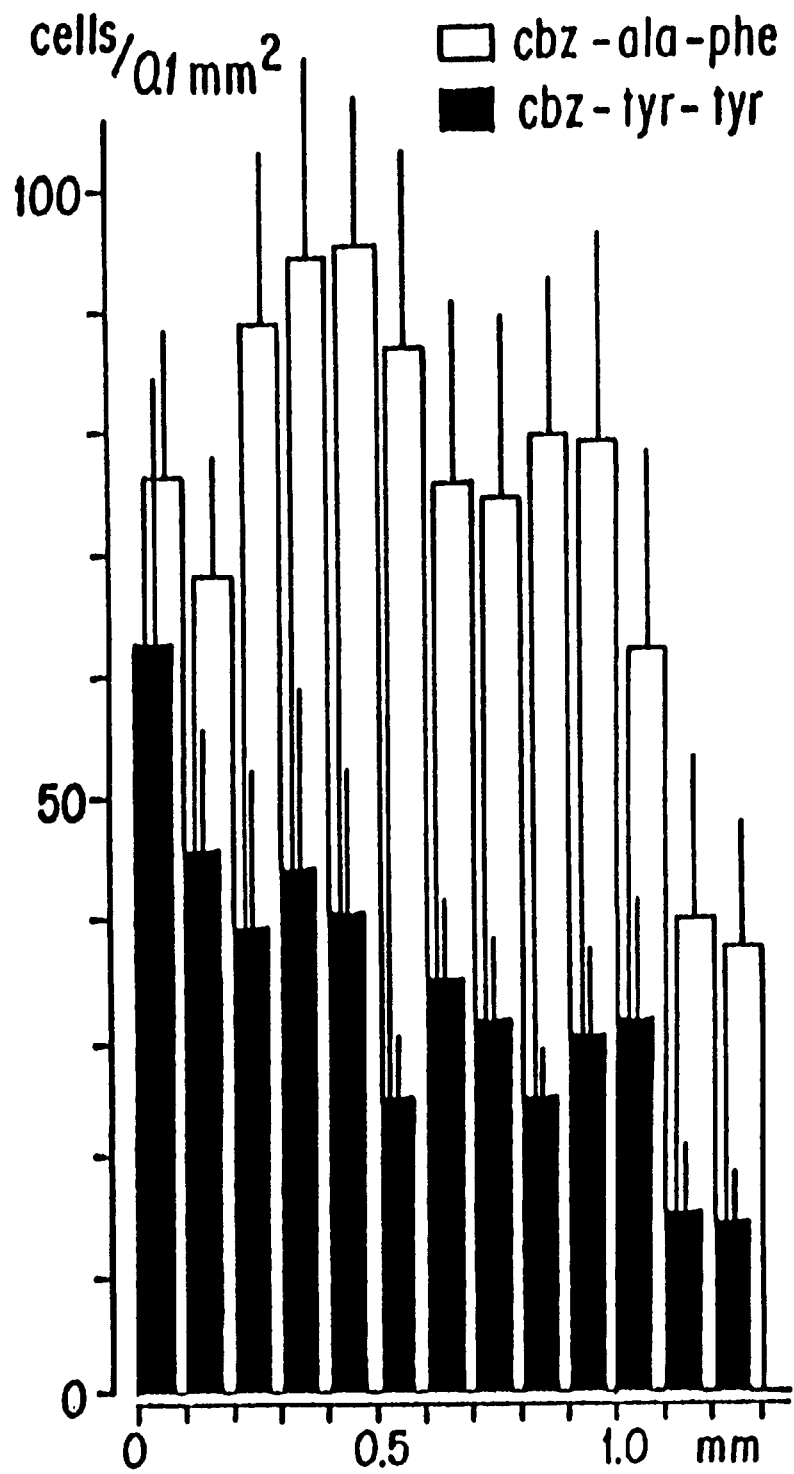

FIG. 25. C6 cell infiltration into CNS explants is impaired by cbz-tyr-tyr. Cells were added to one tip of optic nerve explants (chamber cultures) in the presence of the metalloprotease inhibitor cbz-tyr-tyr, or of the control peptide cbz-ala-phe 14 day old cultures were quantified. Infiltrated cells were counted in the first 1.3 mm of the explants. Each column represents the number of infiltrated cells per 0.1 mm. Only the most central part of the explants was considered (0.25 mm). Values represent means±SEM of two sets of experiments for a total of 8 explants.

Figure 26A:
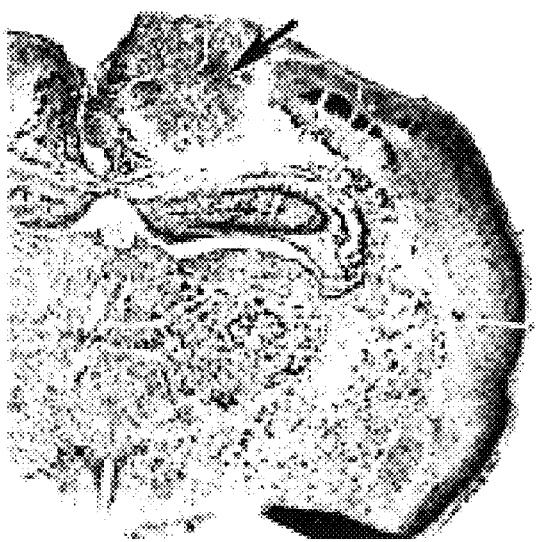
Figure 26B:
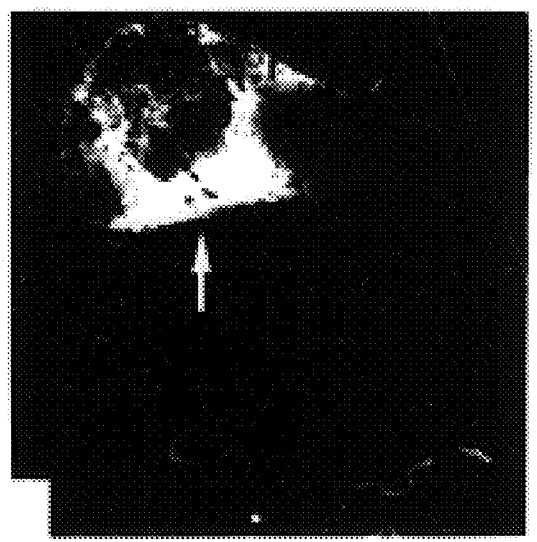

FIGS. 26A–B. Tumor of antibody-secreting mouse IN-1 hybridoma cells in the cortex of an 8 day old rat. 1 mio. cells (in 2 μl) were injected at P2; (A) Cresyl violet stained frozen section (15 μl) shows well circumscribed, compact tumor (arrow); (B) Antibody production demonstrated by immunofluorescence with anti-mouse-Ig-FITC. Tumor and surrounding tissue up to the lateral ventricle (small arrow) are strongly stained (adjacent section to A). Rat was fixed by perfusion with 4% formaldehyde in phosphate buffer. Magnification: 6.4×

Figure 27:
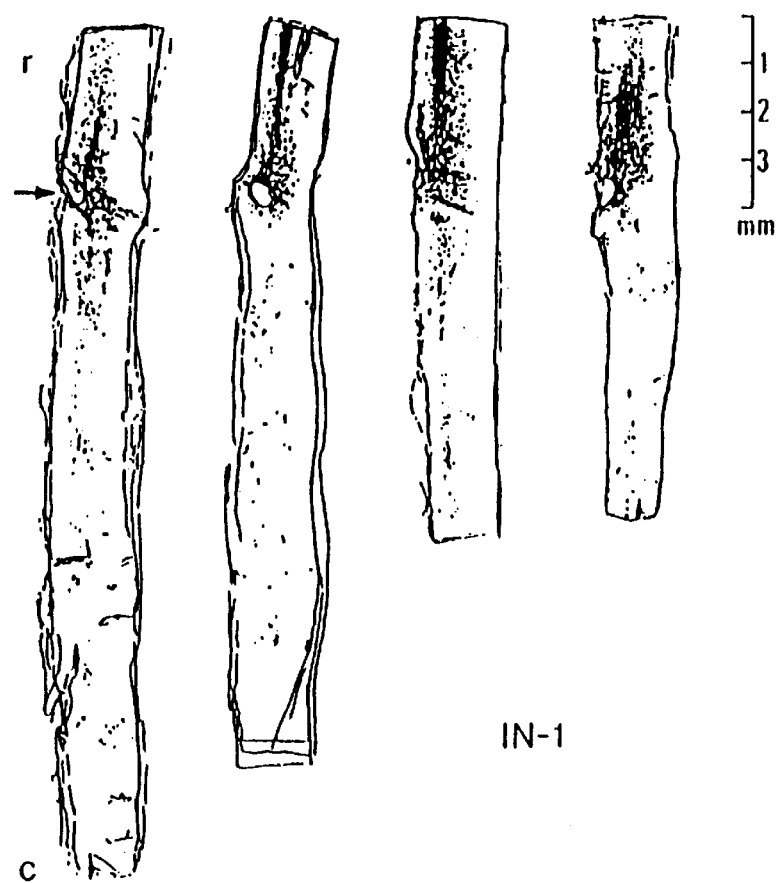
Figure 27:
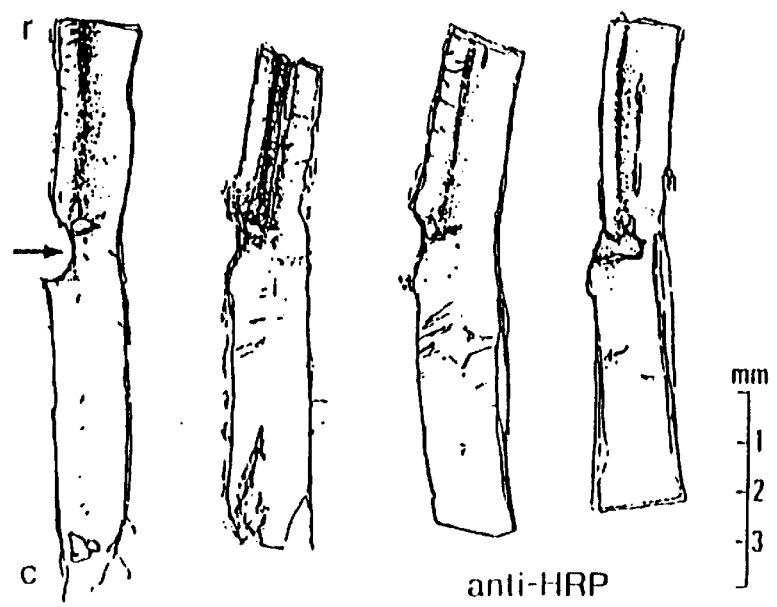

FIG. 27. Labelled corticospinal tract fibers are present far distal to spinal cord lesions in 4 IN-1 treated rats (top), but not in 4 control anti-HRP treated animals (bottom). Camera lucida drawings of longitudinal sections of spinal cords (75μ total thickness, 3 superimposed 25μ sections) showing labelling pattern of CST fibers labelled by anterograde transport of WGA-HRP. Long-distance elongation of regeneration CST fibers is present in the IN-1 treated rats. Arrow points to lesion sites, which sometimes contain small caverns communicating with the central canal.—r: rostral; c: caudal.

Figure 28:
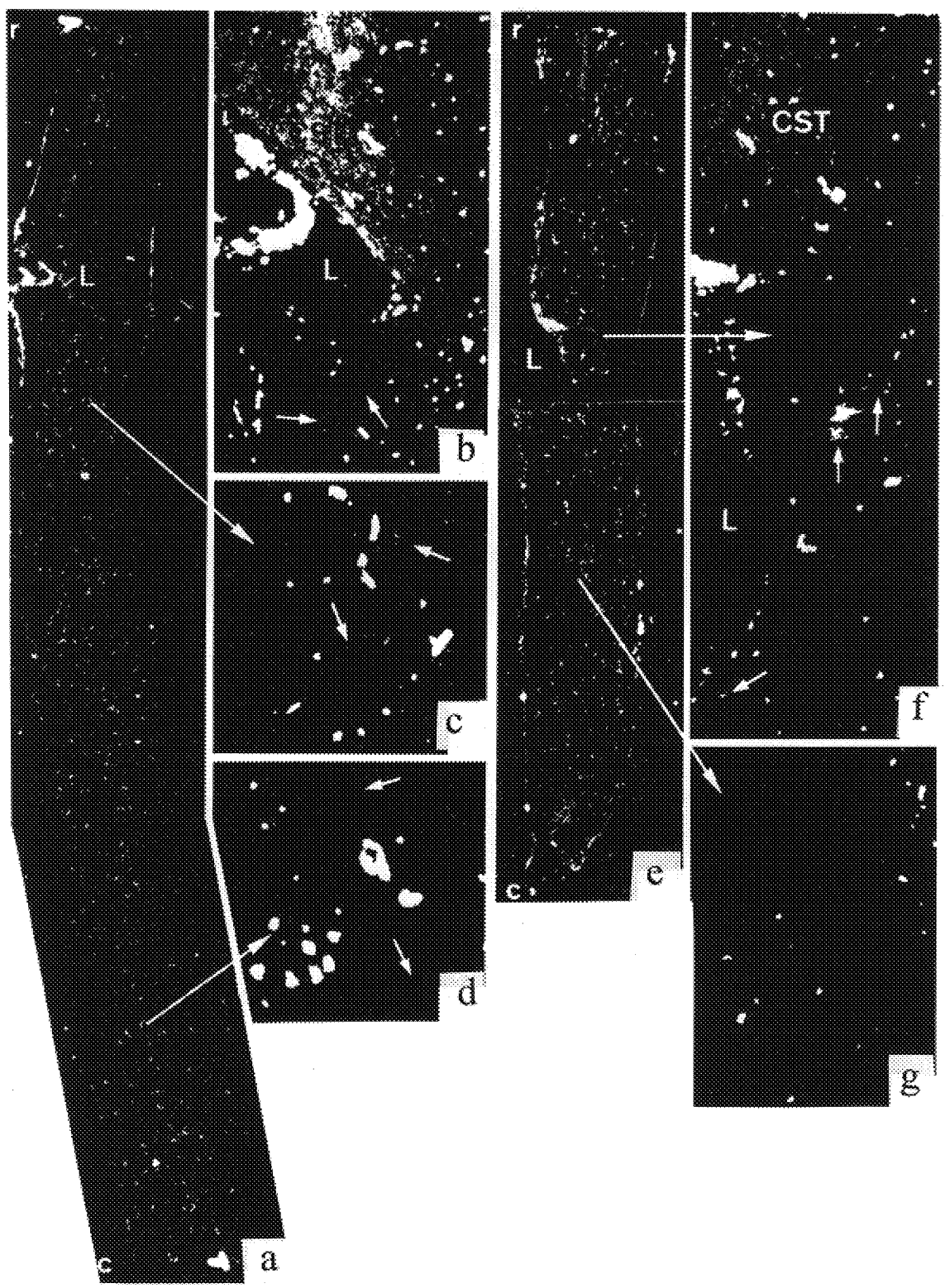

FIG. 28. Dark-field micrographs of spinal cord longitudinal sections of an IN-treated rat (A–D) and an anti-HRP-treated rat (E–G). high magnification micrographs show the densely labelled CST with a broad sprouting zone rostral to the lesion (B and F). Fine grain specific label (arrows) is seen immediately caudal to the lesion in both animals (B, F). Label is also present far distal (about 7 mm) in the IN-treated spinal cord (C,D). In contrast, no such label was detectable in the anti-HRP-treated rat (G).

Large white dots (crystals) in all sections represent reaction product in blood vessels, always prominant in material reated with this highly sensitive procedure. c=caudal; L=lesion; r=rostral.

Magnification: A,E: 14×; B,F,G: 70×; C,D: 140×.

5. DETAILED DESCRIPTION OF THE INVENTION

The present invention is directed to genes and their encoded proteins which regulate neurite growth and the diagnostic and therapeutic uses of such proteins. The proteins of the present invention (termed herein neurite growth regulatory factors) include proteins associated with central nervous system myelin with highly nonpermissive substrate properties, termed herein neurite growth inhibitory factors. The neurite growth regulatory factors also include metalloproteases which can be found associated with malignant tumors, in particular, those tumors metastatic to the brain.

The CNS myelin associated proteins of the invention inhibit neurite outgrowth in nerve cells or neuroblastoma cells. The protein can also inhibit fibroblast spreading and migration. These inhibitory proteins are active cross-species and may be used in the treatment of patients with malignant tumors including but not limited to melanoma and tumors of nerve tissue (e.g. neuroblastoma). In a specific example of the present invention, a 35 kilodalton and a 250 kilodalton CNS myelin associated protein are described.

The present invention is also directed to antibodies to the CNS myelin associated proteins and their therapeutic and diagnostic uses. These antibodies can be used in the treatment of nerve damage resulting from, e.g., trauma (e.g., spinal cord injuries), stroke, degenerative disorders of the central nervous system, etc. In particular, antibodies to CNS myelin associated proteins may be used to promote regeneration of nerve fibers. In a specific embodiment of the invention, monoclonal antibody IN-1 may be used to promote the regeneration of nerve fibers over long distances following spinal cord damage.

The present invention further relates to neurite growth regulatory factor receptors and peptide fragments thereof as well as the nucleic acid sequences coding for neurite growth regulatory factor receptors and fragments, and their therapeutic and diagnostic uses. Antibodies to neurite growth regulatory factor receptors are also envisioned and within the scope of the present invention.

The present invention is also directed to metalloproteases associated with malignant tumors, in particular, those metastatic to the brain. In a specific embodiment, the metalloprotease is associated with glioblastoma cells. The metalloproteases of the invention are associated with the CNS infiltration activity of malignant cells, and can neutralize the inhibitory substrate properties of the CNS myelin-associated proteins. The metalloproteases can have therapeutic value in the treatment of nerve damage such as that resulting from traumatic injury (e.g. spinal cord injuries), stroke, degenerative disorders of the central nervous system, etc. Alternatively, the metalloprotease may be used in combination with antibodies directed against myelin associated inhibitory proteins to treat nerve damage.

The present invention is also directed to inhibitors of the metalloproteases. Such inhibitors can impair malignant cell spreading and infiltration, and can be used in the treatment of malignant tumors (e.g. glioblastoma). In a specific embodiment, the metalloprotease inhibitors in combination with CNS myelin associated inhibitory proteins such as the 35,000 dalton and/or the 250,000 dalton molecular weight proteins or human functional equivalents thereof, may be used in the diagnosis and/or treatment of malignant tumors which include but are not limited to glioblastomas, neuroblastomas, and melanomas.

The method of the invention can be divided into the following stages, solely for the purpose of description: (1) isolation and purification of neurite growth regulatory factors; (2) characterization of neurite growth regulatory factors; (3) molecular cloning of genes or gene fragment encoding neurite growth regulatory factors; (4) production of antibodies against neurite growth regulatory factors; and (5) generation of neurite growth regulatory factor related derivatives, analogs, and peptides. The method further encompasses the diagnostic and therapeutic uses of neurite growth regulatory factors and their antibodies.

5.1. ISOLATION AND PURIFICATION OF NEURITE GROWTH REGULATORY FACTORS

The present invention relates to CNS myelin associated inhibitory proteins of neurite growth, receptors of CNS myelin associated inhibitory proteins of neurite growth, and to metalloproteases such as that associated with membranes of glioblastoma cells. The CNS myelin associated inhibitory proteins of the invention may be isolated by first isolating myelin and subsequent purification therefrom. Similarly, the metalloprotease may be obtained by isolation from mammalian glioblastoma cells. Isolation procedures which may be employed are described more fully in the sections which follow. Alternatively, the CNS myelin associated inhibitory proteins or the metalloprotease may be obtained from a recombinant expression system (see Section 5.3., infra). Procedures for the isolation and purification of receptors for the CNS myelin associated inhibitory proteins are described in Section 5.1.2., infra.

5.1.1. ISOLATION AND PURIFICATION OF CNS MYELIN ASSOCIATED INHIBITORY PROTEINS

CNS myelin associated inhibitory proteins can be isolated from the CNS myelin of higher vertebrates including, but not limited to, birds or mammals. Myelin can be obtained from the optic nerve or from central nervous system tissue that includes but is not limited to spinal cords or brain stems. The tissue may be homogenized using procedures described in the art (Colman et al., 1982, J. Cell Biol. 95:598–608). The myelin fraction can be isolated subsequently also using procedures described (Colman et al., 1982, supra).

In one embodiment of the invention, the CNS myelin associated inhibitory proteins can be solubilized in detergent (e.g., Nonidet P-40™, sodium deoxycholate). The solubilized proteins can subsequently be purified by various procedures known in the art, including but not limited to chromatography (e.g., ion exchange, affinity, and sizing chromatography), centrifugation, electrophoretic procedures, differential solubility, or by any other standard technique for the purification of proteins (see, e.g., Section 7.2.3., infra).

Alternatively, the CNS myelin associated inhibitory proteins may be isolated and purified using immunological procedures. For example, in one embodiment of the invention, the proteins can first be solubilized using detergent (e.g., Nonidet P-40™, sodium deoxycholate). The proteins may then be isolated by immunoprecipitation with antibodies to the 35 kilodalton and/or the 250 kilodalton proteins. Alternatively, the CNS myelin associated inhibitory proteins may be isolated using immunoaffinity chromatography in which the proteins are applied to an antibody column in solubilized form.

5.1.2. ISOLATION AND PURIFICATION OF RECEPTORS FOR THE CNS MYELIN ASSOCIATED INHIBITORY PROTEINS

Receptors for the CNS myelin associated inhibitory proteins can be isolated from cells whose attachment, spreading, growth and/or motility is inhibited by the CNS myelin associated inhibitory proteins. Such cells include but are not limited to fibroblasts and neurons. In a preferred embodiment, fibroblasts are used as the source for isolation and purification of the receptors.

In one embodiment, receptors to CNS myelin associated inhibitory proteins may be isolated by affinity chromatography of fibroblast cell extracts, in which a myelin associated inhibitory protein or peptide fragment thereof is immobilized to a solid support.

5.1.3. ISOLATION AND PURIFICATION OF METALLOPROTEASES ASSOCIATED WITH MALIGNANT TUMORS

The metalloproteases of the present invention may be isolated from cells of malignant tumors, in particular, those tumors which can metastasize to the brain. In a preferred embodiment, a metalloprotease can be isolated from mammalian glioblastoma cells. In a preferred method, the metalloprotease is isolated from the plasma membrane fraction of such cells. The cells may be obtained by dissociating and homogenizing tumors using procedures known in the art or from tumor cell lines. Plasma membrane fractions may be obtained using procedures known in the art, e.g., gradient centrifugation (Quigley, 1976, J. Cell Biol. 71:472–486). The metalloprotease may be isolated from the membranes by solubilization with mild ionic or nonionic detergent (e.g., deoxycholate, Nonidet P-40™, Triton™, Brij™) using procedures described in the art (reviewed in Cooper, 1977, In Tools of Biochemistry, John Wiley & Sons, NY, pp. 355–406).

Purification of the metalloprotease can be carried out by known procedures, including but not limited to chromatography (e.g., ion exchange, affinity, and sizing column chromatography), centrifugation, electrophoretic procedures, differential solubility, or by any other standard technique for the purification of proteins.

5.2. PROTEIN CHARACTERIZATION

The neurite growth regulatory factors of the present invention can be analyzed by assays based on their physical, immunological, or functional properties. The half life of the neurite growth regulatory factors in cultured cells can be studied, for example, by use of cycloheximide, an inhibitor of protein synthesis (Vasquez, 1974, FEBS Lett. 40:563–584). In other experiments, a physiological receptor for a neurite growth regulatory factor could be identified by assays which detect complex formation with a neurite growth regulatory factor, e.g., by use of affinity chromatography with immobilized neurite growth regulatory factor, binding to a labeled neurite growth regulatory factor followed by cross-linking and immunoprecipitation, etc.

Electrophoretic techniques such as SDS-polyacrylamide gel electrophoresis and two-dimensional electrophoresis can be used to study protein structure. Other techniques which can be used include but are not limited to peptide mapping, isoelectric focusing, and chromatographic techniques.

The amino acid sequences of primary myelin associated inhibitors or of the metalloprotease can be derived by deduction from the DNA sequence if such is available, or alternatively, by direct sequencing of the protein, e.g., with an automated amino acid sequencer. The protein sequences can be further characterized by a hydrophilicity analysis (Hopp and Woods, 1981, Proc. Natl. Acad. Sci. U.S.A. 78:3824–3828). A hydrophilicity profile can be used to identify the hydrophobic and hydrophilic regions of the protein (and the corresponding regions of the gene sequence, if available, which encode such regions).

Secondary structural analysis (Chou and Fasman, 1974, Biochemistry 13:222) can also be done, to identify regions of the CNS myelin associated inhibitor or gliobastoma metalloprotease sequence that assume specific secondary structures. Other methods of structural analysis can also be employed. These include but are not limited to X-ray crystallography (Engstom, 1974, Biochem. Exp. Biol. 11:7–13) and computer modeling (Fletterick, R. and Zoller, M. (eds.), 1986, Computer Graphics and Molecular Modeling, in Current Communications in Molecular Biology, Cold Spring Harbor Laboratory, Cold Spring Harbor, N.Y.).

5.3. MOLECULAR CLONING OF GENES OR GENE FRAGMENTS ENCODING NEURITE GROWTH REGULATORY FACTORS

5.3.1. ISOLATION AND CLONING OF THE NEURITE GROWTH REGULATORY FACTOR GENES

Any mammalian cell can potentially serve as the nucleic acid source for the molecular cloning of the genes encoding the CNS myelin associated inhibitory proteins, including but not limited to the 35 kD and/or 250 kD myelin associated proteins described in Section 7., infra, or the glioblastoma associated metalloprotease, hereinafter referred to as neurite growth regulatory factor genes.

The DNA may be obtained by standard procedures known in the art from cloned DNA (e.g., a DNA "library"), by chemical synthesis, by cDNA cloning, or by the cloning of genomic DNA, or fragments thereof, purified from the desired mammalian cell. (See, for example, Maniatis et al., 1982, Molecular Cloning: A Laboratory Manual, Cold Spring Harbor Laboratory, Cold Spring Harbor, N.Y.; Glover, D. M. (ed.), 1985, DNA Cloning: A Practical Approach, MRL Press, Ltd., Oxford, U.K., Vol. I, II.) Clones derived from genomic DNA may contain regulatory and intron DNA regions, in addition to coding regions; clones derived from cDNA will contain only exon sequences. Whatever the source, a given neurite growth regulatory factor gene should be molecularly cloned into a suitable vector for propagation of the gene.

In the molecular cloning of a neurite growth regulatory factor gene from genomic DNA, DNA fragments are generated, some of which will encode the desired neurite growth regulatory factor gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing a neurite growth regulatory factor gene may be accomplished in a number of ways. For example, if an amount of a neurite growth regulatory factor gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961–3965). For example, in a preferred embodiment, a portion of a neurite growth regulatory factor amino acid sequence can be used to deduce the DNA sequence, which DNA sequence can then be synthesized as an oligonucleotide for use as a hybridization probe. Alternatively, if a purified neurite growth regulatory factor probe is unavailable, nucleic acid fractions enriched in neurite growth regulatory factor may be used as a probe, as an initial selection procedure.

It is also possible to identify an appropriate neurite growth regulatory factor-encoding fragment by restriction enzyme digestion(s) and comparison of fragment sizes with those expected according to a known restriction map if such is available. Further selection on the basis of the properties of the gene, or the physical, chemical, or immunological properties of its expressed product, as described supra, can be employed after the initial selection.

A neurite growth regulatory factor gene can also be identified by mRNA selection using nucleic acid hybridization followed by in vitro translation or translation in Xenopus oocytes. In an example of the latter procedure, oocytes are injected with total or size fractionated CNS mRNA populations, and the membrane-associated translation products are screened in a functional assay (3T3 cell spreading). Preadsorption of the RNA with complementary DNA (cDNA) pools leading to the absence of expressed inhibitory factors indicates the presence of the desired cDNA. Reduction of pool size will finally lead to isolation of a single cDNA clone. In an alternative procedure, DNA fragments can be used to isolate complementary mRNAs by hybridization. Such DNA fragments may represent available, purified neurite growth regulatory factor DNA, or DNA that has been enriched for neurite growth regulatory factor sequences. Immunoprecipitation analysis or functional assays of the in vitro translation products of the isolated mRNAs identifies the mRNA and, therefore, the cDNA fragments that contain neurite growth regulatory factor sequences. An example of such a functional assay involves an assay for nonpermissiveness in which the effect of the various translation products on the spreading of 3T3 cells on a polylysine coated tissue culture dish is observed (see Section 7.1.2., infra). In addition, specific mRNAs may be selected by adsorption of polysomes isolated from cells to immobilized antibodies specifically directed against a neurite growth regulatory factor protein. A radiolabeled neurite growth regulatory factor cDNA can be synthesized using the selected mRNA (from the adsorbed polysomes) as a template. The radiolabeled mRNA or cDNA may then be used as a probe to identify the neurite growth regulatory factor DNA fragments from among other genomic DNA fragments.

Alternatives to isolating the neurite growth regulatory factor genomic DNA include, but are not limited to, chemically synthesizing the gene sequence itself from a known sequence or making cDNA to the mRNA which encodes the neurite growth regulatory factor gene. Other methods are possible and within the scope of the invention.

The identified and isolated gene or cDNA can then be inserted into an appropriate cloning vector. A large number of vector-host systems known in the art may be used. Possible vectors include, but are not limited to, cosmids, plasmids or modified viruses, but the vector system must be compatible with the host cell used. Such vectors include, but are not limited to, bacteriophages such as lambda derivatives, or plasmids such as pBR322 or pUC plasmid derivatives. Recombinant molecules can be introduced into host cells via transformation, transfection, infection, electroporation, etc.

In an alternative embodiment, the neurite growth regulatory factor gene may be identified and isolated after insertion into a suitable cloning vector, in a "shot gun" approach. Enrichment for a given neurite growth regulatory factor gene, for example, by size fractionation or subtraction of cDNA specific to low neurite growth regulatory factor producers, can be done before insertion into the cloning vector. In another embodiment, DNA may be inserted into an expression vector system, and the recombinant expression vector containing a neurite growth regulatory factor gene may then be detected by functional assays for the neurite growth regulatory factor protein.

The neurite growth regulatory factor gene is inserted into a cloning vector which can be used to transform, transfect, or infect appropriate host cells so that many copies of the gene sequences are generated. This can be accomplished by ligating the DNA fragment into a cloning vector which has complementary-cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and neurite growth regulatory factor gene may be modified by homopolymeric tailing.

Identification of the cloned neurite growth regulatory factor gene can be accomplished in a number of ways based on the properties of the DNA itself, or alternatively, on the physical, immunological, or functional properties of its encoded protein. For example, the DNA itself may be detected by plaque or colony nucleic acid hybridization to labeled probes (Benton, W. and Davis, R., 1977, Science 196:180; Grunstein, M. and Hogness, D., 1975, Proc. Natl. Acad. Sci. U.S.A. 72:3961). Alternatively, the presence of a neurite growth regulatory factor gene may be detected by assays based on properties of its expressed product. For example, cDNA clones, or DNA clones which hybrid-select the proper mRNAs, can be selected which produce a protein that inhibits in vitro neurite outgrowth. If an antibody to a neurite growth regulatory factor is available, a neurite growth regulatory factor protein may be identified by binding of labeled antibody to the putatively neurite growth regulatory factor-synthesizing clones, in an ELISA (enzyme-linked immunosorbent assay)-type procedure.

In specific embodiments, transformation of host cells with recombinant DNA molecules that incorporate an isolated neurite growth regulatory factor gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

If the ultimate goal is to insert the gene into virus expression vectors such as vaccinia virus or adenovirus, the recombinant DNA molecule that incorporates a neurite growth regulatory factor gene can be modified so that the gene is flanked by virus sequences that allow for genetic recombination in cells infected with the virus so that the gene can be inserted into the viral genome.

After the neurite growth regulatory factor DNA-containing clone has been identified, grown, and harvested, its DNA insert may be characterized as described in Section 5.3.4, infra. When the genetic structure of a neurite growth regulatory factor gene is known, it is possible to manipulate the structure for optimal use in the present invention. For example, promoter DNA may be ligated 5' of a neurite growth regulatory factor coding sequence, in addition to or replacement of the native promoter to provide for increased expression of the protein. Many manipulations are possible, and within the scope of the present invention.

5.3.2. EXPRESSION OF THE CLONED NEURITE GROWTH REGULATORY FACTOR GENES

The nucleotide sequence coding for a neurite growth regulatory factor protein or a portion thereof, can be inserted into an appropriate expression vector, i.e., a vector which contains the necessary elements for the transcription and translation of the inserted protein-coding sequence. The necessary transcriptional and translation signals can also be supplied by the native neurite growth regulatory factor gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA, or cosmid DNA. The expression elements of these vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinations (genetic recombination).

Expression vectors containing neurite growth regulatory factor gene inserts can be identified by three general approaches: (a) DNA—DNA hybridization, (b) presence or absence of "marker" gene functions, and (c) expression of inserted sequences. In the first approach, the presence of a foreign gene inserted in an expression vector can be detected by DNA—DNA hybridization using probes comprising sequences that are homologous to an inserted neurite growth regulatory factor gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if a given neurite growth regulatory factor gene is inserted within the marker gene sequence of the vector, recombinants containing the neurite growth regulatory factor insert can be identified by the absence of the marker gene function. In the third approach, recombinant expression vectors can be identified by assaying the foreign gene product expressed by the recombinant. Such assays can be based on the physical, immunological, or functional properties of a given neurite growth regulatory factor gene product.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered neurite growth regulatory factor protein may be controlled. Furthermore, different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian (e.g. COS) cells can be used to ensure "native" glycosylation of the heterologous neurite growth regulatory factor protein. Furthermore, different vector/host expression systems may effect processing reactions such as proteolytic cleavages to different extents.

5.3.3. IDENTIFICATION AND PURIFICATION OF THE EXPRESSED GENE PRODUCT

Once a recombinant which expresses a given neurite growth regulatory factor gene is identified, the gene product can be purified as described in Section 5.1, supra, and analyzed as described in Section 5.2, supra.

The amino acid sequence of a given neurite growth regulatory factor protein can be deduced from the nucleotide sequence of the cloned gene, allowing the protein, or a fragment thereof, to be synthesized by standard chemical methods known in the art (e.g., see Hunkapiller, et al., 1984, Nature 310:105–111).

In particular embodiments of the present invention, such neurite growth regulatory factor proteins, whether produced by recombinant DNA techniques or by chemical synthetic methods, include but are not limited to those containing altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Also included within the scope of the invention are neurite growth regulatory factor proteins which are differentially modified during or after translation, e.g., by glycosylation, proteolytic cleavage, etc.

5.3.4. CHARACTERIZATION OF THE NEURITE, GROWTH REGULATORY FACTOR GENES

The structure of a given neurite growth regulatory factor gene can be analyzed by various methods known in the art.

The cloned DNA or cDNA corresponding to a given neurite growth regulatory factor gene can be analyzed by methods including but not limited to Southern hybridization (Southern, 1975, J. Mol. Biol. 98:503–517), Northern hybridization (Alwine, et al., 1977, Proc. Natl. Acad. Sci. U.S.A. 74:5350–5354; Wahl, et al., 1987, Meth. Enzymol. 152:572–581), restriction endonuclease mapping (Maniatis, et al., 1982, Molecular Cloning, A Laboratory Manual, Cold Spring Harbor Laboratory, Cold Spring Harbor, N.Y.), and DNA sequence analysis.

DNA sequence analysis can be performed by any techniques known in the art including but not limited to the method of Maxam and Gilbert (1980, Meth. Enzymol. 65:499–560), the Sanger dideoxy method (Sanger, et al., 1977, Proc. Natl. Acad. Sci. U.S.A. 74:5463–5467), or use of an automated DNA sequenator (e.g., Applied Biosystems, Foster City, Calif.).

5.4. PRODUCTION OF ANTIBODIES TO NEURITE, GROWTH REGULATORY FACTORS

Antibodies can be produced which recognize neurite growth regulatory factors or related proteins. Such antibodies can be polyclonal or monoclonal.

Various procedures known in the art may be used for the production of polyclonal antibodies to epitopes of a given neurite growth regulatory factor. For the production of antibody, various host animals can be immunized by injection with a neurite growth regulatory factor protein, or a synthetic protein, or fragment thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

A monoclonal antibody to an epitope of a neurite growth regulatory factor can be prepared by using any technique which provides for the production of antibody molecules by continuous cell lines in culture. These include but are not limited to the hybridoma technique originally described by Kohler and Milstein (1975, Nature 256:495–497), and the more recent human B cell hybridoma technique (Kozbor et al., 1983, Immunology Today 4:72) and EBV-hybridoma technique (Cole et al., 1985, Monoclonal Antibodies and Cancer Therapy, Alan R. Liss, Inc., pp. 77–96). In a particular embodiment, the procedure described infra in Section 8.1. may be used to obtain mouse monoclonal antibodies which recognize the 35 kD and 250 kD CNS myelin associated inhibitory proteins.

The monoclonal antibodies for therapeutic use may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

A molecular clone of an antibody to a neurite growth regulatory factor epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

Antibody molecules may be purified by known techniques, e.g., immunoabsorption or immunoaffinity chromatography, chromatographic methods such as HPLC (high performance liquid chromatography), or a combination thereof, etc.

Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the 2 Fab or Fab fragments which can be generated by treating the antibody molecule with papain and a reducing agent.

5.5. NEURITE GROWTH REGULATORY FACTOR-RELATED DERIVATIVES, ANALOGS, AND PEPTIDES

The production and use of derivatives, analogs, and peptides related to a given neurite growth regulatory factor are also envisioned, and within the scope of the present invention and include molecules antagonistic to neurite growth regulatory factors (for example, and not by way of limitation, anti-idiotype antibodies). Such derivatives, analogs, or peptides which have the desired inhibitory activity can be used, for example, in the treatment of neuroblastoma (see Section 5.6, infra). Derivatives, analogs, or peptides related to a neurite growth regulatory factor can be tested for the desired activity by assays for nonpermissive substrate effects. For example, procedures such as the assay for nonpermissiveness in which the effect of the various translation products on the spreading of 3T3 cells on a polylysine coated tissue culture dish is observed (see Section 7.1.2., infra).

The neurite growth regulatory factor-related derivatives, analogs, and peptides of the invention can be produced by various methods known in the art. The manipulations which result in their production can occur at the gene or protein level. For example, a cloned neurite growth regulatory factor gene can be modified by any of numerous strategies known in the art (Maniatis, et al., 1982, Molecular Cloning, A Laboratory Manual, Cold Spring Harbor Laboratory, Cold Spring Harbor, N.Y.). A given neurite growth regulatory factor sequence can be cleaved at appropriate sites with restriction endonuclease(s), subjected to enzymatic modifications if desired, isolated, and ligated in vitro. In the production of a gene encoding a derivative, analogue, or peptide related to a neurite growth regulatory factor, care should be taken to ensure that the modified gene remains within the same translational reading frame as the neurite growth regulatory factor, uninterrupted by translational stop signals, in the gene region where the desired neurite growth regulatory factor-specific activity is encoded.

Additionally, a given neurite growth regulatory factor gene can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, et al., 1978, J. Biol. Chem. 253:6551), use of TABS linkers (Pharmacia), etc.

5.6. USES OF NEURITE GROWTH REGULATORY FACTORS

5.6.1. DIAGNOSTIC USES

5.6.1.1. CNS MYELIN ASSOCIATED INHIBITORY PROTEINS

CNS myelin associated inhibitory proteins, analogs, derivatives, and subsequences thereof, and anti-inhibitory protein antibodies have uses in diagnostics. Such molecules can be used in assays such as immunoassays to detect, prognose, diagnose, or monitor various conditions, diseases, and disorders affecting neurite growth extension, invasiveness, and regeneration. In one embodiment of the invention, these molecules may be used for the diagnosis of malignancies. Alternatively, the CNS myelin associated inhibitory proteins, analogs, derivatives, and subsequences thereof may be used to monitor therapies for diseases and conditions which ultimately result in nerve damage; such diseases and conditions include but are not limited to CNS trauma, (e.g. spinal cord injuries), infarction, infection, malignancy, exposure to toxic agents, nutritional deficiency, paraneoplastic syndromes, and degenerative nerve diseases (including but not limited to Alzheimer's disease, Parkinson's disease, Huntington's Chorea, amyotrophic lateral sclerosis, and progressive supra-nuclear palsy). In a specific embodiment, such molecules may be used to detect an increase in neurite outgrowth as an indicator of CNS fiber regeneration.

For example, in specific embodiments, the absence of the CNS myelin associated inhibitory proteins in a patient sample containing CNS myelin can be a diagnostic marker for the presence of a malignancy, including but not limited to glioblastoma, neuroblastoma, and melanoma, or a condition involving nerve growth, invasiveness, or regeneration in a patient. In a particular embodiment, the absence of the inhibitory proteins can be detected by means of an immunoassay in which the lack of any binding to anti-inhibitory protein antibodies (e.g., IN-1, IN-2) is observed.

The immunoassays which can be used include but are not limited to competitive and non-competitive assay systems using techniques such as radioimmunoassays, ELISA (enzyme linked immunosorbent assay), "sandwich" immunoassays, precipitation reactions, gel diffusion precipitation reactions, immunodiffusion assays, agglutination assays, complement-fixation assays, immunoradiometric assays, fluorescent immunoassays, protein A immunoassays, immunoelectrophoresis assays, and immunohistochemistry on tissue sections, to name but a few.

In a specific embodiment, ligands which bind to a CNS myelin associated inhibitory protein can be used in imaging techniques. For example, small peptides (e.g., inhibitory protein receptor fragments) which bind to the inhibitory proteins, and which are able to penetrate through the blood-brain barrier, when labeled appropriately, can be used for imaging techniques such as PET (positron emission tomography) diagnosis or scintigraphy detection, under conditions noninvasive to the patient.

Neurite growth inhibitory factor genes, DNA, cDNA, and RNA, and related nucleic acid sequences and subsequences, including complementary sequences, can also be used in hybridization assays. The neurite growth inhibitory factor nucleic acid sequences, or subsequences thereof comprising about at least 15 nucleotides, can be used as hybridization probes. Hybridization assays can be used to detect, prognose, diagnose, or monitor conditions, disorders, or disease states associated with changes in neurite growth inhibitory factor expression as described supra. For example, total RNA in myelin, e.g., on biopsy tissue sections, from a patient can be assayed for the presence of neurite growth inhibitory factor mRNA, where the amount of neurite growth inhibitory factor mRNA is indicative of the level of inhibition of neurite outgrowth activity in a given patient.

5.6.1.2. CNS MYELIN ASSOCIATED INHIBITORY PROTEIN RECEPTORS

CNS myelin associated inhibitory protein receptors as well as analogs, derivatives, and subsequences thereof, and anti-receptor antibodies have uses in diagnostics. These molecules of the invention can be used in assays such as immunoassays or binding assays to detect, prognose, diagnose, or monitor various conditions, diseases, and disorders affecting neurite growth, extension, invasion, and regeneration. For example, it is possible that a lower level of expression of these receptors may be detected in various disorders associated with enhanced neurite invasiveness or regeneration such as those involving nerve damage, infarction, degenerative nerve diseases, or malignancies.

The CNS myelin associated inhibitory protein receptors, analogs, derivatives, and subsequences thereof may also be used to monitor therapies for diseases and disorders which ultimately result in nerve damage, which include but are not limited to CNS trauma (e.g. spinal cord injuries), stroke, degenerative nerve diseases, and for malignancies.

The assays which can be used include but are not limited to those described supra in Section 5.6.1.1.

Neurite growth inhibitory factor receptor genes and related nucleic acid sequences and subsequences, including complementary sequences, can also be used in hybridization assays, to detect, prognose, diagnose, or monitor conditions, disorders, or disease states associated with changes in neurite growth inhibitory factor receptor expression.

5.6.1.3. METALLOPROTEASES AND THEIR INHIBITORS

The metalloproteases of the invention, and their analogs, derivatives, and fragments thereof, as well as inhibitors and anti-metalloprotease antibodies, may be used for diagnostic purposes. These molecules of the invention may be used in assays such as immunoassays or inhibition type assays to detect, prognose, diagnose, or monitor various conditions, diseases, and disorders affecting neurite growth extension, invasiveness, or regeneration. In a specific embodiment, the molecules of the present invention can be used to diagnose malignant tumors, in particular, those capable of metastasizing to the brain, (e.g., glioblastoma) by detecting the presence of or an increase in metalloprotease levels. Alternatively, the molecules of the present invention may be used to monitor therapies for malignant tumors such as glioblastoma by detecting changes in metalloprotease levels. In this latter embodiment, decreases or the disappearance of metalloprotease levels should can be indicative of treatment efficacy.

The assays which can be used include but are not limited to those described supra in Section 5.6.1.1.

Metalloprotease genes and related nucleic acid sequences and subsequences, including complementary sequences, can also be used in hybridization assays, to detect, prognose, diagnose, or monitor conditions, disorders, or disease states associated with changes in metalloprotease expression as described supra. For example, total RNA in a sample (e.g., glial cells) from a patient can be assayed for the presence of metalloprotease mRNA, where the presence or amount of metalloprotease mRNA is indicative of a malignancy in the patient. In particular, a malignancy that can be metastatic to the brain (e.g., glioblastoma) can be detected.

5.6.2. THERAPEUTIC USES

5.6.2.1. CNS MYELIN ASSOCIATED INHIBITORY PROTEINS

CNS myelin associated inhibitory proteins of the present invention can be therapeutically useful in the treatment of patients with malignant tumors including, but not limited to melanoma or tumors of nerve tissue (e.g. neuroblastoma). In one embodiment, patients with neuroblastoma can be treated with the 35 kD and/or 250 kD proteins or analogs, derivatives, or subsequences thereof, and the human functional equivalents thereof, which are inhibitors of neurite extension. In another embodiment, a patient can be therapeutically administered both a CNS myelin-associated inhibitory protein and a metalloprotease inhibitor.

In an alternative embodiment, derivatives, analogs, or subsequences of CNS myelin inhibitory proteins which inhibit the native inhibitory protein function can be used in regimens where an increase in neurite extension, growth, or regeneration is desired, e.g., in patients with nerve damage. Patients suffering from traumatic disorders (including but not limited to spinal cord injuries, spinal cord lesions, or other CNS pathway lesions), surgical nerve lesions, damage secondary to infarction, infection, exposure to toxic agents, malignancy, paraneoplastic syndromes, or patients with various types of degenerative disorders of the central nervous system (Cutler, 1987, In: Scientific American Medicines v. 2, Scientific American Inc., NY, pp. 11-1–11-13) can be treated with such inhibitory protein antagonists. Examples of such disorders include but are not limited to Alzheimer's Disease, Parkinsons' Disease, Huntington's Chorea, amyotrophic lateral sclerosis, or progressive supranuclear palsy. Such antagonists may be used to promote the regeneration of CNS pathways, fiber systems and tracts. Administration of antibodies directed to an epitope of CNS myelin associated inhibitory proteins such as the 35 kD and/or 250 kD proteins, (or the binding portion thereof, or cells secreting such as antibodies) can also be used to inhibit 35 kD and/or 250 kD protein function in patients. In a particular embodiment of the invention, antibodies directed to the 35 kD and/or 250 kD myelin associated inhibitory protein may be used to promote the regeneration of nerve fibers over long distances following spinal cord damage; in a specific example, monoclonal antibody IN-1 may be used.

Various delivery systems are known and can be used for delivery of CNS myelin inhibitory proteins, related molecules, or antibodies thereto, e.g., encapsulation in liposomes or semipermeable membranes, expression by bacteria, etc. Linkage to ligands such as antibodies can be used to target myelin associated protein-related molecules to therapeutically desirable sites in vivo. Methods of introduction include but are not limited to intradermal, intramuscular, intraperitoneal, intravenous, subcutaneous, oral, and intranasal routes, and infusion into ventricles or a site of tumor removal. Likewise, cells secreting CNS myelin inhibitory protein antagonist activity, for example, and not by way of limitation, hybridoma cells, encapsulated in a suitable biological membrane may be implanted in a patient so as to provide a continuous source of anti-CNS myelin inhibiting protein antibodies.

In addition, any method which results in decreased synthesis of CNS myelin inhibitory proteins may be used to diminish their biological function. For example, and not by way of limitation, agents toxic to the cells which synthesize CNS myelin inhibitory proteins (e.g. oligodendrocytes) may be used to decrease the concentration of inhibitory proteins to promote regeneration of neurons.

5.6.2.2. CNS MYELIN ASSOCIATED INHIBITORY PROTEIN RECEPTORS

CNS myelin associated inhibitory protein receptors or fragments thereof, and antibodies thereto, can be therapeutically useful in the treatment of patients with nerve damage including but not limited to that resulting from CNS trauma (e.g., spinal cord injuries), infarction, or degenerative disorders of the central nervous system which include but are not limited to Alzheimer's disease, Parkinson's disease, Huntington's Chorea, amyotrophic lateral sclerosis, or progressive supranuclear palsy. For example, in one embodiment, CNS myelin associated inhibitory protein receptors, or subsequences or analogs thereof which contain the inhibitory protein binding site, can be administered to a patient to "compete out" binding of the inhibitory proteins to their natural receptor, and to thus promote nerve growth or regeneration in the patient. In an alternative embodiment, antibodies to the inhibitory protein receptor (or the binding portion thereof or cells secreting antibodies binding to the receptor) can be administered to a patient in order to prevent receptor function and thus promote nerve growth or regeneration in the patient. Patients in whom such a therapy may be desired include but are not limited to those with nerve damage, stroke, or degenerative disorders of the central nervous system as described supra.

Various delivery systems are known and can be used for delivery of CNS myelin associated inhibitory protein receptors, related molecules, or antibodies thereto, e.g., encapsulation in liposomes, expression by bacteria, etc. Linkage to ligands such as antibodies can be used to target myelin associated protein receptor-related molecules to therapeutically desirable sites in vivo. Methods of introduction include but are not limited to intradermal, intramuscular, intraperitoneal, intravenous, subcutaneous, oral, intranasal routes, and infusion into ventricles or a site of tumor removal.

5.6.2.3. METALLOPROTEASES AND THEIR INHIBITORS

The metalloproteases of the present invention can be therapeutically useful in the treatment of various types of nerve damage or degenerative disorders of the central nervous system (such as those described supra, Section 5.6.2.2) In one embodiment, patients suffering from nerve damage resulting from trauma, stroke, or neurodegenerative disorders can be treated with the metalloprotease or proteolytically active analogs, derivatives, or subsequences thereof which stimulate neurite extension or regeneration of CNS fiber.

In an alternative embodiment, derivatives, analogs, or subsequences of the metalloproteases which antagonize or inhibit metalloprotease function, or chemical inhibitors of the metalloprotease activity, can be used in regimens where an inhibition of invasive migration and spread in the CNS is desired. Such inhibitors may include but are not limited to 1,10 phenanthroline, EDTA, EGTA, cbz-tyr-tyr, cbz-gly-phe-NH$_2$, cbz-phe-phe-NH$_2$, and cbz-gly-phe-phe-NH$_2$. 1,10 phenanthroline, EDTA, and EGTA may be obtained from commercial vendors (e.g. Sigma Chemical Co.). Cbz-tyr-tyr, cbz-gly-phe-NH$_2$, cbz-phe-phe-NH$_2$, and cbz-gly-phe-phe-NH$_2$ may also be obtained from commercial vendors (e.g. Vega Biotechnologies), or may be chemically synthesized. In specific embodiments, patients with various types of malignant tumors, in particular, those metastatic to the brain, can be treated with such inhibitors. In a preferred embodiment, a patient with a glioblastoma can be treated with such inhibitors. In another specific embodiment, administration of antibodies directed to an epitope of the metalloprotease can also be used to inhibit metalloprotease function in patients. In yet another specific embodiment of the invention, metalloprotease inhibitors and a CNS myelin associated inhibitory protein can both be administered to a patient for the treatment of a malignant tumor, examples of which include but are not limited to glioblastoma, neuroblastoma, or a melanoma.

Various delivery systems are known and can be used for the delivery of metalloproteases and related molecules, e.g., encapsulation in liposomes or semipermeable membranes, expression by bacteria, etc. Linkage to ligands such as antibodies can be used to target molecules to therapeutically desirable sites in vivo. Methods of introduction include but are not limited to intradermal, intramuscular, intraperitoneal, intravenous, subcutaneous, oral, and intranasal routes, and infusion into ventricles or a site of tumor removal.

6. OLIGODENDROCYTES AND CNS MYELIN ARE NONPERMISSIVE SUBSTRATES FOR NEURITE GROWTH AND FIBROBLAST SPREADING IN VITRO

To study the interaction of neurons with central nervous system (CNS) glial cells, dissociated sympathetic or sensory ganglion cells or fetal retinal cells were plated onto cultures of dissociated optic nerve glial cells of young rats. Whereas astrocytes favored neuron adhesion and neurite outgrowth, oligodendrocytes differed markedly in their properties as neuronal substrates. Immature ($O_4^+$, $A_2B_5^+$, $GalC^-$), oligodendrocytes were frequently contacted by neurons and neurites. In contrast, differentiated oligodendrocytes ($O_4^+$, $A_2B_5^-$, $GalC^+$) represented a nonpermissive substrate for neuronal adhesion and neurite growth. When neuroblastoma cells or 3T3 fibroblasts were plated into optic nerve glial cultures, the same differences were observed; differentiated oligodendrocytes were nonpermissive for cell adhesion, neurite growth, or fibroblast spreading. These nonpermissive oligodendrocytes were characterized by a radial, highly branched process network, often contained myelin basic protein (MBP), and may, therefore, correspond to cells actively involved in the production of myelin-like membranes.

Isolated myelin from adult rat spinal cord was adsorbed to polylysine coated culture dishes and tested as substrate for peripheral neurons, neuroblastoma cells, or 3T3 cells. Again, cell attachment, neurite outgrowth, and fibroblast spreading was strongly impaired. General physico-chemical properties of myelin were not responsible for this effect, since myelin from rat sciatic nerves favored neuron adhesion and neurite growth as well as spreading of 3T3 cells. These results show that differentiated oligodendrocytes express non-permissive substrate properties, which may be of importance in CNS development or regeneration.

6.1. MATERIALS AND METHODS

6.1.1. GLIAL CELL CULTURES

Optic nerves were dissected from 7–12 day old or young adult (180–220 g) Wistar rats and collected in plating medium (air-buffered enriched $L_{15}$ with 5% rat serum; Mains and Patterson, 1973, J. Cell Biol. 59:329–345). The meninges and blood vessels were carefully removed under a microscope and the nerves were cut into small pieces. Dissociation of 10 day old nerves was done for 25 minutes twice in 0.25% trypsin (Sigma) and 0.02% collagenase (Worthington) (Raff et al., 1979, Brain Res. 174:283–318) in CMF-PBS ($Ca^{++}/Mg^{++}$-free phosphate buffered saline) at 370C. Adult optic nerves were dissociated in 0.1% trypsin, 0.1% collagenase for 1 hour at 37° C. followed by 0.5% trypsin for 10 minutes. After washing and dissociation by trituration with a Pasteur pipet, the cells were plated into the wells of 35 mm tissue culture dishes containing four internal wells at a density of 20,000 to 30,000 cells per well (surface of well: 95 mm²). For 7–10 day old optic nerves the yield of the dissociation was about 10,000 cells per nerve. The culture substrate for most of the experiments was polyornithine (PORN, Sigma, 0.5 mg/ml in borate buffer, incubated overnight) or polylysine (PLYS, Sigma, 50 ng/ml in water); in some experiments, a dried collagen film (calf skin collagen, incubation overnight with sterile solution), laminin-coated PORN (purified mouse EHS tumor laminin (5 ng/ml, incubated for 3 hours on dishes previously coated with PORN), or plain tissue culture plastic was used. The culture medium was an enriched $L_{15}$ medium with 5% rat serum, penicillin (100 U/ml) and streptomycin (100 ng/ml) (Mains and Patterson, 1973, J. Cell Biol. 59:329–345). In some experiments, 10% fetal calf serum (FCS) was added instead of the rat serum.

Optic nerves of E13 or E17 chicken embryos were dissociated by brief trypsin/collagenase treatment and cultured for 2–7 days in $L_{15}$ with 5% FCS on PORN-coated culture dishes.

6.1.2. GLIA—NERVE CELL CO-CULTURES

Three different types of nerve cells were co-cultured with glial cells: sympathetic neurons from the superior cervical ganglion of newborn rats, sensory neurons from dorsal root ganglia of newborn rats, or cells from the retina of E17–E18 embryonic rats. Superior cervical and dorsal root ganglia were dissected and dissociated into single cells as described (Mains and Patterson, 1973, J. Cell Biol. 59:329–345; Schwab and Thoenen, 1985, J. Neurosci. 5:2415–2423). Retinas were dissected from the embryos, cleaned from adhering blood vessels and incubated in 0.03% trypsin, 0.03% DNase for 10 minutes at 37° C., washed by centrifugation in serum-containing medium and dissociated by trituration.

The neurons were added to 2–10 day old glial cultures in the same medium, with the addition of NGF (2.5S NGF, 50 or 100 ng/ml) for sensory and sympathetic neurons or brain-derived neurotrophic factor for the retinal cells (Johnson, J. E. et al., 1986, J. Neurosci. 6:3031–3038). In order to suppress the growth of Schwann cells added together with the peripheral neurons, pulses of cytosine arabinoside (Ara C, $10^{-5}$ M) were given twice for 24 hours on the 2nd and 5th day of co-culture in some experiments. The cultures were processed for antibody staining after 1–5 days of co-culture in the case of retina cells, or after 2 days to 3 weeks in the case of peripheral ganglion cells.

Mouse neuroblastoma cells (line NB-2A) cultured in DMEM/10% FCS were detached from the culture flasks by a brief treatment with 0.1% trypsin in CMF-Hank's solution terminated by addition of DMEM/FCS. After washing, the cells were added to glial cultures (40,000 or 20,000 cells per well) in DMEM/FCS with either 2 mM dibutyryl-cyclic AMP or glia-derived neurite promoting factor (GdNPF; Guenther et al., 1986, EMBO J. 4:1963–1966).

Mouse NIH 3T3 cells, treated identically to the neuroblastoma cells, were added to 2–3 day old cultures of 7 day old or newborn rat optic nerves at a concentration of 20,000 or 40,000 cells per well in DMEM containing 10% fetal calf serum or in MEM supplied with insulin (20 ng/ml) and transferrin (50 ng/ml). Cultures were returned to the incubator for 2–4 hours and then fixed with warm 4% formalin in phosphate buffer and double stained with the $O_1$ and $O_4$ antibodies.

6.1.3. IMMUNOFLUORESCENCE

The following antibodies as markers for oligodendrocytes, astrocytes, neurons or fibroblasts were used: oligodendrocytes: mouse monoclonal antibody (mAB) $O_4$ (Sommer and Schachner, 1981, Dev. Biol. 83:311–327); mouse mAB $O_1$ (Sommer and Schachner, 1981, Dev. Biol. 83:311–327); specific for galactocerebroside (GalC; Singh and Pfeiffer, 1985, J. Neurochem. 45:1371–1381); goat antiserum against myelin basic protein of rabbits (Omlin, et al., 1982, J. Cell Biol. 95:242–248). Precursor cells: mouse mAB $A_2B_5$ (Sera-Lab, Crawley Down, GB). Astrocytes: rabbit antiserum against glial fibrillary acid protein (GFAP) (Dahl and Bignami, 1976, Brain Res. 116:150–157). Neurons: mouse mAB against guinea pig or rabbit neurofilaments (Willard and Simon, 1981, J. Cell Biol. 89:198–205). Fibroblasts: mouse mAB O×7 against Thy-1.1 (Sera-Lab); goat antiserum against human fibronectin (LETS protein; Cappel, N.C.).

The specific antibodies were visualized by the corresponding anti-mouse, anti-rabbit or anti-goat—fluorescein isothiocyanate (FITC) or—rhodamine isothiocyanate (RITC) linked secondary antibodies (Cappel, N.C.). Prior to staining, the cultures were washed twice with PBS containing 5% sucrose and 0.1% bovine serum albumin (BSA). The antibodies $O_1$, $O_4$ and $A_2B_5$ were directed against surface antigens and were therefore incubated on the living cultures at room temperature for 30 minutes at a dilution of 1:20 in PBS/sucrose/BSA. Antibodies against Thy-1 were diluted 1:10, anti-fibronectin 1:20. The cultures were then rinsed twice, fixed for 10 minutes with 4% formalin in PBS, rinsed again, incubated for 1 hour with the labeled secondary antibodies (dilution 1:30 to 1:100), washed and mounted in PBS:glycerol (1:1).—For visualization of myelin basic protein (MBP) the cultures were briefly fixed in 4% formalin, then treated with ethanol/acetic acid and finally incubated with anti-MBP antiserum (1:500 dilution) for 1 hour at room temperature. Ethanol/acetic acid fixation was also used for visualization of neurofilaments. For double labeling experiments of $A_2B_5$ or $O_1$ antibodies with the $O_4$ antibody, living cultures were first incubated with antibodies $A_2B_5$ or $O_1$ followed by anti-mouse-FITC, and then with antibody $O_4$ antigen; the sequence was reversed in some experiments. Staining the GFAP was done on cultures previously fixed in 95% ethanol/5% acetic acid for 30 minutes at 4° C. and rehydrated into PBS. In the case of $O_4$/GFAP double-labeling experiments, staining was first done with the $O_4$ antibody on the living cultures followed by 10 minutes fixation in 4% formalin, subsequent ethanol/acetic acid treatment and GFAP-staining. For visualization of MBP, the clutures were briefly fixed in 4% formalin, then treated with ethanol/acetic acid and finally incubated with anti-MBP antiserum (1:500) for one hour at room temperature. Ethanol/acetic acid fixation was also used for visualization of neurofilaments.

Double-labeled cultures were evaluated by systematically screening in the fluorescence microscope for the presence of one antigen (usually $O_4$), and every labeled cell was examined for the presence of the other antigen, e.g. $A_2B_5$, $O_1$, or GFAP.

6.1.4. EVALUATION OF CO-CULTURES WITH NERVE Cells, Neuroblastoma Cells, or 3T3 Cells Antibody-labeled cultures were systematically screened in the fluorescence microscope and all $O_4$-labeled cells were photographed. The same fields were photographed under phase contrast illumination. The oligodendrocyte surface area occupied by or in contact with neurons, neurites, ganglionic Schwann cells, or 3T3 cells was estimated and the oligodendrocytes were grouped into 3 categories: cells with <20%, 20%–80%, or >80% of the territory covered by neurons, neurites or 3T3 cells. Single thin processes, especially of immature cells, were often excluded from the evaluation for reason of comparability with the dense process network of highly branched oligodendrocytes. In experiments with retinal cells, total oligodendrocyte territory and areas overlapped by retinal cells were measured with a Hewlett-Packard digitizer. The oligodendrocyte subtypes were identified on the corresponding fluorescence micrographs. The criteria used for identification were cell morphology and antigenic characteristics ($O_4$/$O_1$). $A_2B_5$-staining could not be used as a marker for immature cells, since this antigen was rapidly lost (without a concomitant change in cell morphology); after coculture with neurons. The distinguishing morphological criteria were: shape and size of the cell body, number of primary processes, branching pattern of processed, and the occurrence of anastomoses and membrane sheets within the process network. With these criteria, highly branched oligodendrocytes and immature oligodendrocytes could be reproducibly distinguished. Most (but not all) of the highly branched cells were positive for the $O_1$ antigen; immature cells were consistently negative.

Quantification of the direction of neuroblastoma process outgrowth with respect to highly branched oligodendrocytes was done as illustrated in FIG. 5. Highly branched oligodendrocytes were sampled systematically, and neighbouring neuroblastoma cells were classified as "adjacent" if the distance between the edge of the oligodendrocyte process network and the NB-2A cell was less than 2 cell body diameters. Further cells were classified as "distant" (FIGS. 4A–F and 5). A circle with 8 sectors (4 classes) was overlaid over the center of each neuroblastoma cell, oriented towards the nearest oligodendrocyte cell body, and the neuroblastoma processes counted in each sector (FIG. 5).

6.1.5. PREPARATION OF MYELIN

Spinal cords were dissected from 200 g rats, carefully cleaned from adhering dorsal and ventral roots, and homogenized (polyton, 30 seconds at half maximal speed). Sciatic nerves were dissected, minced and homogenized. Myelin fractions were isolated by flotation of low speed supernatants on sucrose density gradients (Colman et al., 1982, J. Cell Biol. 95:598–608). In some experiments, to remove possible trapped contaminants, the crude membrane fraction was washed following hypotonic shock. Sedimentation in hypotonic medium was achieved at 10,000× g for 5 minutes. Membrane fractions in sucrose solutions containing no more than 50 mM ionic species were adsorbed for several hours onto the wells of PLYS-coated tissue culture dishes (about 0.1 mg of protein per $cm^2$ of tissue culture dish). Unbound membranes were removed by three washes with CMF-Hank's solution. Coated dishes were then immediately used in substrate testing experiments. In experiments with sympathetic or sensory neurons small droplets of central or peripheral myelin were deposited in defined patterns over 35 mm culture dishes.

Sympathetic or sensory neurons cultured as described above were examined after 12 hours to 4 days, neuroblastoma cells after 5–24 hours, and 3T3 cells after 1–4 hours. For quantification, neuroblastoma cells were classified as round cells, cells with filopodia or short processes, or cells with processes longer than one cell body diameter. 3T3 cells were classified as round cells, cells with filopodia or short processes, or large flat cells. Three to four micrographs per culture were taken at random from 3 cultures for each experimental point.

6.2. RESULTS

6.2.1. CULTURES OF DISSOCIATED YOUNG OR ADULT RAT OPTIC NERVES

GFAP positive astrocytes accounted for about 30% of the cells in dissociated 10 day old rat optic nerves. About 50% of the cells were positive for the $O_4$ antigen, a marker for differentiated, (GalC-positive) and immature ($A_2B_5$-positive) oligodendrocytes. No overlap was seen in the labeling between $O_4$ and GFAP or $O_4$ and Thy-1, confirming the specificity of the $O_4$ antibody as a marker for the oligodendrocyte family (Sommer and Schachner, 1981, Dev. Biol. 83:311–327). Thy-1-positive fibroblasts with large flat morphologies accounted for about 20% of the cells in young rat optic nerves.

6.2.2. SUBTYPES OF OLIGODENDROCYTES

In cultures from 7–10 day old rats, about 50% of the $O_4$-positive cells were $A_2B_5$-labeled cells. Such cells were $O_1$-negative (Table I) and had different morphologies, including cells with irregular processes from polygonal cell bodies, flat cells with peripheral processes, bipolar cells, or cells decorated with filopodia. On the basis of this marker profile ($A_2B_5^+$, $O_4^+$, $O_1^-$) and in agreement with Schnitzer and Schachner (1982, Cell Tissue Res. 2245:625–636), we interpret these cells as being precursor and immature oligodendrocytes and collectively called them "immature oligodendrocytes". This cell group is probably heterogenous, as is also suggested by the different morphologies. Filopodia-carrying cells may be the most advanced (Table I).

TABLE I

A: OLIGODENDROCYTE SUBPOPULATIONS (7 DAY OPTIC NERVES, 2 DAYS IN CULTURE) DIFFER IN THEIR LABELING BY THE ANTIBODY $A_2B_5$

| | Percentage of Labeled Cells | | |
|---|---|---|---|
| | $A_2B_5+/O_4^-$ | $A_2B_5+/O_4+$ | $A_2B_5^-/O_4+$ |
| Highly branched oligodendrocytes | 0 | 9 ± 4 | 91 ± 4 |
| Cells with irregular or polygonal shapes | | | |
| flat membraneous cells | 37 ± 4[a] | 51 ± 6 | 12 ± 6 |
| process-bearing cells | 18 ± 5 | 74 ± 5 | 8 ± 2 |
| cells with filopodia | 0 | 57 ± 8 | 43 ± 8 |

B: OLIGODENDROCYTE SUBPOPULATIONS (7–10 DAY OPTIC NERVES, 2 DAYS IN CULTURE) CHARACTERIZED BY THE ANTIBODIES $O_1$ (GalC) and $A_2B_5$*

| | Percentage of Labeled Cells | | |
|---|---|---|---|
| | $A_2B_5+/O_1^-$ | $A_2B_5+/O_1+$ | $A_2B_5^-/O_1+$ |
| Highly branched oligodendrocytes | 0 | 7 ± 2 | 93 ± 2 |
| Cells with irregular or polygonal shapes | | | |
| flat membraneous cells | 100 | 0 | 0 |
| process-bearing cells | 84 ± 6 | 14 ± 6 | 1.5 ± 1.5 |
| cells with filopodia | 91 | 1 | (8 ± 8) |

*Dissociated 7–10 day old rat optic nerve cells were cultured on PORN for 2 days and labeled by either first antibody $A_2B_5$ (detected by anti-mouse FITC) followed by $O_4$ or $O_1$ (detected by anti-mouse-RITC) or vice versa. The proportion of double-labeled cells was calculated from the values obtained for $A_2B_5^+/O_{4/1}^-$ and $A_2B_5^+/O_{4/1}^+$ cells. Values represent the means ± SEM of 4–6 cultures(120–200 cells/culture) from 2 separate experiments.
[a]This population of $A_2B_5^+/O_{4/1}^-$ cells contains type II astrocytes and precursor cells not expressing any oligodendrocyte marker.
[b]Variable, weak, granular staining About 50% of the $O_4$-positive cells were $A_2B_5$-negative and $O_1$-positive after 2 days in culture under our culture conditions. Most of these cells showed a typical, highly branched radial process network. Due to this characteristic morphology we called these cells highly branched oligodendrocytes (Table I). After 2 days in culture, most highly branched oligodendrocytes from optice neres of 10 day old rats were stained with an antiserum against myelin basic protein (MBP). We therefore interprete these cells as being myelin forming oligodendrocytes. Their characteristic process network may be the result of an unstable, partially collapsed myelin membrane containing occasional flat membrane areas. The total yield of cells from adult nerves was very low. Both, differentiated $O_1$-positive highly branched oligodendrocytes as well as immature $A_2B_5$-positive oligodendrocytes were also present in cultures of adult tissue.

6.2.3. RESPONSE OF VARIOUS CELL TYPES TO HIGHLY BRANCHED OLIGODENDROCYTES

6.2.3.1. CO-CULTURES WITH SYMPATHETIC OR SENSORY NEURONS

Dissociated cells from newborn rat superior cervical ganglia or dorsal root ganglia were added to glial cells after 2–10 days in culture. Ganglionic Schwann cells and fibroblasts were eliminated by pulses of Ara C in some of the experiments. NGF (50 or 100 ng/ml) was added to the culture medium, leading to a rapid fiber outgrowth and to the formation of dense neurite networks within a few days. NGF alone had no effect on the occurrence and morphology of oligodendrocytes. Glial cell types were identified by antibody staining at the end of the experiments (2 days to 2 weeks of co-culture).

Figure 1A:
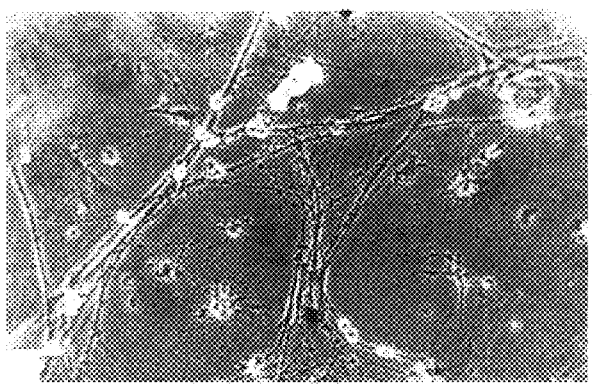
FIGS. 1E and 1F show that antibody $O_4$-positive cells with the typical morphology of immature oligodendrocytes are permissive for sympathetic neurites (arrow-heads) (5 days in vitro). Magnification: ×380.
FIGS. 1G and 1H show that E 20 rat retinal cells (2 days in vitro) do not adhere or grow neurites onto highly branched, antibody $O_1$-positive oligodendrocytes. Magnification: ×200.
Figure 1B:
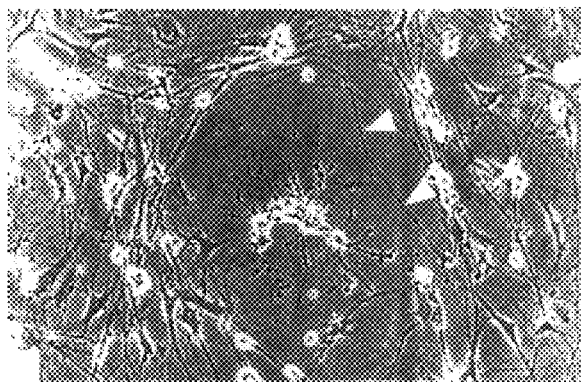
Figure 1C:
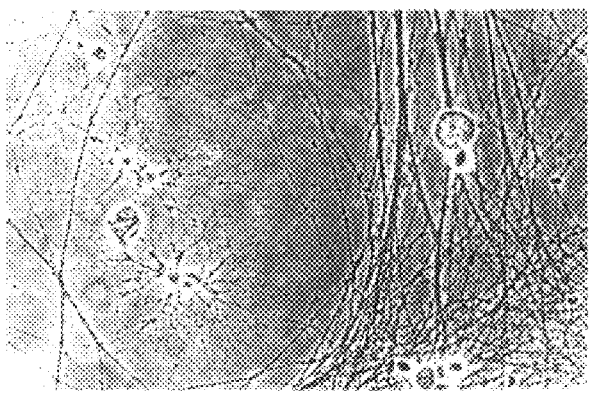
Figure 1D:
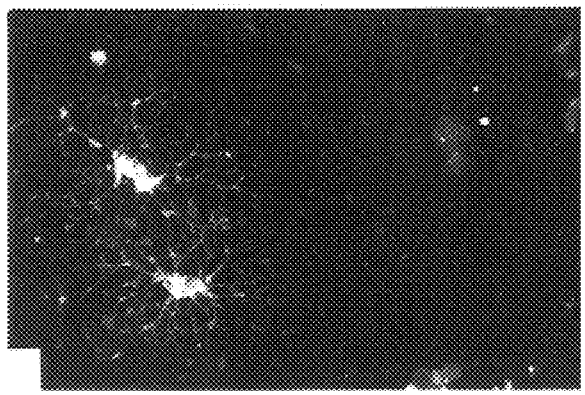
Figure 1E:
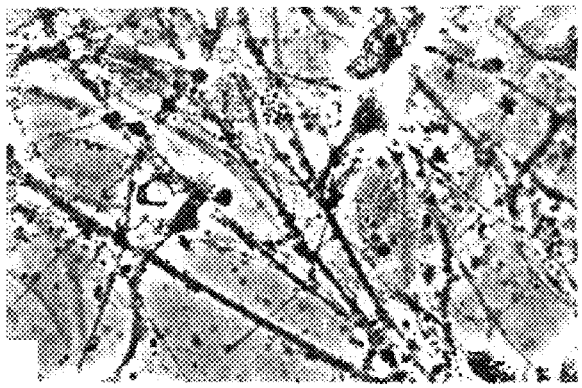
Figure 1F:
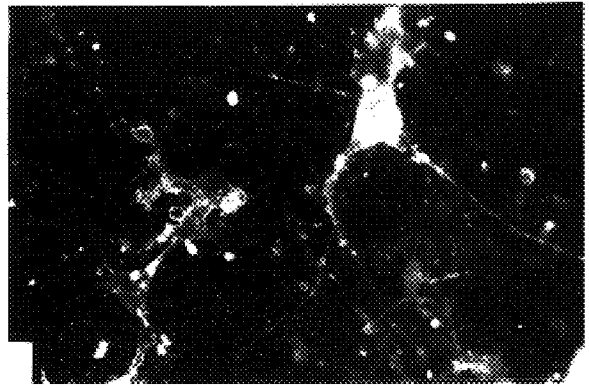
Figure 1G:
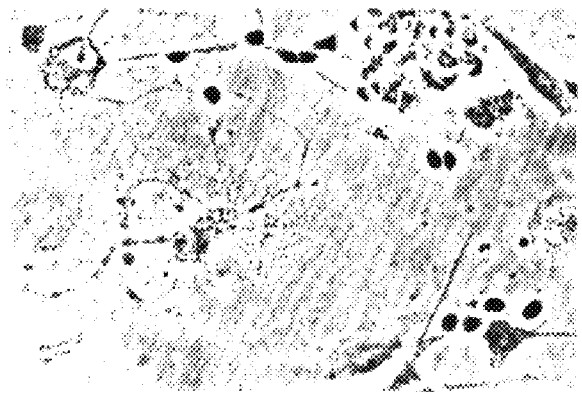
Figure 1H:
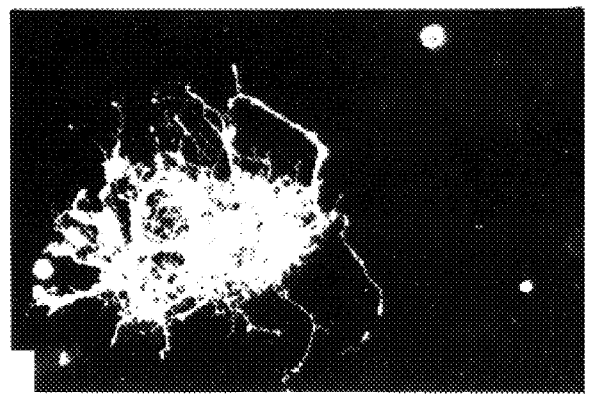
Figures 2A, 2C:
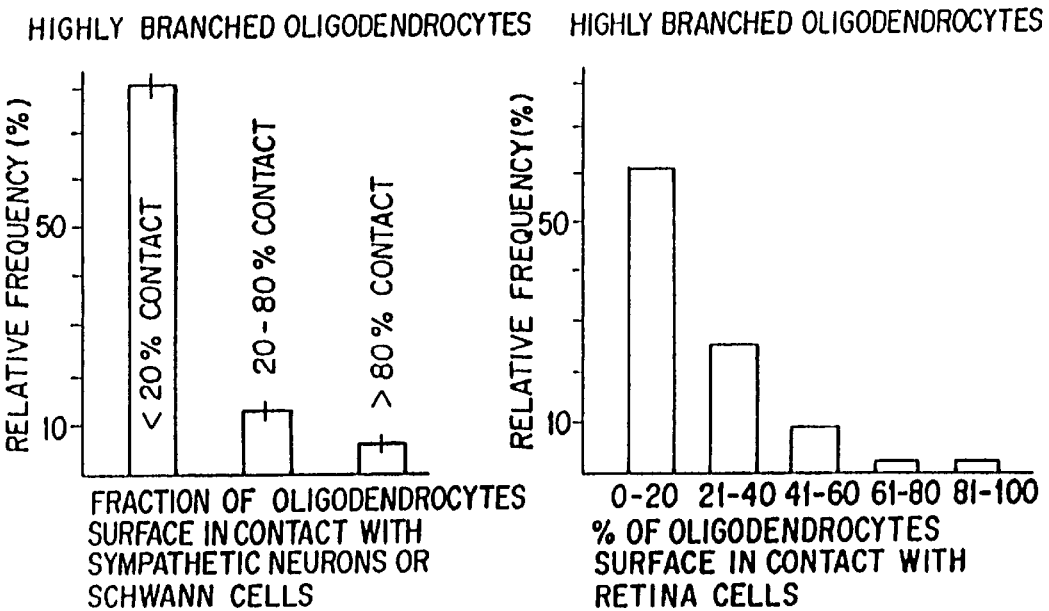
Figures 2B, 2D:
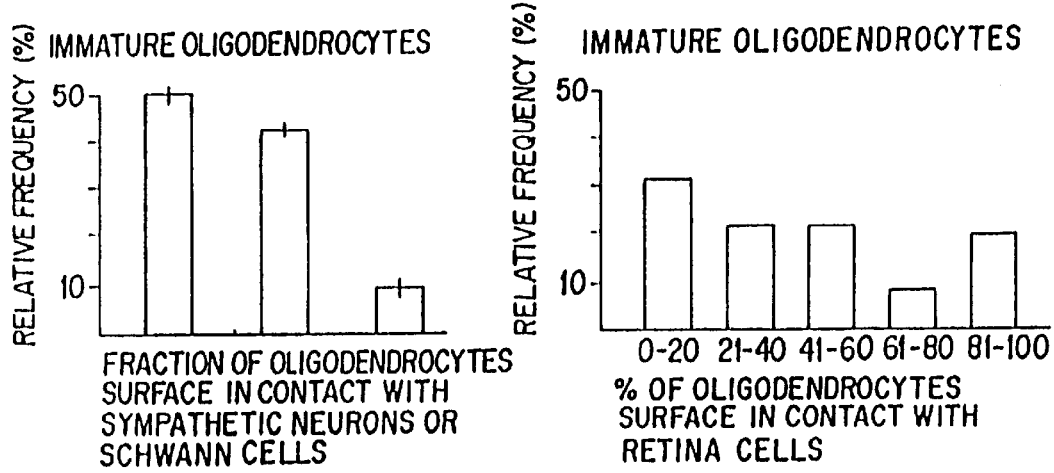

In cultures with a dense neurite plexus, the most striking observation was the occurrence of "windows" free of neurites in the center of which cells with radial, highly branched processes could be observed (FIGS. 1A–H). Antibody staining identified these cells as highly branched oligodendrocytes. A quantification of the interaction of oligodendrocytes with sympathetic ganglion cells is shown in FIGS. 2A and 2B. Astrocytes adjacent to oligodendrocytes were rare in these cultures since the overall glial cell density was low; preferential association with astrocytes could, therefore, not account for this result. Highly branched oligodendrocytes excluded neurons from their territory irrespective of the culture substrate used. The same "windows" were formed on plain plastic, collagen, PORN- or laminin-coated culture dishes. No difference was seen between sympathetic and sensory neurons; both were excluded from the territory of highly branched oligodendrocytes. Likewise, Schwann cells, when present, did not invade or overgrow the oligodendrocyte process networks (FIG. 1B). In contrast, immature oligodendrocytes, characterized by their irregular shapes and the absence of $O_1$-antigen, did allow neurite growth on their processes and cell bodies (FIGS. 1B, 1E, 1F). $A_2B_5$ could not be used as a marker for immature oligodendrocytes in co-cultures with neurons, as this antigen was rapidly lost after addition of the neurons. Recent direct observations of the encounter of growth cones with oligodendrocytes showed that growth cone movement was arrested after filopodial contact is established. Normal growth cone activity was seen during contact and crossing of immature cells. These observations also exclude the possibility that the "windows" were formed secondarily in the neurite plexus. Astrocytes in the same cultures were often overgrown by single neurites or neurite bundles (FIGS. 3A, 3B). This was true for both morphological types, flat and stellate cells.

6.2.3.2. CO-CULTURES WITH FETAL RAT RETINAL CELLS

After plating retinal cells at monolayer density on top of 5 day old cultures of optic nerve non-neuronal cells, a typical rearrangement of the retinal cells could be observed; whereas oligodendrocyte precursor cells were often contacted by retina cells, the highly branched oligodendrocytes were mostly free of them (FIGS. 1G, 1H, 3C, 3D). Again, astrocytes were preferred as a substrate over PORN.

6.2.3.3. RESPONSE OF OTHER CELL TYPES TO HIGHLY BRANCHED OLIGODENDROCYTES

Figure 4A:
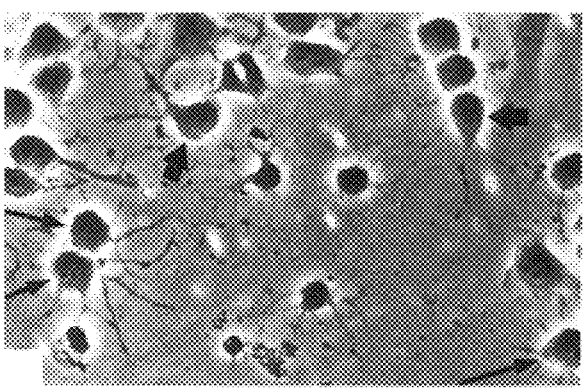
Figure 4B:
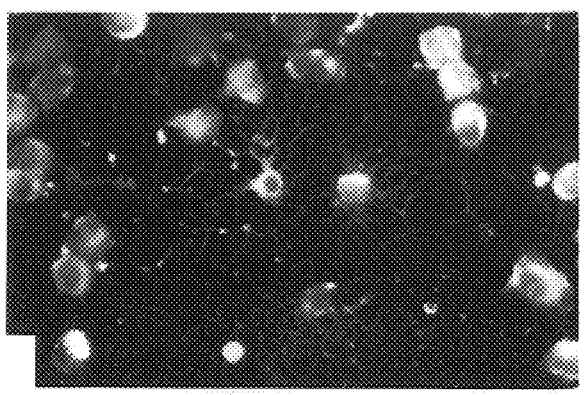

Neuroblastoma cells (line NB-2A) were plated at high cell density into dissociated optic nerve cultures and stimulated for fiber production by 2 mM dibutyryl-cyclic-AMP or by GdNPF. Seven, 24 or 48 hours later, the cultures were fixed and oligodendrocytes were identified by antibodies $O_4$ and $O_1$. Again, the territories of highly branched oligodendrocytes were clearly spared by neuroblastoma cells (FIGS. 4A, 4B). Processes produced by neuroblastoma cells situated close to oligodendrocytes were pointing away from the oligodendrocytes (FIGS. 4A, 4B; FIG. 5 and Table IA).

TABLE IA

ORIENTATION OF NEUROBLASTOMA PROCESSES WITH REGARD TO HIGHLY BRANCHED OLIGODENDROCYTES

| Sector† | % of Processes in Each Sector | |
|---|---|---|
| | Adjacent Neuroblastoma Cells | Distant Neuroblastoma Cells |
| 1 | 7 ± 1.4 | 25 ± 2.4 *** |
| 2 | 34 ± 1.2 | 26 ± 1.2 *** |
| 3 | 33 ± 2.7 | 25 ± 2.3 * |
| 4 | 26 ± 2.3 | 24 ± 2.7 |

†Shown in FIG. 5
* $p < 0.0.05$
*** $p < 0.001$

Figure 4C:
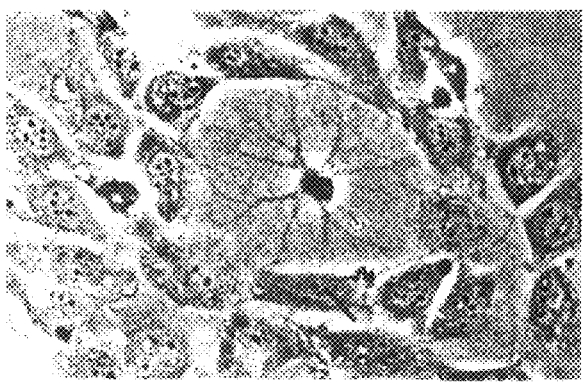
Figure 4D:
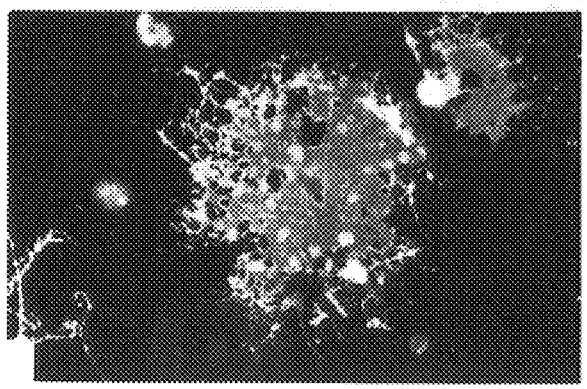
Figure 4E:
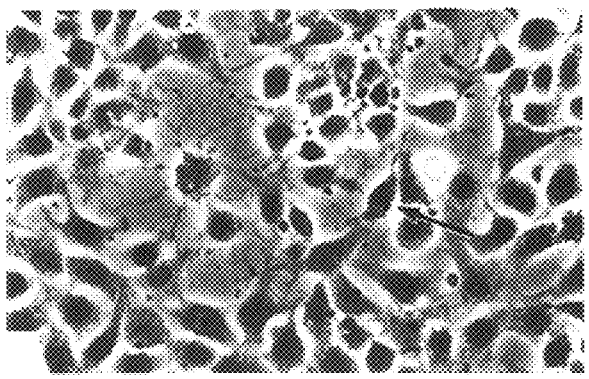
Figure 4F:
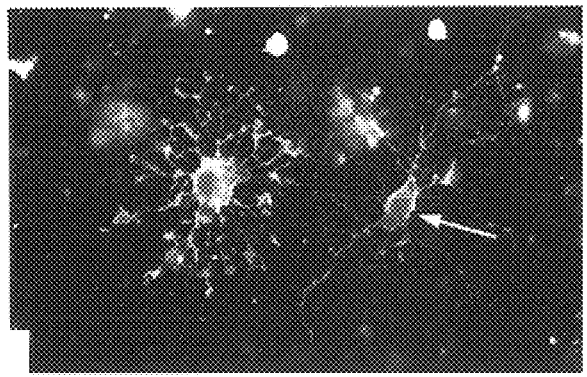

Primary culture fibroblasts and astrocytes in the optic nerve preparations as well as mouse 3T3 cells showed a drastic avoidance behaviors towards highly branched oligodendrocytes. 3T3 cells plated at high cell density into optic nerve glial cultures attached and flattened out between 30 minutes and 3 hours on the PORN substrate. In these forming monolayers, characteristic "windows" appeared corresponding to the territories of highly branched oligodendrocytes (FIGS. 4C, 4D). At the sites of contact, 3T3 cells formed a crescent-shaped bulge of cytoplasm. Lamellipodia were absent in this region. Significantly, fibroblasts that landed directly on highly branched oligodendrocytes completely failed to spread. As for neurons, immature oligodendrocytes were not visibly avoided by 3T3 cells (FIGS. 6A–B).

6.2.4. ABSENCE OF SPECIES SPECIFICITY

Neither the specific morphology nor the unfavorable substrate property of oligodendrocytes were species specific. Dissociated non-neuronal cells from E13 and E17 chick optic nerve contained besides $O_4$-positive/$A_2B_5$-negative/$O_1$-positive highly branched oligodendrocytes. 3T3 cells plated on top of chicken non-neuronal cells formed the characteristic "windows" around these chick oligodendrocytes.

6.2.5. MYELIN AS A SUBSTRATE

Figure 7A:
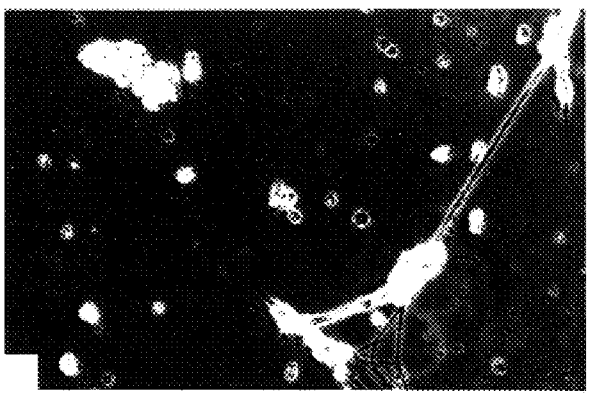
Figure 7B:
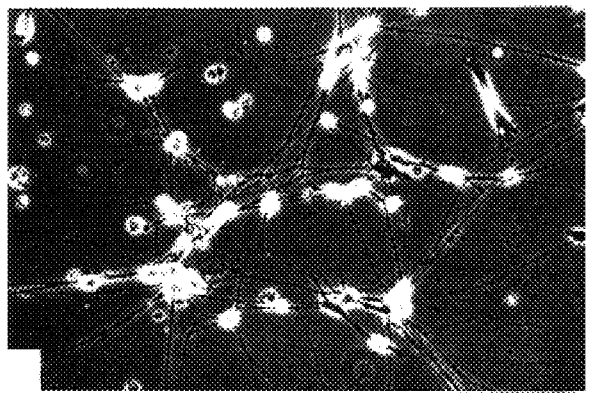
Figure 7C:
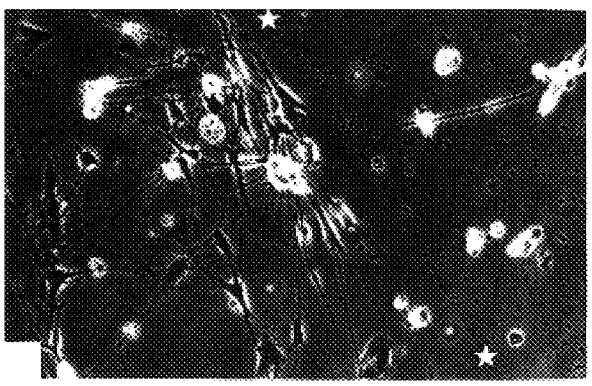
Figure 7D:
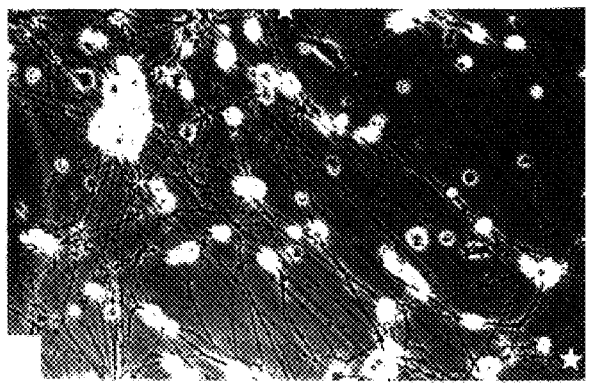

The properties of myelin as a substrate for neurons or fibroblasts were also tested, since myelin consists of spirally wrapped oligodendrocyte membranes. Crude myelin fractions from adult rat spinal cord or sciatic nerve were prepared by flotation on a sucrose gradient. The myelin was adsorbed to PLYS-coated tissue culture dishes and tested for its substrate properties for superior cervical ganglion cells, dorsal root ganglion cells, neuroblastoma cells and 3T3 cells. All four cell types attached poorly to CNS myelin and showed marked difficulties in their process outgrowth. Sympathetic and sensory neurons on CNS myelin remained round or produced short, abortive fibers in spite of the presence of NGF (50 ng/ml or 100 ng/ml) (FIGS. 7A, 17C). In contrast, long fibers were produced on islets of sciatic nerve myelin in the same culture dishes (FIGS. 7B, 17D). Small CNS myelin islets on PLYS appeared as "windows" outlined by excluded neurites, whereas PNS myelin-PLYS boundaries were apparently not detected by growing neurites.

Process outgrowth from neuroblastoma cells (line NB-2A) in the presence of dibutyryl-cyclic AMP was significantly reduced by CNS myelin (FIG. 8A).

Spreading of 3T3 fibroblasts was strongly inhibited by CNS myelin (FIG. 8B). 3T3 cells remained round or produced spindle-shaped or polygonal morphologies with a minimal cell substrate interaction. In contrast, large flat membranes were produced within 20–30 minutes on polylysine and, with a somewhat slower time-course, also on myelin from the peripheral nervous system (FIG. 8B). Nonpermissiveness was associated, at least in large part, with myelin membranes, since sedimentation at 10,000× g for 5 minutes under hypotonic conditions (see Section 6.1.5., supra) was sufficient to pellet most nonpermissive membranes. Under these conditions, most surface membrane components floating to densities smaller than the one of 0.85 M sucrose, would not be expected to sediment.

CNS myelin nonpermissiveness is not due to astrocyte membranes, since a cell membrane preparation from CNS tissue containing minimal amounts of white matter (superficial cortical layers) was a permissive substrate for fibroblast spreading.

These experiments show that, in parallel to the effects of living, highly branched oligodendrocytes, myelin from the CNS is also a strongly nonpermissive substrate for primary culture neurons, neuroblastoma cells, and 3T3 fibroblasts. Myelin from the peripheral nervous system does not show a comparable nonpermissive substrate effect.

6.3. DISCUSSION

In the present study, we observed that myelin forming oligodendrocytes and isolated CNS myelin exert a nonpermissive substrate effect on outgrowing neurites of sympathetic and sensory neurons and neuroblastoma cells, as well as for the attachment of retinal cells and the spreading of fibroblasts.

Several classes of cells were present in short-term cultures of dissociated rat optic nerves: oligodendrocytes, astrocytes (GFAP-positive) fibroblasts (Thy-1, fibronectin-positive) and several types of precursor cells. Within the oligodendrocyte family ($O_4$-positive; Sommer and Schachner, 1981, Dev. Biol. 83:311–327), one main subtype of cells was characterized by the absence of the $O_1$ antigen (GalC) and of MBP, two components highly characteristic of myelin (Mirsky, et al., 1980, J. Cell Biol. 84:483–494), and the presence of binding sites for the antibody $A_2B_5$. $A_2B_5$ was shown to be a marker for oligodendrocyte/type II astrocyte precursors, type II astrocytes, and neurons (Schnitzer and Schachner, 1982, Cell Tissue Res. 224:625–636; Abney, E. R. et al., 1981, Dev. Biol. 100:166–171; Raff, et al., 1983, Nature 303:390–396). Therefore, we considered this cell class to represent immature oligodendrocytes, probably including precursors such as those described by Dubois-Dalcq (1986, Soc. Neurosci. Abstr. 12:767) and Sommer and Noble (1986, Soc. Neurosci. Abstr. 12:1585). The presence of $O_4$ distinguishes these cells from the O2A precursors (Raff, M. C. et al., 1983, Nature 303:390–396). These immature cells showed irregular and variable morphologies with bipolar shapes or polygonal cell bodies and irregular processes, often decorated with filopodia. The cell class is probably heterogenous; cell division could be observed. The second main oligodendrocyte subclass consisted of $A_2B_5$-negative, $O_1$-positive cells, possessing a radial, highly branched and anastomosing process network. Most of these highly branched oligodendrocytes in 2 day old cultures of 10 day old rat optic nerves were positive for MBP under our culture conditions. We thus interpret this frequent cell type as representing oligodendrocytes actively involved in the synthesis of myelin membranes which are deposited flat on the culture substrate in the absence of axons. These membranes are unstable and collapse to form the characteristic, anastomosing process network. This cell type has been described as "hairy eyeball cell" (Sommer and Schachner, 1981, Dev. Biol. 83: 311–327), and formation of whorls of compact myelin by such cells has been observed after prolonged times in culture (Rome et al., 1986, J. Neurosci. Res. 15:49–65; Yim et al., 1986, J. Biol. Chem. 261:11808–11815).

Both immature and myelin forming oligodendrocytes were seen in cultures of 7 to 10 day old or adult rat optic nerves, and also in cultures of 1 day rat optic nerves, newborn rat spinal cord or adult rat corpus callosum, as well as in cultures of spinal cord and optic nerves of E13 or E17 chicken embryos. Immature cells clearly were predominant in dissociates from younger stages, but the large drop in cell yield upon dissociation with increasing age precluded any quantitative population analysis. However, immature oligodendrocytes could also be obtained consistently from adult rat white matter tissues, confirming earlier observations by French-Constant and Raff (1986, Nature 319:499–502).

The addition of neurons to established glial cultures showed dramatic differences in substrate properties for neuronal attachment and fiber outgrowth among the various types of non-neuronal cells. Astrocytes, particularly the flat reactive protoplasmic astrocytes, were adhesive and favorable for neuronal attachment and outgrowth, in agreement with earlier observations (Foucaud et al., 1982, Cell Res. 137:285–294; Hatten, et al., 1984, J. Cell Biol. 98:193–204; Noble, et al., 1984, J. Neurosci. 4:1982–1903; Fallon, 1985, J. Cell Biol. 100:198–207). Immature oligodendrocytes also were frequently contacted by neurites or nerve cell bodies. This behavior could be of high physiological relevance. During development, oligodendrocyte precursors migrate into the already formed axonal bundles and extend processes to contact a certain number of axons. These processes then start to enwrap and spiral around the axons, thus forming the structure called myelin (Wood and Bunge, 1984, W. T. Norton, ed., 1–46).

In sharp contrast to astrocytes and oligodendrocyte precursors, we found that myelin forming oligodendrocytes display strongly nonpermissive substrate properties for neuronal attachment and fiber outgrowth as well as for fibroblast attachment and spreading. This effect was strong and pronounced even on laminin-coated culture dishes, which otherwise represent an excellent substrate for neurite growth (Manthorpe, et al., 1983, J. Cell Biol. 97:1882–1980; Rogers, et al., 1983, Dev. Biol. 98:212–220). This effect was not overcome by high doses of NGF in cultures of sympathetic and sensory neurons, or GdNPF or dibutyryl-cyclic-AMP in cultures of neuroblastoma cells. A similar or identical nonpermissive substrate property was associated with rat CNS myelin but not with myelin from peripheral nerves. The effect was strictly contact-dependent, since nerve cells or fibroblasts grew well and were free to move in the immediate surrounding of these oligodendrocytes or of CNS myelin islets. Mouse 3T3 cells were also inhibited by chicken oligodendrocytes, showing that this effect is not species-specific.

In the rat optic nerve, the peak number of axons is reached at embryonic day 20, followed by a dramatic loss of axons (Crespo, et al., 1985, Dev. Brain Res. 19:129–134). Oligodendrocyte precursors appear from E17 onward (Raff, et al., 1985, Cell 42:61–69) and express GalC around birth (Miller, et al., 1985, Dev. Biol. 111:35–41). The first myelin detectable by electron microscopy appears at postnatal day 6 (Hildebrand and Waxman, 1984, J. Comp. Neurol. 224:25–37). This clear-cut temporal dissociation between axonal growth and myelin formation is also present in chicken optic nerves (Rager, 1980, Cell Biol. 63:1–92) and, although less well studied, in many white matter tracts of the CNS (Matthews and Duncan, 1971, J. Comp. Neurol. 142:1–22; Looney and Elberger, 1986, J. Comp. Neurol. 248:336–347). During normal development, growing axons therefore probably never encounter myelin or myelinating oligodendrocytes within their fascicles, but rather interact with precursors and immature oligodendrocytes. The extremely slow time-course observed for in vitro myelination (Wood, et al., 1980, Brain Res. 196:247–252; Wood and Williams, 1984, Dev. Brain Res. 12:225–241) could be consistent with a situation where undifferentiated oligodendrocytes first interact with axons and are then induced to differentiate and to form myelin.

In contrast to development, during CNS regeneration, axonal growth cones or sprouts do encounter mature oligodendrocytes and myelin. Substrate properties of CNS tissue, in particular the absence of potent neurite promoting substrates like laminin in the differentiated CNS of higher vertebrates, are important aspects in the context of CNS regeneration (Liesi, 1985, EMBO J. 4:2505–2511; Carbonetto, et al., 1987, J. Neurosci. 7:610–620). However, since myelin and oligodendrocytes persist for a long time in denervated CNS tracts (Fulcrand and Privat, 1977, J. Comp. Neur. 176:189–224; Bignami, et al., 1981, J. Neuropath, Exp. Neurol. 40:537–550), the absence of any fiber regeneration in white matter areas in contrast to peripheral nerves and PNS/CNS transplants could be related to these nonpermissive substrate factors.

Under normal conditions, blocking certain territories for later growing axonal populations during development, antagonism between favorable and nonpermissive substrate molecules during development of CNS projection patterns, or the spatial limitation of sprouting in the differentiated CNS are possible functions for this oligodendrocyte associated nonpermissive substrate property.

7. TWO MEMBRANE PROTEIN FRACTIONS FROM CENTRAL NERVOUS SYSTEM MYELIN WITH INHIBITORY PROPERTIES FOR NEURITE GROWTH AND FIBROBLAST SPREADING

We have searched for surface components in CNS white matter, which would prevent neurite growth. CNS, but not PNS, myelin fractions from rat and chick were highly nonpermissive substrates in vitro. We have used an in vitro spreading assay with 3T3 cells to quantify substrate qualities of membrane fractions and of isolated membrane proteins reconstituted in artificial lipid vesicles. CNS myelin nonpermissiveness was abolished by treatment with proteases and was not associated with myelin lipid. Nonpermissive proteins were found to be membrane bound and yielded highly nonpermissive substrates upon reconstitution into liposomes. Size fractionation of myelin protein by SDS-PAGE revealed two highly nonpermissive minor protein fractions of molecular weight, 35 kD and 250 kD. Removal of kD and of 250 kD protein fractions yielded a CNS myelin protein fraction with permissive substrate properties. Supplementation of permissive membrane protein fractions (PNS, liver) with low amounts of 35 or of 250 kD CNS myelin protein was sufficient to generate highly nonpermissive substrates. Inhibitory 35 and 250 kD proteins were found to be enriched in CNS white matter and were found in optic nerve cell cultures which contained highly nonpermissive, differentiated oligodendrocytes.

The data presented herein (Caroni and Schwab, 1988, J. Cell Biol. 106:1281–1288) demonstrate the existence of 35 kD and 250 kD myelin membrane-bound proteins with potent nonpermissive substrate properties. Their distribution and properties suggest that these proteins might play a crucial inhibitory role during development and regeneration in CNS white matter.

7.1. MATERIALS AND METHODS

7.1.1. CELL CULTURE

Mouse NIH 3T3 cells were cultured and assayed for spreading behavior in DMEM containing 10% FCS. In control experiments, use of defined serum-free medium did not alter responses of 3T3 cells to tested substrates. Mouse neuroblastoma cells (line NB-2A) were cultured in DMEM with 10% FCS in the presence of either 1 mM dibutyryl-cAMP or of glia-derived neurite promoting factor (GdNPF). Superior cervical and dorsal root ganglia from newborn rats were dissected and dissociated into single cells as described (Mains and Patterson, 1973, J. Cell Biol. 59:329–345; Schwab and Thoenen, 1985, J. Neurosci. 5:2415–2423). Neurons were cultured in an enriched L15 medium with 5% rat serum (Mains and Patterson, 1973, J. Cell Biol. 59:329–345) and with 100 ng/ml of 2.5S nerve growth factor. Overgrowth by contaminating dividing cells was prevented by inclusion of cytosine arabinoside ($10^{-5}$ M) in the culture medium.

7.1.2. SOURCES OF TESTED SUBSTRATES

Myelin fractions were all prepared by the same procedure, involving tissue homogenization in isotonic sucrose buffer with a polytron (model PCU-2; Kinematica, Luzern, Switzerland) homogenizer (setting 4, two times 30 s, on ice) and flotation of a low speed supernatant onto a discontinuous sucrose gradient (myelin collected at 0.25 M sucrose top layer) (Colman, et al., 1982, J. Cell Biol. 95:598–608). All isolation media contained trasylol (aprotinin; Sigma Chemical Co., St. Louis, Mo.; 100 U/ml), 5 mM iodoacetamide, and 5 mM EDTA to reduce protease digestion (this reagent mixture is designated below as protease inhibitors). Finally, myelin fractions were washed hypotonically in 30 mM Hepes (pH 7.4) (medium A) plus protease inhibitors and frozen in aliquots at −80° C. CNS myelin fractions were prepared from spinal cords carefully stripped of ventral and dorsal roots, or from rat optic nerves. The following sources were used: rat, spinal cord, 3 month old Lewis rats, male; chick, spinal cord, P21; trout, spinal cord, 2 year; frog, spinal cord, 6 months. PNS myelin fractions were prepared from rat sciatic nerves (3 month male). Rat liver cell membranes were prepared by standard procedures, involving mild isotonic homogenization and collection of membranes at the density of 0.25 M sucrose (discontinuous sucrose gradient). Rat CNS tissue enriched in gray matter was obtained from superficial neocortex layers, whereas white matter-enriched tissue consisted of the corpus callosum.

7.1.3. SUBSTRATE-ASSAYING PROCEDURE

Substrates to be tested, in 40–70 mOsmol solutions, were dried onto polylysine (PLYS)-coated tissue culture dishes. Unbound membranes and solutes were removed by three washes with $Ca^{2+}Mg^{2+}$-free Hank's solution. Coated dishes were then immediately used in substrate-testing assays. For most experiments, substrates were dried onto the wells of dishes (35-mm dishes with four internal wells; Greiner, Nurtingen, Federal Republic of Germany). 3T3 cells were detached from ~30% confluent cultures by brief trypsin (0.2%) treatment in 37° C. PBS plus EDTA. Trypsinization was stopped by 10-fold excess of serum-containing DMEM; cells were collected and resuspended in DMEM-10% FCS at appropriate concentrations. 30,000 cells/$cm^2$ were added to precoated culture dishes, and experiments were scored after 1 hour in culture. In some cases, due to occasional slower spreading behavior of 3T3 cell populations, scoring had to be delayed up to 2 hours in culture. After periods of more than ~5 hours, inhibitory properties of myelin fractions in the absence of serum were less pronounced than observed in the presence of 10% FCS, possibly due to the presence of substrate digesting proteases. If substantial spreading on PLYS-coated dishes was not obtained within 2 hours in culture, tests were discarded and repeated with a fresh batch of cells. Quantitative evaluation of spreading was performed with a surface integration program on at least 30 cells per experimental point. Only spread cells were considered and a zero-spreading value (strongly refractory and round cells) was subtracted. Each experiment was repeated at least five times. Experiments were found to be subject to only small quantitative variations, and values from representative experiments are given. Spreading degrees are given as means ±standard error of the mean. When recoveries of inhibitory activity were estimated, serial dilutions of liposomes (in medium A) were assayed for nonpermissiveness. In some cases, in order to detect differences among strong inhibitory substrates, 3T3-spreading times were extended to up to 5 hours. Recovery values are based on internal calibration with a CNS myelin liposome standard, and are to be considered as first approximations. When neurite extension was evaluated, neuroblastoma cells or superior cervical ganglia neurons were seeded at ~25,000 cells/$cm^2$ and experiments were scored after 24 hours in culture.

7.1.4. SUBSTRATE PROCESSING

Protease sensitivity of inhibitory fractions was determined by digesting washed, protease inhibitor-depleted membranes with trypsin. Membrane fractions (concentrations of maximally 1 mg of protein per ml) were exposed for 10 minutes at room temperature to 0.1% trypsin. Digestion was interrupted by the addition of 0.2% trypsin inhibitor (sigma Chemical Co.) and membranes were either washed in medium A or separated from protease by Sephadex G-50 chromatography (liposomes). Under these conditions, trypsin was retarded by the column, whereas liposomes were recovered in the excluded volume. Digested, washed membranes were finally adsorbed to culture dishes, and their substrate properties were analyzed as described supra. In some experiments with myelin fractions, pronase (Sigma Chemical Co.) or elastase (Sigma Chemical Co.) were used. In those instances, protease was removed by three washes of the myelin in 30 mM Hepes, pH 7.4.

Extraction of peripheral membrane proteins from CNS myelin was performed by resuspending membranes in either 4 M guanidinium chloride (Merck & Co., Inc. Rahway, N.J.)/30 mM Hepes or in 500 mM unbuffered Tris base (Sigma Chemical Co.). Protease inhibitors were routinely included in the extraction buffers. After incubation for 30 minutes at room temperature, myelin was sedimented, washed in medium A, and assayed for its substrate properties.

Ethanol/ether (2:3 vol ratios) extraction of myelin was performed by a standard procedure (see, for example, Everly, J. L. et al., 1973, J. Neurochem. 21:329–334). Solvent-insoluble fraction was reconstituted into lipid vesicles (see Section 7.1.5,) infra). The lipid-containing soluble fraction was dried and reconstituted by the cholate method (see Section 7.1.5, infra).

7.1.5. LIPOSOMES

Liposomes were prepared in medium A by the cholate method (Brunner, et al., 1978, J. Biol. Chem. 253:7538–7546). Protein was solubilized in 2% SDS (in medium A plus protease inhibitors); insoluble protein was sedimented and discarded. Solubilized protein was precipitated with a 30-fold excess of acetone. To obtain reproducible yields, acetone precipitation was allowed to proceed for 15 hours at 4° C. Protein extracts from tissues were prepared by homogenization of minced tissue with a glass-teflon potter in 2% SDS-containing, protease inhibitors-supplemented, medium A. Solubilized protein was then precipitated with ice-cold acetone as described above. Extracts from cultured cells were prepared by, first, detaching the cells with a rubber policeman in the presence of PBS plus EDTA plus protease inhibitors, and by then homogenizing suspended cells with a glass-teflon potter. Upon low-speed pelleting of nuclear material, 2% SDS was added to supernatants and solubilized protein was precipitated with ice-cold acetone. In all cases, acetone-precipitated protein was sedimented (10,000× g, 15 minutes) and resuspended at 1 mg/ml in medium A with 2.5% cholate. Phospholipids (phosphatidylcholine/phosphatidylserine, 10:1) dissolved in medium A with 2.5% cholate were then added (~5–10:1 ratio of added phospholipid to protein) and liposomes were formed on a Sephadex G-50 column. When gel-extracted protein was reconstituted, precipitated protein was resuspended at ~50 $\mu$g/ml and phospholipid to protein ratios were up to 100:1.

A number of control experiments were performed. Thus, acetone precipitated myelin or gel-extracted protein did not prevent 3T3 spreading when resuspended in medium A or in medium A with 2.5% cholate and adsorbed directly onto PLYS-coated dishes. Also, running of cholate-solubilized protein on the Sephadex G-50 column, in the absence of phospholipids did not yield nonpermissive fractions. Experiments with $^{125}$I-labeled CNS myelin protein showed that ~30% of applied label was recovered in the liposome fraction from the G-50 column. In some experiments, lipid vesicles were formed in the presence of trace amounts of [$^3$H] cholesterol and were then dried onto the wells of tissue culture dishes (Greiner). Total culture dish associated membrane amounts ([$^3$H] cholesterol) were found to vary independently of tested protein, indicating that differences in liposome binding to culture dishes cannot be responsible for the observed differences in substrate properties.

7.1.6. GEL-EXTRACTED PROTEIN FRACTIONS AS SUBSTRATE

Protein was run on 3–15% gradient gels under reducing conditions. For this purpose, samples were preincubated for 30 minutes at room temperature in sample buffer containing 2% SDS and β-mercaptoethanol. Thin lanes were cut and stained with Coomassie Brilliant Blue or with the silver method. Protein bands to be analyzed were carefully aligned with the unstained gel parts to be extracted. Gel regions from the unstained gel part were cut, and minced gel was extracted for 1 hour with 0.5% SDS. In most experiments, 50 $\mu$g/ml of insulin (Sigma Chemical Co.) were included in order to reduce losses due to adsorption of protein present in low concentration. Insulin was selected for its purity and for its small size, resulting in efficient separation from the liposome fraction. In control experiments, no substrate differences could be detected when 50 $\mu$g/ml of insulin were added to various reconstitution mixtures, including protein-free liposomes. Gel-extracted protein was precipitated with a 10-fold excess of ice-cold acetone (15 hours), and sedimented protein was resuspended in cholate buffer. Protein was stored frozen in cholate buffer and reconstitution mixtures were prepared from these protein stocks. Reconstitution and test of substrate properties were performed as described above.

The amount of protein present was determined by the filter binding method (Schaffner and Weissman, 1973, Anal. Biochem. 56:502–514) with BSA (Sigma Chemical Co.) as a standard.

7.2. RESULTS

7.2.1. NONPERMISSIVE SUBSTRATE EFFECT IS FOUND IN CNS MYELIN OF HIGHER VERTEBRATES (CHICK, RAT), BUT NOT OF LOWER VERTEBRATES (TROUT, FROG)

Rat CNS myelin was found to be a nonpermissive substrate for neurite outgrowth from rat superior cervical ganglion neurons and for spreading and migration of 3T3 fibroblasts (see also section 6, supra). Analogous results were obtained when myelin was prepared from rat optic nerve or from rat brain. Neuron type apparently did not influence substrate response as similar results were obtained with dorsal root ganglion neurons. Likewise, rat CNS myelin nonpermissiveness was observed for dibutyryl-AMP-induced or GdNPF-induced outgrowth from neuroblastoma cells. Thus, nonpermissiveness of rat CNS myelin is apparently general with regard to neuron type and induction of neurite outgrowth.

Lack of regenerative fiber growth is found in the CNS of higher vertebrates but not in those of fishes and to a limited extent in those of amphibia (Bohn, et al., 1982, Am. J. Anat. 165:307–419; Stensas, 1983, In Spinal Cord Reconstruction, C. C. Kao, R. P. Bunge, and P. J. Reier, eds., Raven Press, New York 121–149; Hopkins, et al., 1985, J. Neurosci. 5:3030–3038; Liuzzi and Lasek, 1986, J. Comp. Neurol. 247:111–122). We prepared spinal cord myelin fractions from trout, frog, and chick in order to determine potential differences in substrate properties. Trout (FIG. 9) and frog (FIG. 9) CNS myelin fractions were found to have substrate properties similar to those of rat PNS myelin, whereas CNS myelin from the chick (spinal cord, postnatal 21) was a nonpermissive substrate, although slightly less so than its rat counterpart.

7.2.2. MEMBRANE-BOUND PROTEIN FRACTION OF RAT CNS MYELIN IS RESPONSIBLE FOR ITS NONPERMISSIVE SUBSTRATE PROPERTIES

Rat CNS myelin was processed by standard procedures in order to determine the nature of the component(s) responsible for its nonpermissive substrate properties. Fractions were tested for reduction of 3T3 fibroblast spreading. Data are shown in Table II.

TABLE II

NONPERMISSIVENESS OF CNS MYELIN IS DUE TO MEMBRANE-BOUND PROTEIN*

| Substrate | 3T3 spreading ($\mu m^2$) |
|---|---|
| Tissue culture plastic | 1,646 ± 309 |
| CNS myelin | |
| Untreated | 211 ± 30 |
| Trypsin-treated | 1,344 ± 181 |
| Liposomes | |
| Ethanol/ether-soluble myelin fraction | 1,253 ± 159 |
| Ethanol/ether-insoluble myelin fraction | 226 ± 45 |
| Artificial lipid vesicles, no additions | 1,328 ± 136 |

*Spreading extent of 3T3 cells was estimated after 1 hour in culture. Protein amounts to be adsorbed to wells of dishes (Grenier) were 20 μg of CNS myelin protein per cm². In the solvent extraction experiments, 100 μg of CNS myelin protein were extracted and one-fifth of resulting liposome-containing volume was dried onto wells. These myelin quantities represent about 10 times saturation levels with respect to observed nonpermissiveness.

Brief treatment of the myelin with trypsin abolished nonpermissiveness. Similar results were obtained with elastase or with pronase treatment.

Extraction of the myelin under conditions that solubilize peripheral membrane proteins (4 M guanidinium chloride or pH 10.5) failed to dissociate nonpermissiveness from low speed myelin membrane pellets. Lipid extraction with ethanol/ether yielded a permissive lipid fraction and a nonpermissive protein fraction (Table II). The latter required detergent to be solubilized and had to be incorporated into lipid vesicles in order to permit detection of nonpermissive substrate property. In control experiments, phosphatidylcholine/phosphatidylserine liposomes were a slightly less favorable substrate than tissue culture plastic (Table II). When CNS myelin protein-containing liposomes were subjected to trypsin treatment, their nonpermissive substrate properties were abolished (Table III). Thus, a membrane-bound protein fraction from rat CNS myelin is a nonpermissive substrate for 3T3 fibroblast spreading. That fraction can apparently be reconstituted in active form into artificial lipid vesicles. In control experiments, protein from membrane fractions with permissive substrate properties yielded, upon reconstitution, liposomes that were permissive for 3T3 spreading (Table III).

TABLE III

NONPERMISSIVE SUBSTRATE PROPERTY OF CNS MYELIN IS PRESERVED UPON RECONSTITUTION INTO ARTIFICIAL LIPID VESICLES

| Reconstituted Protein Fraction | 3T3 Spreading ($\mu m^2$) | Dish-Adsorbed Lipids (cpm [$^3$H]cholesterol) |
|---|---|---|
| No protein | 1,638 ± 91 | 521 ± 65 |
| CNS myelin | 136 ± 30 | 650 ± 58 |
| CNS myelin; resulting liposomes trypsinized | 1,397 ± 152 | 630 ± 32 |
| PNS myelin | 1,570 ± 136 | 620 ± 41 |
| Liver membranes | 1,445 ± 121 | 750 ± 47 |

*Tested protein fractions (100 μg) were reconstituted and one-fifth of resulting liposome-containing volume (60 μl) was absorbed to wells. The adsorbed volume contained 20,000 cpm [$^3$H]cholesterol. Dish-adsorbed counts were determined upon SDS solubilization of adsorbed liposomes. For these experiments, liposomes were removed prior to fibroblast addition. Trypsinisation of CNS myelin liposomes and separation of inhibitor-blocked trypsin from vesicles was performed as described in Section 7.1.4, supra.

7.2.3. IDENTIFICATION OF 35 kD AND 250 kD MINOR PROTEINS FROM MYELIN AS NONPERMISSIVE SUBSTRATES FOR FIBROBLAST SPREADING AND NEURITE OUTGROWTH

As myelin nonpermissiveness partially survived denaturing procedures, attempts were made to identify responsible components following separation by SDS-PAGE. In preliminary experiments, it was found that solubilization of myelin proteins in SDS-PAGE sample buffer followed by reconstitution of acetone-precipitated protein yielded a fraction possessing )30% of starting nonpermissiveness. Apparent activity recoveries were estimated by assaying serial dilutions of reconstituted protein with the 3T3 fibroblast spreading assay. As a comparison, solubilization in 2% NP-40™, 0.5% Na-deoxycholate yielded apparent activity recoveries of )80%. When CNS myelin protein was run on SDS-PAGE and the entire gel was then extracted with 0.5% SDS, recoveries of nonpermissive substrate activity were )20%. Activity could be recovered in approximately equal amounts ()10% of applied activity) from gel regions corresponding to the migration distance of 35 kD and of 250 kD proteins, respectively (FIG. 10). The inhibitory proteins were highly effective, as just 10 ng of 250 kD protein per cm² of culture dish was required to obtain half-maximal inhibition. Neither the 250 kD nor the 35 kD region contained major myelin protein bands (each region contained )3% of total silver stained myelin protein). These gel regions apparently contained more than one protein species. Reconstitution of pooled gel regions depleted of kD and of 250 kD proteins yielded permissive liposomes (FIGS. 11A–C). Thus, 35 kD and 250 kD proteins account for most of the nonpermissive substrate activity of gel-extracted CNS myelin protein. Similarly to unfractionated myelin, 35 kD and 250 kD proteins were nonpermissive substrates for fibroblast spreading and for neurite extension (FIGS. 11A–C). In control expriments, sciatic nerve protein or a liver homogenate did not generate 250 kD nor 35 kD nonpermissive protein fractions (FIG. 12). It seems, therefore, reasonable to conclude that the protein fractions identified above are responsible for the marked nonpermissive substrate properties of rat CNS myelin in vitro.

We next asked whether addition of these proteins to fractions with neutral substrate properties is sufficient to generate a nonpermissive substrate. As shown in FIG. 12, liver protein and sciatic nerve protein could yield nonpermissive substrates for 3T3 cells when supplemented with 250 kD or with 35 kD proteins from rat CNS myelin as shown in FIG. 12. In these experiments, 250 kD and 35 kD proteins were added to amounts of liver (or sciatic nerve) protein equivalent to the ones of total CNS myelin protein from which they were prepared. We conclude that 35 kD and 250 kD proteins from rat CNS myelin act as inhibitors of neurite outgrowth and of fibroblast spreading, as their addition converts a neutral substrate into a nonpermissive one.

7.2.4. NONPERMISSIVE SUBSTRATE PROPERTY IS ENRICHED IN CNS WHITE MATTER AND IN CULTURED OLIGODENDROCYTES

Considering the documented poor regenerative fiber growth found in mature CNS white matter (Nornes, H. A., et al., 1983, Cell Tissue Res. 230:15–35; Bjorklund, A. and Stenevi, U., 1984, Annu. Rev. Neurosci. 7:279–308), it was of particular interest to determine whether the 35 kD and 250 kD neurite outgrowth-inhibiting proteins from CNS myelin were enriched in CNS white matter and in myelin forming cells. Protein-containing lipid vesicles from homogenates of different CNS regions were prepared and their substrate properties were determined. Rat CNS white matter material yielded highly nonpermissive liposomes containing inhibitory 250 kD and 35 kD protein fractions (Table IV).

TABLE IV

DISTRIBUTION OF INHIBITORY 250 kD AND 35 kD PROTEIN FRACTIONS

| Protein Source | Total Protein ($\mu m^2$) | 3T3 Spreading on Liposomes From: | |
|---|---|---|---|
| | | 250 kD Fraction ($\mu m^2$) | 35 kD Fraction ($\mu m^2$) |
| CNS white matter | 211 ± 60 | 158 ± 45 | 242 ± 51 |
| CNS gray matter | 845 ± 106 | 362 ± 65 | 460 ± 55 |
| Optic nerve culture | 240 ± 67 | 272 ± 52 | 332 ± 58 |
| Sciatic nerve culture | 1,623 ± 173 | 1,850 ± 250 | 1,261 ± 141 |
| Trout CNS myelin | 1,050 ± 110 | 1,150 ± 135 | 1,585 ± 185 |

*Protein (source) amounts were 100 $\mu$g (total protein liposomes) and 500 $\mu$g (gel-applied protein). Sample preparation was as described supra in the Materials and Methods section. Tested protein, if not indicated otherwise, was obtained from rat tissues.

Gray matter-derived liposomes contained markedly less nonpermissive activity. Significantly, high quantities of inhibitory activity were extracted from optic nerve-derived cell cultures. Such cultures contain highly nonpermissive, myelin marker-positive oligodendrocytes (see Section 6.2.1., supra). Analogous protein fractions from a Schwann cell-containing culture yielded no inhibitory proteins. Thus, nonpermissive substrate activity in the nervous system, as detected by our assay, codistributes with CNS white matter and with myelin-forming oligodendrocytes.

7.3. DISCUSSION

In this study, we have determined what makes rat CNS myelin a poor substrate. We first showed that brief treatment of the myelin with protease abolished nonpermissiveness, demonstrating the involvement of protein. These proteins require detergent to be separated from the myelin membranes. Solubilized myelin protein reconstituted with a phosphatidylcholine/phosphatidylserine mixture yielded liposomes with highly nonpermissive substrate properties. Liposomes with such unfavorable substrate properties were obtained from rat CNS myelin protein but not from the protein constituents of membrane fractions possessing permissive substrate properties (PNS myelin, liver). We, therefore, assume that nonpermissiveness is due to the same protein(s) in myelin and in myelin-derived liposomes. When myelin proteins were fractionated by SDS-PAGE, protein fractions with relative molecular masses of )35 kD and 250 kD were found to yield highly nonpermissive liposomes upon reconstitution. Furthermore, nonpermissive kD and 250 kD protein fractions could not be found in rat PNS myelin nor in a liver-derived membrane fraction. Therefore, the presence of nonpermissive 35 kD and 250 kD proteins and nonpermissive membrane fractions are correlated. Both protein fractions can function independently.

We have determined that the presence of the 35 kD and 250 kD proteins from CNS myelin can be sufficient to generate a nonpermissive substrate by combining them with otherwise permissive substrate fractions. Thus, not only is nonpermissiveness of depleted rat CNS myelin restored (not shown), but supplemented liver or siatic nerve protein-derived liposomes become nonpermissive (FIG. 12). We therefore conclude that 35 kD and 250 kD proteins of rat CNS myelin are likely to be responsible for its nonpermissive substrate properties and that these proteins can be considered inhibitors of fibroblast spreading and of neurite outgrowth. Proof that the proteins are indeed the cause of CNS white matter nonpermissiveness was obtained by use of specific blocking antibodies; such antibodies neutralized the nonpermissiveness of gel-purified inhibitors-containing liposomes, of CNS myelin membranes, and of living cultured oligodendrocytes (as described in Section 8, infra).

8. ANTIBODY AGAINST MYELIN-ASSOCIATED INHIBITOR OF NEURITE GROWTH NEUTRALIZES NONPERMISSIVE SUBSTRATE PROPERTIES OF CNS WHITE MATTER

The examples described herein (Caroni and Schwab, March 1988, Neuron 1:85–96) demonstrate that an inhibitory substrate mechanism prevents neurites from growing into optic nerve explants in vitro, over living, cultured oligodendrocytes, and over myelin used as a culture substrate.

CNS white matter from higher vertebrates and cultured differentiated oligodendrocytes are nonpermissive substrates for neurite growth and fibroblast spreading. Monoclonal antibodies, termed IN-2 and IN-1, were raised against 35 kD and 250 kD proteins respectively with highly nonpermissive substrate properties extracted from CNS myelin fractions. IN-1 and IN-2 bound both to the 35 kD and 250 kD inhibitors and to the surface of differentiated cultured oligodendrocytes. Adsorption of nonpermissive CNS myelin or nonpermissive oligodendrocytes with either antibody markedly improved their substrate properties. Optic nerve explants injected with IN-1 or IN-2 allowed axon ingrowth of cocultured sensory and sympathetic neurons. We conclude that the nonpermissive substrate properties of CNS white matter are due to these membrane proteins on the surface of differentiated oligodendrocytes and to their in vivo product, myelin.

8.1. EXPERIMENTAL PROCEDURES

8.1.1. CELL CULTURE

Mouse NIH 3T3 cells were cultured and assayed for spreading behavior in DMEM containing 10% FCS. SCGs from newborn rats were dissected and dissociated into single cells as described (Mains and Patterson, 1973, J. Cell. Biol. 59:329–345; Schwab and Thoenen, 1985, J. Neurosci. 5:2415–2423). Neurons were cultured in an enriched L15 medium (Mains and Patterson, supra) with 5% rat serum and 100 ng/ml of 2.5S NGF. Overgrowth by non-neuronal cells was prevented by inclusion of cytosine arabinoside ($10^{-5}$ M) in the culture medium. Inhibitory oligodendrocyte-containing cultures were prepared from the optic nerves of 8–10 day old rats as described (see Section 6.1.1., supra). Optic nerve cultures were maintained in an enriched L15 medium with 5% rat serum. P3U myeloma cells and their hybridomas were cultivated in Iscove medium supplemented with glutamine, antibiotics, $10^{-4}$ M β-mercaptoethanol, and 10% human serum.

8.1.2. SUBSTRATE PREPARATION

Myelin fractions were isolated as described in Section 6.1.5., supra). Briefly, carefully cleaned adult rat spinal cord tissue (CNS myelin) or rat sciatic nerve (PNS myelin) was homogenized in isotonic sucrose buffer with a polytron homogenizer, and myelin membrane fractions were obtained by flotation of low speed supernatants to densities below that of 0.85 M sucrose (Colman, et al., 1982, J. Cell Biol. 95:598–608). All isolation media contained trasylol (100 U/ml), 5 mM iodoacetamide, and 5 mM EDTA to reduce protease digestion (this reagent mixture is designated herein as protease inhibitors). Finally, myelin fractions were washed hypotonically in 30 mM Hepes (pH 7.4) (medium A) plus protease inhibitors and frozen in aliquots at –80° C. To prepare protease-digested myelin membranes, the myelin was washed in medium A without protease inhibitors and subsequently incubated at a concentration of 1 mg/ml in the presence of 0.1% trypsin (Sigma). After 10 minutes at room temperature, 0.2% trypsin inhibitor (Sigma) was added and membranes were washed free of protease in medium A. Oxidative chemical deglycosylation of myelin membranes was performed by the periodate method as described (Beeley, 1985, in Laboratory Techniques in Biochemistry and Molecular Biology, R. H. Burdon and P. H. Van Knippenberger, eds., Elsevier, Amsterdam, pp. 279–288).

Liposomes containing myelin membrane proteins were prepared by the cholate dialysis method (see Section 7.1.4, supra). Briefly, solubilized protein was precipitated in a 10-fold excess volume of ice-cold acetone. Precipitated protein was collected by centrifugation after a 15 hour incubation at 4° C. and resuspended in 2.5% cholate in medium A. A 5- to 50-fold excess (v/v) of phospholipids (phosphatidylcholine/phosphatidylserine, 10:1) in medium A plus 2.5% cholate was then added to the solubilized protein. The lipid-protein mixture was applied to a Sephadex G50 column equilibrated in medium A and liposomes were collected in the void volume. When membrane fractions were used as protein source, precipitated protein was resuspended at approximately 1 mg/ml, while gel-extracted protein was resuspended at approximately 50 μg/ml.

Gel extraction of inhibitory proteins from CNS myelin was performed as described (see Section 7.1.5, supra). Myelin protein was fractionated on 3%–15% gradient gels under reducing conditions. For this purpose, samples were preincubated for 30 minutes at room temperature in SDS-PAGE sample buffer containing 2% SDS and β-mercaptoethanol. Protein from gel regions to be analyzed was extracted in the presence of 0.5% SDS and 50 μg/ml insulin (Sigma). The latter was included to reduce losses due to adsorption of protein from low concentration solutions. The added insulin was removed from the protein to be tested by the Sephadex G50 column (liposome formation procedure). When gel-extracted protein was used as immunogen, no insulin was included in the gel extraction medium.

8.1.3. IMMUNOLOGICAL METHODS

The following antisera and monoclonal antibodies were used in this study; anti-N-CAM (neural cell adhesion molecule) antiserum (gift of M. Schachner, Heidelberg, FRG), anti-tenascin antiserum (gift of R. Chiquet-Ehrismann, Basel, Switzerland), anti-J1 antiserum (gift of M. Schachner), monoclonal antibodies $O_4$ (anti-sulfatide) and $O_1$ (anti-galactocerebroside)(gifts of M. Schachner).

Anti-CNS myelin antiserum was produced in rabbits by the injection of 200 μg of myelin protein per immunization step. The cold-soluble fraction of the antiserum was heat-inactivated by incubation at 56° C. for 1 hour.

To produce anti-inhibitory substrate monoclonal antibodies, BALB/c mice (6 week old females) were injected with approximatly 50 μg of gel-extracted inhibitory (35 kD or 250 kD) fraction from rat CNS myelin. Gel-extracted protein was precipitated in acetone and resuspended at 1 mg/ml in sterile PBS plus 0.1% cholate. Mice were immunized twice at 3 week intervals, sera were tested for production of nonpermissiveness-neutralizing antibodies (see also below), and mice with strong neutralizing sera were used for hybridoma production.

8.1.3.1. RADIOIMMUNOASSAY

Antibody presence was detected by a solid phase radioimmunoassay (Carlson and Kelly, 1983, J. Biol. Chem. 258:11082–11091) using $^{125}$I-labeled goat anti-mouse antibody (Bio-Rad) as a probe.

Wells of 96 well plates were coated by exposing them to appropriate antigen (2 μg of protein per ml of 30 mM Tris [pH 7.4], 160 mM NaCl [Tris-saline]; 50 μl per well) for at least 3 hours at room temperature. Coated wells were then washed in Tris-saline plus 1% BSA, incubated in the presence of the hybridoma supernatants, and finally assayed for the presence of bound antibody with $^{125}$I-labeled goat anti-mouse antibody (approximately $10^5$ cpm per well). Values obtained with different antigens cannot be compared quantitatively, as adsorption to the wells varied among different antigens. Background values for goat anti-mouse binding in the absence of mouse antibodies were routinely subtracted. Signals of less than 2 times background values (100–150 cpm) were considered nonsignificant.

8.1.3.2. IMMUNOBLOTS

Transfer of CNS myelin protein fractionated by SDS-PAGE onto nitrocellulose was performed in 50 mM sodium phosphate buffer (pH 5.5), 2 mM EDTA, 0.05% SDS (Filbin, M. T. and Poduslo, S. E., 1986, Neurochem. Int. 9:517–520). Transfer time was 3 hours at 1.6 A. Incubation procedures with antibodies and $^{125}$I-labeled second antibody followed standard procedures. Antibody-binding protein bands were visualized by autoradiography using high sensitivity Kodak X-ray films (X-OMAT).

Preparation of cell cultures for immunofluorescence microscopy was performed as follows. Cultures were rinsed in PBS and pre-fixed at 37° C. with fixation medium containing 4% paraformaldehyde. Upon extensive rinsing with PBS, cultures were incubated with the first antibody for 45 minutes at room temperature (antibody dilutions, 1:50 for antisera and ascites; 1:3 for hybridoma supernatants; dilution buffer consisted of isotonic, sucrose-containing phosphate buffer (pH 7.4) plus 5% BSA). Unbound antibody was removed with 5% BSA-containing medium. After thus staining the cells with monoclonal antibodies, the cells were incubated with a 1:50 dilution (in 5% BSA-containing medium) of the second antibody, a rabbit anti-mouse antibody (SAKO, Copenhagen, Denmark) in 5% BSA-containing medium. The rabbit anti-mouse incubation enhanced signal intensities and was performed for 30 minutes at room temperature. Cells were then fixed in isotonic buffer containing 4% paraformaldehyde. Fixation was interrupted after 30 minutes. Upon incubation with appropriate fluorescently labeled second antibody and subsequent washes in dilution buffer, bound antibody was visualized on an Olympus Vanox fluorescence microscope. Control experiments with hybridoma medium were performed to exclude nonspecific fluorescent signals. Highly branched oligodendrocytes or HBOs were identified by their characteristic morphology and by double labeling experiments with the antibody $O_1$ (see Section 6.1.3 supra).

Laminin was visualized by indirect immunofluorescence using a rabbit antiserum against EHS-tumor laminin on frozen sections of freshly dissected adult rat optic and sciatic nerves and on sections of nerves after 4 weeks in culture (see below).

Immunoprecipitation of IN-1-binding (and of IN-2-binding) proteins was performed in immunoprecipitation buffer consisting of 150 mM NaCl, 30 mM Hepes (pH 8.2), 2% NP40™, 0.5% sodium deoxycholate, plus protease inhibitors. Antibody was bound either to solubilized CNS myelin protein (solubilization in immunoprecipitation buffer for 1 hour at 4° C.) or to intact myelin membranes. In both cases, 100 µg of myelin protein was incubated with 1 ml of hybridoma supernatant for 1 hour at room temperature. Myelin membranes incubated in the presence of antibody were washed twice in medium A and solubilized in immunoprecipitation buffer. Rabbit anti-mouse was added in both 3.5 immunoprecipitation protocols to solubilized antigen-antibody complex (20 µg of rabbit anti-mouse per ml of hybridoma supernatant), and incubation was allowed to proceed for an additional 1 hour period at room temperature. Antigen-antibody-rabbit anti-mouse complex was finally sedimented with *S. aureus* cells (Sigma). Elution was performed by boiling for 5 minutes in 100 mM ammonium chloride (pH 11.5) plus 0.5% SDS and β-mercaptoethanol. This procedure irreversibly inactivated present antibodies. Eluted, neutralized antigen was precipitated with acetone and assayed for its substrate properties upon reconstitution into liposomes.

8.1.4. SUBSTRATE TESTING PROCEDURES

Substrates were tested as described in Section 7.1.2 supra). Myelin fractions or liposomes in medium A were dried onto the wells of polylysine-coated Greiner dishes (Greiner, Murtingen, FRG). Unbound membranes were removed by 3 washes in $Ca^{2+}$- and $Mg^{2+}$-free Hank's medium, and substrate-testing cells, i.e., 3T3 fibroblasts or superior cervical ganglian SCG neurons, were immediately added to the dishes. When substrates were tested in the presence of antibody, bound substrates were incubated in the presence of undiluted hybridoma supernatants or in the presence of 1:30 dilutions (in Hank's medium) of antisera. After 15 minutes at 37° C., four-fifths of the antibody-containing medium was removed and substituted with cell-containing medium. An analogous preincubation procedure was used in experiments aimed at testing HBO nonpermissiveness. 3T3 experiments were usually scored after a culture period of 1 hour, whereas SCG neurons were allowed to grow processes for 24 hours in culture. When 3T3 cells were preincubated with hybridoma supernatant, incubations were performed in gently agitated suspensions for a period of 15 minutes at room temperature. Cells were then sedimented, resuspended in culture medium, and added to substrate-adsorbed Greiner dish wells. 3T3 cells were added at a density of 30,000 cells per $cm^2$, and SCG neurons were added at a density of 20,000 cells per $cm^2$.

Quantitative evaluation of spreading was performed with a surface integration program on at least 30 cells per experimental point. Photographs of randomly selected fields were used for this purpose, and the outlines of all spread cells present in the field were traced manually with a graphic stylus connected to a computer. Only spread cells were considered, and a zero-spreading value (strongly refractory and round cells) was subtracted. Experiments were found to be subject to only small quantitative variations, and values from representative experiments are given. Spreading degrees are given as means plus or minus standard error of the mean.

Quantitative evaluation of HBO inhibition of fibroblast spreading was performed by determining areas of overlap between $O_1^+$ oligodendrocytes and 3T3 fibroblasts 1–2 hours after the addition of 3T3 cells to a 2 day old optic nerve culture. The ratio of 3T3-oligodendrocyte overlap to the total area of oligodendrocytes was compared with the proportion of the total examined culture area occupied by 3T3 cells. Zero inhibition was defined as the absence of apparent discrimination by spreading fibroblasts against surface occupied by oligodendrocytes.

8.1.5. NEURITE GROWTH INTO OPTIC NERVE EXPLANTS IN VITRO

Optic nerves of young adult rats were cultured together with dissociated rat sympathetic or sensory neurons as previously described (Schwab and Thoenen, 1985, J. Neurosci. 5:2415–2423). Briefly, optic nerves were rapidly dissected from 6–8 week old female rats, cleaned from adhering meninges, and injected from both sides using a 10 µl Hamilton syringe with 2 µl of either IN-1 or IN-2 hybridoma supernatant or (controls) with $O_1$ hybridoma supernatant or antibody-free hybridoma medium. A Teflon ring with silicon grease separated the three chambers, and optic nerves were placed through the silicon grease, reaching from the middle chamber into one or the other side chamber. The respective antibodies were present in the side chambers at a dilution of 1:10 throughout the culture period. Dissociated newborn rat SCG or dorsal root ganglion neurons were plated in the central chamber in L15 medium with rat serum and NGF, thus having access to one end of both nerves. After 3 weeks in culture, cultures were fixed with 2.5% glutaraldehyde and disassembled. The nerve explants were separately embedded in EPON. Sections for electron microscopy were cut from three regions of each nerve; within the first 1 mm in the central chamber, from the region of the nerve under the Teflon ring, and at a distance of 3 mm from the central chamber end of the nerve (side chamber region). Most of the sections comprised the entire nerve in cross sections; they were sytematically screened for the presence of axons using electron microscopy.

8.2. RESULTS

8.2.1. ANTISERUM AGAINST MYELIN NEUTRALIZES THE NONPERMISSIVE SUBSTRATE EFFECTS OF CNS MYELIN AND AND OF HBOs

Antisera were generated against rat CNS myelin and adsorbed to polylysine-bound myelin. The antibody-adsorbed myelin was then assayed for its substrate properties in supporting fibroblast spreading. The antiserum contained antibodies that neutralized CNS myelin nonpermissiveness. Nonimmune rabbit serum did not significantly modify myelin substrate properties. In these experiments, care was taken to, first, heat-inactivate rabbit serum fractions in order to prevent highly toxic complement reaction and, second, to deplete the same fractions of cold-insoluble proteins, which included fibronectin as a strong promoter of fibroblast spreading and attachment. The antiserum was also very effective in neutralizing HBO nonpermissiveness. Neutralization was specific, as rabbit antiserum against tenascin (Chiquet-Ehrismann et al., 1986, Cell 47:131–139) (FIGS. 14A–F), N-CAM (neural cell adhesion molecule), and J1 (Kruse et al., 1985, Nature, 316:146–148) did not influence myelin or HBO substrate properties. The cell adhesion molecules N-CAM and J1 were present in substantial amounts on the surface of HBOs as detected by immunofluorescence. Tenascin antigenicity was absent from the myelin (shown by radioimmunoassay) as well as from the HBO surface (shown by immunofluorescence). This finding is important as it demonstrates that the documented, unfavorable substrate properties of tenascin (Chiquet-Ehrismann et al., 1986, Cell 47:131–139) are not responsible for myelin or HBO substrate properties. The experiments with myelin-antiserum demonstrated that the properties of both tested substrates, myelin and oligodendrocytes, could be improved by antibody binding.

8.2.2. IN-1: A MONOCLONAL ANTIBODY AGAINST GEL-PURIFIED 250 kD INHIBITOR FRACTION FROM CNS MYELIN NEUTRALIZES MYELIN NONPERMISSIVENESS

Mice were immunized with rat CNS myelin 250 kD protein fraction, hybridomas were raised, and supernatants were screened for anti-myelin antibodies. Positives were rescreened for neutralization of CNS myelin nonpermissiveness by the 3T3 cell spreading assay. Five myelin-positive antibodies fulfilled the second screening criterion to varying degrees. The antibody with the strongest neutralizing properties was selected and designated IN-1.

Adsorption of liposomes containing the 250 kD protein, liposomes containing the 35 kD protein, and rat CNS myelin with IN-1 drastically reduced nonpermissiveness in all three cases (FIGS. 13A–H). Neutralization was slightly less efficent for CNS myelin membranes (FIGS. 13A and 13B), possibly due to incomplete saturation of inhibitory sites by the antibody. The antibody bound to inhibitor-containing liposomes and to CNS myelin, but not to PNS myelin (Table V).

TABLE V

IN-1 BINDS TO 35 kD AND 250 kD MEMBRANE PROTEINS FROM RAT CNS MYELIN*

| Antigen | (Amount of Antibody Bound cpm of $^{125}$I-Labeled Goat Anti-Mouse) | | |
|---|---|---|---|
| | IN-1 | 1G9** | O1** |
| CNS myelin: | | | |
| Control | 550 ± 35 | 1500 ± 110 | 10850 ± 550 |
| Trypsin-treated | 25 ± 20 | 40 ± 30 | 8200 ± 480 |
| PNS myelin: | 80 ± 25 | 350 ± 30 | 9200 ± 500 |

TABLE V-continued

IN-1 BINDS TO 35 kD AND 250 kD MEMBRANE PROTEINS FROM RAT CNS MYELIN*

| Antigen | (Amount of Antibody Bound cpm of $^{125}$I-Labeled Goat Anti-Mouse) | | |
|---|---|---|---|
| | IN-1 | 1G9** | O1** |
| Liposomes containing: | | | |
| 250 kD CNS myelin protein | 250 ± 30 | 45 ± 20 | 80 ± 50 |
| 35 kD CNS myelin protein | 350 ± 35 | 40 ± 30 | 90 ± 60 |

*Antibody binding sites were detected by a solid phase radioimmunoassay using $^{125}$I-labeled goat anti-mouse antibody as a probe. Liposomes were prepared from gel-extracted CNS myelin protein (100 μg of myelin protein added to the gel). Values are given after subtraction of background binding in the absence of primary antibody. Background values for liposomes were essentially identical to the ones obtained with antibody in the presence of protein-free liposomes, i.e., approximately 120–150 cpm.
**Antibody 1G9 is an anti-myelin monoclonal antibody that binds to the surface of differentiated oligodendrocytes and to protein of 110 kD on Western blots of rat CNS myelin.

Neutralization of inhibitory substrate properties of myelin fractions was observed for superior cervical ganglion (SCG) neurons (FIGS. 13A–h), for 3T3 fibroblasts (see Table VI), and for neuroblastoma cells in the presence of dibutyryl-cAMP.

TABLE VI

IN-1 NEUTRALIZES NONPERMISSIVENESS OF CNS MYELIN AND ITS SPREADING INHIBITORS OF 35 kD AND 250 kD*

| | 3T3 Spreading ($\mu m^2$) | | |
|---|---|---|---|
| Substrate | Control | +IN-1 | O1 |
| CNS myelin | 278 ± 31 | 1446 ± 114 | 250 ± 36 |
| 250 kD liposomes | 213 ± 11 | 1335 ± 151 | 245 ± 35 |
| 35 kD liposomes | 185 ± 18 | 1286 ± 113 | 210 ± 21 |
| Protein-free liposomes | 1520 ± 145 | 1410 ± 105 | 1495 ± 145 |

*Spreading extents were estimated after 1 hour in culture in the presence or the absence of hybridoma supernatant. Substrate protein amounts adsorbed to the wells of Greiner dishes were as follows:
CNS myelin, 20 μg per cm$^2$;
liposomes, 100 μg of CNS myelin protein were applied to the gel lane from which proteins of indicated apparent molecular weight were extracted, and the entire extracted and reconstituted protein was applied to the culture well. Apparent molecular weight ranges were estimated with molecular weight standards (Bio-Rad) and were about 35 ± 3 kD and 250 ± 15 kD, respectively.

protein-free lipid vesicle, or on permissive liposomes containing peripheral 250 kD protein (see FIGS. 13A–H). In these latter cases, cell attachment and spreading were slightly impaired, but no improvement was obtained with IN-1, demonstrating the specificity of the antibody effect for neutralizing myelin-derived inhibitors. Neutralization was due to the antibody fraction in IN-1-containing supernatants, as an ammonium sulfate-precipitated fraction of IN-1 ascitic fluid was equally effective.

IN-1 binding is completely abolished by a brief pretreatment of the myelin with trypsin, demonstrating that the antibody does not bind to glycolipids (Table V). IN-1 antibody when preadsorbed onto HBO-containing cultures also efficiently reduced HBO nonpermissiveness (see FIGS. 14A–F). In control experiments, 3T3 cells never invaded more than 10% of the surface of $O_1^+$ (galactocerebroside; marker for differentiated oligodendrocytes) HBOs. Fibroblasts seeded directly onto HBOs failed to spread and eventually detached. Often more than 50% of HBO surface was covered by fibroblasts in the presence of IN-1. In addition, spreading of fibroblasts on antibody-adsorbed HBOs was frequently observed (FIGS. 14A–F). Interestingly, quantitative determination of the substrate properties of HBOs in the presence of IN-1 showed that 3T3 cells prefer HBOs over the polylysine-coated culture dish under this condition (FIGS. 14A–F). This behavior could be related to the presence of cell adhesion molecules like myelin associated glycoprotein, J1, or N-CAM on these oligodendrocytes. FIG. 16 also shows that IN-1 bound to the surface of living HBOs. Specific staining of intact cells with the morphology of astrocytes, fibroblasts, or immature, $A_2B_5^+$ oligodendrocytes was not detected by our method. Also, no specific IN-1 staining could be detected on the surface of living neuronal cells or neuroblastoma cells. The observed weak staining of HBOs was probably due to the fact that spreading inhibitors are minor proteins in myelin and optic nerve culture fractions. These experiments demonstrate that nonpermissiveness in HBOs is, as previously shown for myelin, an IN-1-affected process.

8.2.3. 250 kD AND 35 kD INHIBITORS FROM CNS MYELIN SHARE TWO NEUTRALIZING EPITOPES

As shown in Table VI, IN-1 did bind to liposomes containing the 35 kD inhibitor. Therefore, the epitope defined by IN-1 is shared between the 250 kD and 35 kD inhibitors (see also FIG. 16). Such an epitope may be a polypeptide since treatment of the myelin with periodate to remove carbohydrate did not affect IN-1 binding. Table VI demonstrates that the 35 kD inhibitor was neutralized by IN-1. As the antibody neutralized the inhibitory substrate properties of myelin membranes, these experiments are consistent with the interpretation that both the 250 kD and the 35 kD inhibitor contribute to myelin nonpermissiveness.

Control experiments (Table VI) excluded that IN-1 neutralization was due to nonspecific masking of the myelin as a consequence of antibody binding, as monoclonal antibodies $O_1$ and $O_4$, which bind to very abundant antigens on the surface of myelin and HBOs, did not reduce the nonpermissive substrate effects of either myelin (Table VI, for $O_1$) or living HBOs (FIG. 15, for $O_4$).

Immunization experiments, as previously described for the 250 kD protein, were performed with the gel-purified kD inhibitor fraction from rat CNS myelin, confirming the relatedness of the 250 kD and 35 kD myelin inhibitors. Hybridomas produced from such mice were tested as described for monoclonal antibody IN-1. The strong neutralizing antibody IN-2 was selected. Neutralization and binding properties of IN-2 are summarized in Table VII.

TABLE VII

IN-2 BINDS TO CNS MYELIN INHIBITORY SUBSTRATES AND NEUTRALIZES THEIR NONPERMISSIVE SUBSTRATE PROPERTIES*

| Antigen/Substrate | IN-2 Binding ($^{125}$I-Labeled Goat Anti-Mouse cpm) | 3T3 Spreading ($\mu m^2$) | |
|---|---|---|---|
| | | No IN-2 | +IN-2 |
| CNS myelin | 975 | 245 ± 15 | 1300 ± 121 |
| CNS myelin, trypsin-treated | 100 | 1485 ± 110 | 1430 ± 158 |
| CNS myelin liposomes | 700 | 180 ± 18 | 1040 ± 110 |
| 35 kD liposomes | 285 | 215 ± 15 | 1250 ± 120 |
| 250 kD liposomes | 410 | 205 ± 11 | 1180 ± 108 |
| Protein-free liposomes | 100 | 1385 ± 125 | 1420 ± 160 |

*Experimental details are described supra in Experimental Procedures and Tables V and VI. Data presented in the table were obtained with a 1:100 dilution (in PBS) of ammonium sulfate-precipitated antibody from ascitic fluid (10 $\mu$g of protein per ml after dilution). CNS myelin liposomes were formed from 20 $\mu$g of CNS myelin protein Thus, IN-2 bound to both the 35 kD and the 250 kD protein, it neutralized nonpermissiveness of myelin membranes and HBOs, and it bound to the surface of living HBOs. IN-1 and IN-2 epitopes are not identical: IN-2, but not IN-1, strongly bound to cytoskeleton-associated antigens when astrocytes or fibroblasts were permeabilized. As found for IN-1, IN-2 did not bind to protease-treated myelin.

8.2.4. IN-1 SPECIFICALLY IMMUNOPRECIPITATES NONPERMISSIVE SUBSTRATE ACTIVITY FROM SOLUBILIZED MYELIN PROTEIN

Since the inhibitory protein fractions used in this study apparently contained more than one protein species, immunoprecipitation experiments were performed to determine whether IN-1 binds directly to neurite growth- and fibroblast spreading-preventing protein(s).

Solubilized myelin protein was adsorbed with IN-1 antibody, and antigen-antibody complex was sedimented with rabbit anti-mouse bound to Staphylococcus aureus cells. Antigen-antibody complexes were then dissociated under denaturing and reducing conditions to irreversibly inactivate the IN-1 antibody. Liposomes formed in the presence of immunoprecipitated protein were highly inhibitory for fibroblast spreading (Table VIII).

TABLE VIII

IN-1 SPECIFICALLY REMOVES INHIBITORY SUBSTRATES FROM CNS MYELIN PROTEIN, INHIBITORY PROTEINS OF 35 kd AND 250 kd ARE IMMUNOPRECIPITATED BY IN-1*

| Myelin Protein Fraction | 3T3 Spreading ($\mu m^2$) | |
|---|---|---|
| | Protocol 1 | Protocol 2 |
| Total | 322 ± 32 | 255 ± 25 |
| IN-1-depleted | 1361 ± 61 | 1280 ± 90 |
| $O_1$-depleted | 612 ± 63 | ND |
| IN-1-immunoprecipitated | 218 ± 16 | 215 ± 18 |
| $O_1$-immunoprecipitated | 1218 ± 108 | 1410 ± 128 |

TABLE VIII-continued

IN-1 SPECIFICALLY REMOVES INHIBITORY SUBSTRATES
FROM CNS MYELIN PROTEIN, INHIBITORY PROTEINS
OF 35 kd AND 250 kd ARE IMMUNOPRECIPITATED BY IN-1*

|  | 3T3 Spreading ($\mu m^2$) | |
| --- | --- | --- |
| Myelin Protein Fraction | Protocol 1 | Protocol 2 |
| From IN-1-precipitated: | | |
| 250 kD liposomes | ND | 245 ± 18 |
| 35 kD liposomes | ND | 270 ± 21 |

*Details of immunoprecipitation protocols are given in Section 8.1.3.2., supra.
Protocol 1: immunoprecipitation from solubilized CNS myelin protein.
Protocol 2: immunoprecipitation upon binding of antibody to intact myelin membranes and subsequent solubilization of antigen-antibody complexes. In both protocols, immunoprecipitation was performed using 100 $\mu g$ of CNS myelin protein. Total refers to liposomes formed from 1% of the starting material. Liposome fractions designated depleted were formed from 1% of the immunoprecipitation supernatant. Those designated immunoprecipitated were formed from 5% of the immunoprecipitated and eluted material. Finally, in the experiments presented in the second part of the table, IN-1-immunoprecipitated protein (from 500 $\mu g$ of starting CNS myelin protein) was separated by SDS-PAGE, and gel regions of indicated apparent molecular weight were extracted from the gel and reconstituted as described in Section 8.1.3.2., and previous tables. In these cases, liposomes supra corresponding to 5% of the gel-extracted protein were adsorbed to the 1 $cm^2$ wells.
ND, not determined.

In control experiments, both $O_1$ antibody (Table VIII) and a monoclonal antibody against 110 kD myelin protein did not immunoprecipitate inhibitory substrate.

Immunoprecipitation of inhibitory substrate with IN-1 could also be performed when antibody was first bound to myelin membranes (Table VIII). In the latter case, membranes were subsequently washed free of unbound antibody, myelin protein was solubilized, and antigen-antibody complex was sedimented as described above. This experiment demonstrated that the inhibitory substrate-associated IN-1 epitope(s) was accessible to antibody in its native myelin membrane location. When immunoprecipitated proteins were subsequently separated by SDS-PAGE, inhibitor-containing protein fractions of 35 kD and of 250 kD could be extracted from the gel (Table VIII). Therefore, 35 kD and 250 kD inhibitors of neurite growth and fibroblast spreading expose the IN-1 epitope on the surface of myelin membranes.

FIG. 16 shows that IN-1 binding to CNS myelin proteins fractionated by SDS-PAGE and adsorbed onto nitrocellulose was restricted to a subset of minor myelin proteins. While binding to 250 kD protein was consistently observed, binding to protein in the 35 kD region was weak and often not detectable. In addition, IN-1 bound to 56 kD protein, which had not previously been recognized as yielding inhibitory liposomes upon reconstitution. When myelin fractions yielding strong IN-1[+] 56 kD protein were used as the source of gel-purified 56 kD protein, highly inhibitory liposomes were obtained upon reconstitution. While essentially no binding of IN-1 to intact, permissive PNS myelin membranes could be observed (Table V), Western blot analysis of PNS myelin protein with IN-1 revealed immunoreactive material of 300–400 kD. Upon gel extraction and reconstitution, this latter material yielded liposomes with permissive substrate properties. Masking of a hypothetical inhibitory substrate by highly favorable substrate from the same 300–400 kD PNS myelin protein region cannot be excluded. However, attempts to immunoprecipiate inhibitory substrate from solubilized PNS myelin protein with IN-1 have failed. It therefore seems reasonable to assume that the antibody IN-1 also binds to proteins with no inhibitory substrate properties. Therefore, identification of inhibitory substrates by Western blot analysis with the antibody IN-1 is presently not warranted.

8.2.5. NONPERMISSIVENESS OF ADULT OPTIC NERVE IS NEUTRALIZED BY ADSORPTION WITH IN-1 ANTIBODY

Optic nerve explants, in contrast to sciatic nerve explants, have been observed not to support growth of neurites in vitro, even when optimal amounts of appropriate neurotrophic factor was present (Schwab and Thoenen, 1985, J. Neurosci. 5:2415–2423). Cultured optic nerve explants were assayed for laminin immunoreactivity as neurite growth is known to be supported by laminin and furthermore since laminin is known to be present in sciatic nerve but not in optic nerve in situ. Laminin was exclusively present on the pial basement membrane and around blood vessels when freshly dissected optic nerve from adult rat was analyzed. The explant, however, contained substantial amounts of strongly laminin-positive cells, presumably astrocytes, after 3–4 weeks in vitro (FIGS. 17A–B). Despite the presence of laminin, no neurites were found to grow into optic nerve after periods of up to 5 weeks in vitro. These findings supported the interpretation that a nonpermissive substrate present in the optic nerve explants is responsible for its unfavorable microenvironment.

In subsequent experiments, IN-1 antibody was injected into the optic nerve explant prior to insertion of the explant in a three-compartment chamber culture system (Schwab and Thoenen, 1985, J. Neurosci. 5:2415–2423). In addition, IN-1-containing supernatant was also added to the compartment containing the distal end of the nerves for the duration of the experiment. In control experiments, supernatants rich in $O_1$ antibody were injected and included in the culture medium.

The results from these experiments demonstrated that IN-1, but not $O_1$ antibody, effectively promoted extensive growth of sympathetic and sensory neurites into the optic nerves (Table IX, FIGS. 18A–B).

TABLE IX

INJECTION OF OPTIC NERVE EXPLANTS WITH
ANTIBODY IN-1 RESULTS IN INGROWTH OF
AXONS INTO OPTIC NERVE IN VITRO*

|  | Antibody IN-1 Optic Region | | Antibody $O_1$ Optic Region | |
| --- | --- | --- | --- | --- |
| Culture | 1 mm | 3 mm | 1 mm | 3 mm |
| 1 | +++ | +++ | ++ | − |
| 2 | ++ | +++ | + | + |
| 3 | ++ | +++ | + | + |
| 4 | ++ | ++ | + | − |
| 5 | +++ | +++ | | |
| 6 | ++ | ++ | − | − |

*Optic nerve explants were injected with antibody IN-1 or antibody $O_1$ and then placed into chamber cultures with sensory neurons in the central chamber. After 3 weeks in culture, nerves were systematically examined by electron microscopy. Presence of axons at 1 and 3 mm in the optic nerves of representative experiment.
+ indicates 1–20 axons;
++: 20–50 axons;
+++: >50 axons per cross section.
Large numbers of axons were found deep in the IN-1-injected nerves, but not in the $O_1$-injected nerves.

Neurites extended for lengths of more than 3 mm into optic nerves in the presence of IN-1 (Table IX). Although preferred as a substrate, growth was not restricted to regions adjacent to basal membrane, and contact of ingrowing neurites with myelin could frequently be observed (FIGS. 18A–B). In some experiments, damaged control nerves with large tissue-free spaces did allow limited neurite growth. In those cases, however, neurites were not found in contact with myelin sheets. Neurite growth over a distance of 3 mm into the optic nerves was observed in 5 out of 6 cases when IN-1 was present. Growth in $O_1$-containing nerve was observed in 1 out of 5 cases (Table IX).

These findings strongly suggest that nonpermissiveness of optic nerve explants in vitro is due to IN-1-binding inhibitory substrate. As 35 kD and 250 kD inhibitory substrates from CNS myelin are found in optic nerve tissue, these proteins are likely to be responsible for its nonpermissive microenvironment in vitro and possibly also in vivo.

8.3. DISCUSSION

The experiments described herein demonstrate that monoclonal antibodies raised against each gel-purified inhibitor fraction neutralized or greatly reduced the nonpermissiveness of both inhibitors, of isolated myelin membrane fractions, of cultured HBOs, and of adult rat optic nerve explants. The antibodies bind to the surfaces of myelin membranes and cultured oligodendrocytes. They specifically immunoprecipitate inhibitory substrate proteins of 35 kD and 250 kD from myelin protein fractions. We conclude that nonpermissiveness of adult CNS white matter-derived tissues, cells, and subcellular fractions is due to the same inhibitory substrate mechanism involving IN-1-binding (and IN-2-binding) proteins. Clearly, 35 kD and 250 kD inhibitors share two antigenic sites, IN-1 and IN-2. In both cases, antibody binding abolished nonpermissive substrate properties. Our data are consistent with the interpretation that the proteins reponsible for adult CNS white matter nonpermissiveness are the 35 kD and 250 kD (and 56 kD) inhibitory substrates extracted from rat CNS myelin.

9. INVOLVEMENT OF A METALLOPROTEASE IN GLIOBLASTOMA INFILTRATION INTO CENTRAL NERVOUS SYSTEM TISSUE IN VITRO

In the examples detailed herein, we describe a membrane-associated metalloprotease which plays a crucial role in the malignant tumor infiltration of CNS tissue in vitro by the rat glioblastoma cell line C6.

We have discovered that malignant tumor infiltration of CNS tissue in vitro by the glioblastoma line C6, requires a plasma membrane bound metallodependent degradative activity. C6 cells infiltrate optic nerve explants, attach and spread on white and grey matter of cerebellar frozen sections or on CNS myelin. The metal ions chelator 1,10-phenanthroline and the dipeptide cbz-tyr-tyr, but not inhibitors for three other classes of proteases, blocked up to 67% of C6 cell spreading on CNS myelin. A 0metallodependent activity neutralizing CNS myelin inhibitory substrate properties toward 3T3 cells, is associated with a C6 plasma membrane fraction. The same inhibitors of metalloprotease also impaired infiltration of CNS nerve explants and spreading on the CNS white matter of cerebellar frozen sections.

9.1. MATERIALS AND METHODS

9.1.1. CELL CULTURES

Rat C6, mouse NIH 3T3 and B16 cells were cultured in Dulbecco's modified Eagle's medium (DMEM) supplemented with 10% fetal calf serum (FCS), usually to maximally 70–80% confluency. Cells were harvested with a short trypsin treatment (0.1% in $Ca^{2+}/Mg^{2+}$-free Hank's medium for 90 seconds) stopped by addition of FCS in excess, collected by centrifugation. Cells were resuspended in either DMEM/FCS or defined serum-free medium (MEM) and used for experiments. Dissociated rat CNS glial cells were prepared starting from optic nerves of 6–7 days old Lewis rats as described in Section 6.1.1, supra and plated into poly-D-lysine (PLYS) coated wells (100 $mm^2$, 100 $\mu l$ medium) at a density of 20,000 cells per well. The culture medium was an enriched L15 medium with 5% rat serum, penicillin and streptomycin. C6, 3T3 and B16 cells were added to 2 day old cultures at a concentration of 30,000 cells per well, incubated for two hours and fixed with warm 4% formalin in phosphate buffer. Inhibitory oligodendrocytes were identified by double labelling using the specific antibodies $O_1$ and $O_4$ (see Section 6.1.3, supra).

9.1.2. PREPARATION OF NERVE EXPLANTS FOR INFILTRATION ASSAY

Optic nerve and sciatic nerve explants were prepared as described (Schwab and Thoenen, 1985, J. Neurosci. 5:2415–2423). Briefly, the nerves were rapidly dissected from about 8 week old male rats, cleaned from the meninges, 3 times frozen and thawed using liquid nitrogen, and placed under a teflon ring (diameter 13 mm, thickness 1 mm) sealed to a culture dish with silicon grease. Two chambers connected only by the explants were in this way obtained. 300,000 C6, 3T3 or B16 cells were plated in the inner chamber in DMEM/FCS and incubated for 5 to 20 days. The medium was changed every other day. Cultures were fixed overnight with 4% formalin. The nerve explants were mounted with Tissue-Tek, 10 to 15 $\mu m$ sections were cut in a cryostate and collected on gelatine coated cover slips. After drying at room temperature overnight, the sections were stained in 0.75% cresyl violet, and evaluated. The infiltrated cells were counted for each 0.1 mm of the explants, starting from the tip where cells were added. Due to the 15 day incubation, the explants were often different in diameter. Therefore, only the central part of the nerves (0.25 mm) were considered, since only this part of the explants presented a good histological quality. Inhibition experiments were performed with nerve explants previously injected from both sides with 2 $\mu l$ of 3 mM cbz-tyr-tyr or cbz-ala-phe solutions.

9.1.3. CNS FROZEN SECTIONS AND MYELIN AS SUBSTRATES

Adult rat cerebellum frozen sections were prepared and dried on glass coverslips. 70,000 C6, 3T3, or B16 cells in 100 $\mu l$ were added to each well containing slices previously rinsed with cold DMEM/FCS. Cultures were incubated for 2 days at 37° C. Cultures were then fixed and stained with cresyl violet. Three to four cerebellum slices were used per point per experiment, with each experiment being repeated at least 2 times.

Myelin from rat spinal cord (CNS) or sciatic nerve (PNS) purified on a discontinuous sucrose gradient as described in Section 6.1.5., was dried overnight onto PLYS coated wells (20 $\mu g$ protein/well of 100 $mm^2$ surface). Unbound membranes were removed by three washes with $Ca^{2+}/Mg^{2+}$-free Hank's solution. Myelin coated wells were immediately used in substrate testing assays by the addition of 9,000 cells (C6, 3T3, or B16) per $cm^2$. Alternatively, we used extracted CNS myelin protein, or SDS-PAGE purified 35 and 250 kD inhibitory proteins reconstituted in liposomes (see Section 7.1.5, supra). Experiments were scored at different time points using a phase contrast microscope equipped with a photocamera. Quantifications were done using a surface integration program; three arbitrary fields were photographed for each well at a magnitude of 80×, at least 25 cells per picture were measured. Each point represents the mean of at least 3 wells±SEM. Results are expressed as $\mu^2$ of projected cell surface, or as degree, which was calculated by subtracting from the projected surface value of a spreading cell, the surface value of a completely spheric cell.

9.1.4. C6 PLASMA MEMBRANES AND CONDITIONED MEDIUM PREPARATION

C6 cells grown to 80% confluency were washed twice with Hank's medium, and harvested in 20 ml 8.5% sucrose, 50 mM NaCl, 10 mM Tris buffer, pH 7.4, using a rubber policeman. After mechanical homogenization through a series of needles of decreasing size, a low purity plasma membrane fraction was obtained by centrifugation (5 minutes at 3000× g, 10 minutes at 8000× g, and then 2 hours at 100,000× g). A higher purity fraction was isolated by loading the material on a discontinuous sucrose gradient, containing 50 mM NaCl, 10 mM Tris, pH 7.4 (Quigley, 1976, J. Cell Biol. 71: 472–486). 20–40% sucrose interphase (C6 plasma membranes fraction) and 40–60% sucrose interphase (C6 mitochondrial fraction) were collected, washed in Hank's medium and resuspended in MEM.

Conditioned media were obtained by cultivating 80% confluent C6 cell cultures for 1 day in MEM. The medium was then collected and centrifuged for 10 minutes at 3000× g. In some experiments the conditioned medium was concentrated 10 times using Centricon Tubes.

9.1.5. TREATMENT OF CNS MYELIN WITH C6 PLASMA MEMBRANES

CNS myelin coated PLYS wells were prepared as described in the previous section, but instead of being immediately tested as substrate, they were first incubated with 50 µl of C6 plasma membranes (containing 0.8 mg protein/ml MEM) at 37° for 30 minutes. Dishes were then rinsed twice with Hank's medium and immediately used as substrates for 3T3 cells. In some experiments, protease blockers were added to the membranes using 10 times concentrated solutions.

9.2. RESULTS

9.2.1. C6 GLIOBASTOMAS BUT NOT 3T3 FIBROBLASTS OR B16 MELANOMAS INFILTRATE OPTIC NERVE AND CNS WHITE MATTER IN VITRO

Figure 19A:
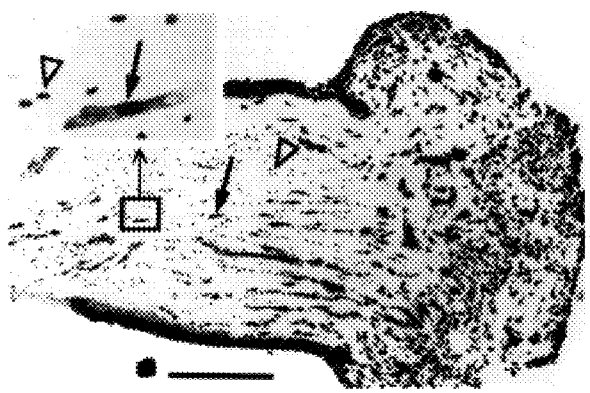
Figure 19B:
Figure 19C:
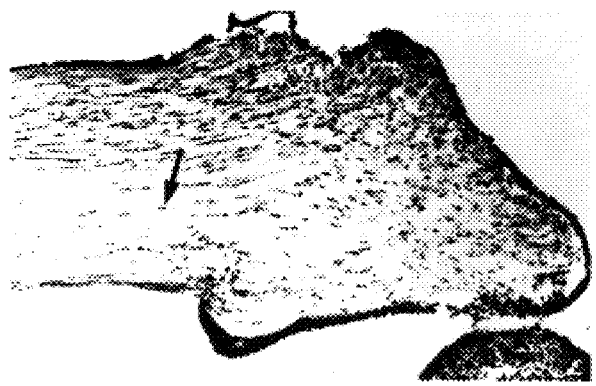
Figure 19D:
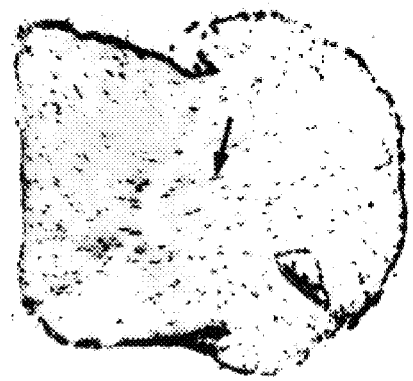

Frozen optic nerve and sciatic nerve explants were placed under a teflon ring and sealed with silicon grease (Schwab and Thoenen, 1985, J. Neurosci. 5:2415–2423). C6 or 3T3 cells were plated into the ring, in contact with one end of the nerve explants. Culture medium was exchanged every other day, and after 5 to 20 days of incubation the nerves were fixed, and sectioned with a cryotome. Infiltrated cells were recognized by cresyl violet staining. PNS explants supported diffuse infiltration of both C6 and 3T3 cells (FIGS. 19C, D). C6 cells were present in the explants at higher density. In the optic nerve explants, a different picture emerged (FIGS. 19A, B); 3T3 cells did not infiltrate the nerves, with the exception of very few cells which migrated along blood vessels (FIG. 19B, arrow). On the other hand, C6 cells infiltrated deep into the optic nerves with a diffuse pattern, reaching a maximum distance of about 3 mm from the entry point in 14 days (migration rate: about 0.2 mm/day).

Figure 20A:
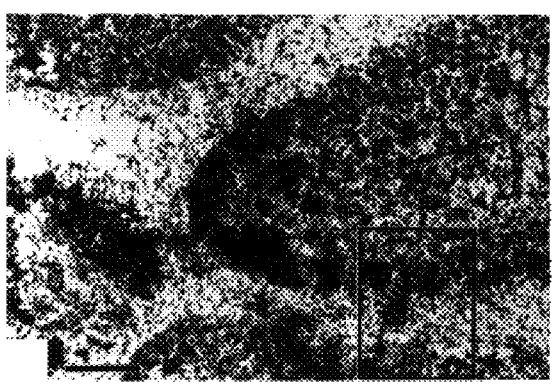
Figure 20B:
Figure 20C:
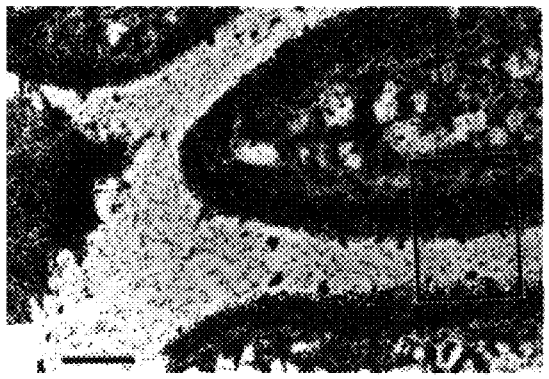
Figure 20D:

As an alternative model, adult rat cerebellum frozen sections were used as a culture substrate for C6, B16 or 3T3 cells. The highly metastatic B16 melanoma cells were found to clearly discriminate between the substrate qualities of the grey and white matter with regard to cell attachment, spreading and migration. In fact, B16 cells exclusively attached and spread on grey matter regions and, even if plated at high cell densities, they did not attach on or migrate into white matter areas of the sections (FIG. 20E). The same picture emerged for 3T3 cells, which formed dense monolayers on grey matter, but not on white matter (FIGS. 20C, D). In contrast to B16 and 3T3 cells, C6 cells were found frequently on white matter as well as on grey matter (FIGS. 20A, B). In some cases we found that C6 cells were more dense on the white matter than on the molecular layer of the grey matter, where they often formed little aggregates which spread with difficulty.

9.2.2. GLIOBLASTOMA CELL SPREADING IS NOT INHIBITED BY CNS MYELIN

The spreading behavior of C6 glioblastomas on CNS myelin adsorbed to PLYS coated wells was compared to that of B16 melanomas and 3T3 fibroblasts. B16 melanoma reaction to a CNS myelin substrate strongly resembled that of 3T3 fibroblasts: 3T3 or B16 cells spreading on CNS myelin was strongly impaired, whereas C6 cell spreading was slightly reduced at the beginning (90 minutes), but no further appreciable differences were detected at later time points (FIGS. 21A–C). The differences between cells on CNS myelin or on PLYS also persisted with prolonged incubation times (up to 1 day).

C6 cells were confronted with the SDS-PAGE purified inhibitors (35 kD and 250 kD) reconstituted in liposomes, and also with living, cultured oligodendrocytes. Again, 35 kD and 250 kD liposomes strongly inhibited 3T3 cell spreading, but they did not impair C6 cell spreading; C6 cells adhered and rapidly assumed the well spread characteristic "fried egg" appearance also on these reconstituted CNS myelin fractions.

9.2.3. SPECIFIC BLOCKERS OF METALLOPROTEASES INHIBIT C6 CELL SPREADING ON CNS MYELIN

The involvement of proteases in C6 behavior was investigated by determining the effect of inhibitors of proteases on C6 cell spreading on either CNS myelin or PLYS. Cys-, Ser- and Asp-protease blockers at the adequate concentrations had no discernible effect on C6 spreading on CNS myelin (Table X).

TABLE X

EFFECT OF DIFFERENT PROTEASE INHIBITORS ON C6 CELL SPREADING ON PLYS OR CNS MYELIN*

| | | | Spreading on: | | |
|---|---|---|---|---|---|
| Protease Class | Protease Inhibitor | | PLYS (% of control on PLYS) | CNS | Inhibition on CNS (%) |
| none, control | | | | 100 | 95 | 5 |
| serine | 6-amino-capronate | 3.0 mM | 93 | 100 | 0 |
| | hirudine | 1.0 nM | nq | nq | 0 |

TABLE X-continued

EFFECT OF DIFFERENT PROTEASE INHIBITORS ON C6
CELL SPREADING ON PLYS OR CNS MYELIN*

| Protease Class | Protease Inhibitor | | | Spreading on: PLYS (% of control on PLYS) | CNS | Inhibition on CNS (%) |
|---|---|---|---|---|---|---|
| | PMSF | 4.0 | mM | 100 | 94 | 6 |
| | trasylol | 200.0 | U/ml | 98 | 93 | 5 |
| cysteine | leupeptine | 0.3 | mM | 91 | 83 | 8 |
| aspartic | pepstatine | 0.3 | mM | 98 | 95 | 3 |
| metallo | 1,10-phenanthroline | 0.3 | mM | 97 | 30 | 67 |
| | bestatine | 0.1 | mM | nq | 104 | 0 |
| | phosphoramidon | 0.3 | mM | nq | 91 | 9 |
| | TIMP | 10.0 | µg/ml | 102 | 93 | 9 |
| | cm-phe-leu | 0.5 | mM | 95 | 92 | 3 |
| | cbz-gly-gly-NH$_2$ | 1.0 | mM | nq | 99 | 1 |
| | cbz-gly-phe-NH$_2$ | 1.0 | mM | 100 | 45 | 55 |
| | cbz-ala-phe | 0.3 | mM | 98 | 90 | 8 |
| | cbz-tyr-tyr | 0.3 | mM | 101 | 56 | 45 |
| general | 2-macroglobulin | 3.0 | µM | 70 | 52 | 18 |
| | cocktail − | | | nq | nq | 0 |
| | cocktail + | | | nq | nq | ++ |

*Cells were plated on PLYS or CNS myelin coated culture dishes.
Spreading was determined after 150 minutes as described supra in Materials and Methods. Inhibition values were calculated by subtracting spreading values on CNS myelin from the values on PLYS.
PMSF: Phenyl methyl sulfonyl fluoride.
TIMP: Tissue inhibitor of metalloproteases.
Cocktail −: trasylol, 200 U/ml; leuptine, 0.3 mM; pepstatine, 0.3 mM.
Cocktail +: same as cocktail −, but with 0.3 mM 1,10-phenantroline.
nq: not quantified, only qualitative The specific metalloprotease blocker 1,10-phenanthroline on the other hand, resulted in a strong inhibition of C6 spreading specifically on CNS myelin: 1,10-phenanthroline inhibited C6 spreading on myelin up to 67% after 2 hours in culture (Table X). None of the blockers tested showed a significant effect on C6 cell spreading on PLYS. 1,10-phenanthroline is a general metalloprotease inhibitor due to its property of metal ion chelation. However, inhibition by this substance is not sufficient to define a proteolytic activity, since other metallodependent enzymes are also inhibited. Many other inhibitors of metalloproteases have been found, but they usually turned out not to be as general as 1,10-phenanthroline. Phosphoramidon (Komiyama, et al., 1975, Biochem. Biophys. Res. Comm. 65:352–357), bestatine (Umezawa, et al., 1976, J. Antibiot. 29:857–859) and the tissue inhibitor of metalloprotease (TIMP; Cawston, et al., 1987, Biochem. J. 195:159–165) did not impair C6 cell spreading (Table X).

TIMP also does not inhibit a brain membrane associated metalloprotease degrading enkephaline. Carboxymethyl-phe-leu (Fournie-Zaluski, M. C. et al., 1983, J. Med. Chem. 26:60–65), a modified peptide with high affinity for enkephalinase (Almenoff, J. and M. Orlowski, 1983, Biochemistry 22:590–599), did not inhibit C6 cell spreading (Table X). On the other hand, we found that the dipeptides cbz-gly-phe-NH$_2$ and cbz-tyr-tyr lead to 55% inhibition of C6 cell spreading on CNS myelin, but not on PLYS, PNS myelin or glass. These peptides are substrate peptides with metalloprotease specificity (Almenoff and Orlowski, supra; Baxter, et al., 1983, Proc. Natl. Acad. Sci. U.S.A. 80:4174–4178; Couch and Strittmatter, 1983, Cell 32:257–265; Chen and Chen, 1987, Cell 48:193–203; Lelkes and Pollard, 1987, J. Biol. Chem. 262:15496–14505).

In order to exclude a possible general enhancement of C6 cell spreading on nonpermissive substrates, we tested metalloprotease-dependent C6 cell spreading on two other substrates in addition to PLYS and CNS myelin (FIG. 22): PNS myelin and glass. PNS myelin was chosen as a control for the general properties of a myelin membrane fraction (e.g., high content of lipids), and glass was chosen because of its well known bad substrate qualities. Half maximal inhibition of spreading on CNS myelin was obtained with 200 µM 1,10-phenanthroline. On PLYS, glass, and PNS myelin (FIG. 22), 1,10-phenanthroline did not impair C6 cell spreading at concentrations up to 0.5 mM (FIG. 22).

Absorption of CNS myelin with a monoclonal antibody (IN-1) raised against CNS myelin inhibitory components (see Section 8.1.3., supra) largely reversed 1,10-phenanthroline dependent inhibition of C6 cell spreading on CNS myelin liposomes (Table XI). IN-1 also almost completely neutralized the inhibitory substrate property of CNS myelin protein liposomes for 3T3 cells (Table XI).

TABLE XI

INHIBITION OF C6 CELL SPREADING BY
1,10-PHENANTHROLINE ON CNS MYELIN
IS NEUTRALIZED BY ANTIBODY IN-1*

| Cells | Antibody | 1,10-Phenan- throline | spreading value on: CNS lipos. | PLYS | % inhibition on CNS lipos. |
|---|---|---|---|---|---|
| 3T3 | — | 0 | 1.11 | 2.00 | 45 |
| 3T3 | IN-1 | 0 | 2.03 | 2.26 | 10 |
| 3T3 | mouse IgM | 0 | 1.16 | 2.18 | 47 |
| C6 | — | 0 | 2.48 | 2.52 | 2 |
| C6 | — | 0.3 mM | 1.35 | 2.49 | 46 |
| C6 | IN-1 | 0 | 2.46 | 2.48 | 1 |
| C6 | IN-1 | 0.3 mM | 2.25 | 2.54 | 11 |
| C6 | mouse IgM | 0 | 2.36 | 2.42 | 2 |
| C6 | mouse IgM | 0.3 mM | 1.41 | 2.39 | 41 |

*CNS myelin protein liposomes were used as substrates, and were preadsorbed with monoclonal antibody IN-1 against the myelin inhibitory substrate constituents (see Section 8.1.4), or with mouse IgM. Spreading was calculated after 150 minutes and is expressed as µm$^2$ 10$^3$.
% Inhibition relates to spreading values on PLYS.

These results indicate that the metalloprotease(s) plays an important role for overcoming of CNS myelin inhibitory substrates by neutralization Of IN-1 inhibitory properties.

9.2.4. A C6 PLASMA MEMBRANE ASSOCIATED ACTIVITY NEUTRALIZES THE INHIBITORY SUBSTRATE PROPERTY OF CNS MYELIN

CNS myelin-coated culture wells were incubated with C6 conditioned medium or C6 plasma membranes, and subsequently tested for their inhibitory substrate property with spreading of 3T3 cells. We found that C6 plasma membranes contained an activity which strongly reduced CNS myelin inhibitory activity (FIGS. 23A–D, Table XII). The same treatment also decreased the inhibitory effect of CNS myelin protein liposomes or SDS-PAGE-purified, reconstituted 35 kD and 250 kD inhibitory components. The decrease in CNS myelin inhibitory activity for 3T3 cell adhesion and spreading was quantitified by measuring spreading values and DNA synthesis (Table XII).

TABLE XII

C6 PLASMA MEMBRANES REDUCE CNS MYELIN
INHIBITORY SUBSTRATE PROPERTY FOR 3T3 CELLS*

| Substrates | 3T3 Cell Spreading (%) | $^3$H-Thymidine Incorporation (%) |
|---|---|---|
| PLYS | 100 | 100 |
| CNS myelin | 15 | 30 |
| CNS myelin, C6 PM | 52 | 83 |
| CNS myelin, C6 PM, phen. treated | 17 | 50 |
| CNS myelin, C6 PM, EDTA treated | 13 | nd |

*3T3 cells were plated on PLYS or CNS myelin. Spreading was assessed after 150 minutes CNS myelin was preincubated with a C6 cell plasma membrane fraction (C6 PM) in the absence or presence of metalloprotease inhibitors as indicated.
$^3$H-thymidine was added when 3T3 cells were plated, and incorporation was determined after 20 hours
nd: not determined.

1,10-phenanthroline, EDTA, and the dipeptide cbz-gly-phe-NH$_2$ completely blocked the C6 plasma membrane effect. Trasylol, leupeptine and pepstatine did not inhibit this effect. C6 conditioned medium used as such, or 10-times concentrated, did not contain any degradative activity able to neturalize CNS myelin inhibitory substrate properties.

9.2.5. INHIBITORS OF METALLOPROTEASES IMPAIR C6 CELL SPREADING ON CNS WHITE MATTER AND C6 INFILTRATION OF CNS EXPLANTS

In order to investigate the relevance of the C6 plasma membrane metalloprotease activity not only for C6 cell attachment and spreading, but also for C6 cell migration and infiltration, C6 cells were plated on cerebellar frozen sections or added to optic nerve explants in the presence of two metalloprotease inhibitors (1,10-phenanthroline and cbz-tyr-tyr). Parallel cultures contained inhibitors for the three other classes of proteases (leupeptine, pepstatine or trasylol), or a control dipeptide (cbz-ala-phe).

The presence of 1,10-phenanthroline at different concentrations (50, 100, 200 and 300 µM), or the dipeptide cbz-tyr-tyr (100 µM) dramatically changed the distribution and behavior of C6 cells on the white matter areas when cerebellar frozen sections were used as culture substrates (FIG. 23). C6 cells also adhered in large numbers and spread extensively on the grey matter (FIGS. 23A–D).

Rat optic nerves were injected with 4 µl of 3 mM solutions of either cbz-ala-phe or cbz-tyr-tyr. Cells were incubated with medium containing 0.5 mM peptide. In the outer chamber, where no cells were present, the peptide concentration was 1 mM. After 14 days, the immigration of C6 cells into the explants differed greatly (FIGS. 24A–B). cbz-ala-phe-injected nerves contained more cells, and C6 cell infiltration was not affected, as compared to explants injected with culture medium only. On the other hand, cbz-tyr-tyr inhibited C6 cell infiltration in all the 8 nerves examined (2 experiments). C6 cells were found mainly at the cut end of these nerve explants, and deep infiltration, which occurred massively in control explants, was strongly reduced by cbz-tyr-tyr.

9.3. DISCUSSION

The present results demonstrate that C6 glioblastoma cells, in contrast to neurons, fibroblasts and B16 melanoma cells, were not impaired in their migration into optic nerve explants or in attachment and spreading on CNS white matter, isolated CNS myelin, or living oligodendrocytes. The fact that the behavior of C6 cells differed characteristically from that of several cell types in all the assay systems studied suggests common underlying cell biological mechanisms, both for C6 spreading on an inhibitory substrate as well as for C6 mobility in an environment (optic nerve) which does not allow fibroblasts, Schwann cell or melanoma cell migration nor does it allow ingrowth of regenerating nerve fibers. This behavior of C6 cells was not due to "insensitivity" to the inhibitory components, since C6 cell motility was drastically inhibited on CNS myelin or white matter in the presence of specific protease blockers, and this effect was reversed by selective neutralization of myelin-associated inhibitory proteins with a monoclonal antibody (IN-1).

Inactivation of myelin-associated inhibitory constituents occurred by living C6 cells as well as by C6 plasma membranes. Our experiments with a number of protease blockers with different known specificities showed that this C6 associated activity belongs to the metalloenzyme family. The close parallelism observed between prevention of C6 cell spreading on CNS myelin and prevention of inactivation of myelin-associated inhibitory proteins strongly suggests that modification of the inhibitory substrate components by a metalloprotease could be the mechanism which enables C6 cells to spread on myelin, on white matter, and to infiltrate optic nerve explants.

Metalloproteases form an increasingly numerous group, the members of which differ in their sensitivity to various blockers. The most general blocker is 1,10 -phenanthroline which impaired C6 cell spreading on CNS myelin up to 67%, whereas most inhibitors of the other classes of proteases had no detectable effects. In the early (90 minutes) but not the later (300 minutes) phases of C6 cell spreading on myelin, an effect of trypsin-like serine-protease inhibitors was also observed. The effect of 1,10-phenanthroline was dose-dependent, with an $IC_{50}$ of 200 µM. This effect was specific for CNS myelin as a substrate, since normal, rapid spreading of C6 cells was observed on other substrates such as CNS grey matter, PNS myelin, glass or PLYS in the presence of 1,10-phenanthroline. Other known metalloprotease blockers like bestatine (inhibitor of aminopeptidases; Umezawa, et al., 1976, J. Antibiot. 29:857–859), phosphoramidone (inhibitor of thermolysin-like metalloproteases; Komiyama, et al., 1975, Biochem. Biophys. Res. Commun. 65:352–357) and TIMP (inhibitor of ECM degrading metalloproteases; Cawston, et al., 1981, 195:159–165) did not lead to inhibition of C6 cell spreading on CNS myelin. Since metalloproteases generally hydrolyze peptide bonds followed by large aliphatic or neutral aromatic amino acids, we tested the effect of dipeptide substrate analogues containing such residues. Cbz-gly-phe-NH$_2$ (1 mM) or cbz-tyr-tyr (0.3 mM) inhibited C6 cell spreading specifically on CNS myelin. Cbz-gly-phe-NH$_2$ was found to inhibit other 1,10-phenanthroline sensitive enzyme activities with relative high specificity (Almenoff and Orlowski, 1983, Biochemistry 22:590–599; Baxter, et al., 1983, Proc. Natl. Acad. Sci. U.S.A. 80:4174–4178; Couch and Strittmatter, 1983, Cell 32:257–265; Chen, J. M. and Chen, W. T., 1987, Cell 48:193–203; Lelkes and Pollard, 1987, J. Biol. Chem. 262:15496–14505).

Inactivity of C6-conditioned medium and cell fractionation experiments demonstrated that the myelin-directed proteolytic actiity is associated with C6 plasma membranes. The isolation and characterization of a plasma membrane-bound metalloprotease (endopeptidase 24.11, enkephalinase), which is also blocked by 1,10- phenanthroline but not by TIMP, was reported by Almenoff and Orlowski (1983, supra). However, the metalloprotease described herein is probably not an enkephalinase, since carboxymethyl-phe-leu, a peptide with high affinity for enkephalinase (Fournie-Zaluski, et al., 1983, J. Med. Chem. 26:60–65), did not affect C6 spreading on myelin. A metalloprotease expressed by Rous sarcoma virus transformed chick embryo fibroblasts and localized at adhesion sites and on "invadopodia" was described by Chen, and Chen, 1987, supra. This enzyme is also inhibited by 1,10-phenanthroline and cbz-gly-phe-$NH_2$, but not by phosphoramidon, as is the metalloprotease described here. However, unlike the enzyme of Chen and Chen, we could not detect any fibronectin degradative activity on C6 cells.

The highly metastatic B16 mouse melanoma cells were tested in all the assays used with C6 cells. Interestingly, B16 cells did not migrate into optic nerve explants, but responded to the myelin-associated inhibitors in a way very similar to 3T3 cells or neurons. In line with this in vitro behavior, B16 cells, upon intraventricular injection, form mainly meningiomas or intraventricular tumors without significant infiltration of the brain parenchyma. Thus. the mechanisms providing metastatic behavior to B16 cells in the periphery are different from those conferring high mobility to C6 cells in the CNS tissue.

Inhibition of C6-associated metalloprotease not only inhibited C6 spreading on CNS myelin, but also abolished C6 cell attachment, spreading, and migration on CNS white matter, and the dipeptide, cbz-tyr-tyr strongly impaired the migration of C6 cells into optic nerve explants. This metalloprotease activity(ies) may, therefore, be crucially involved in the infiltrative behavior of C6 glioblastoma cells in CNS tissue, also in vivo.

10. LONG DISTANCE TRACT REGENERATION IN THE LESIONED SPINAL CORD OF RATS BY A MONOCLONAL ANTIBODY AGAINST MYELIN-ASSOCIATED NEURITE GROWTH INHIBITORS

The monoclonal antibody IN-1, which neutralizes the inhibitory substrate effect of the 35 kD and 250 kD myelin-associated proteins and of CNS tissue explants (Caroni and Schwab, 1988, Neuron 1:85–96), was applied to young rats intracerebrally by implanting antibody producing tumors into the neocortex. Complete transections of the cortico-spinal component of the pyramidal tract (CST) at 2–4 weeks of age was followed by massive sprouting around the lesion, and, in IN-1 treated rats, by elongation of fine axons and fascicles up to 8–11 mm distal to the lesion within 2 weeks. In control rats the maximal distance of observed elongation rarely exceeded 1 mm. These results demonstrate the induced regeneration capacity of a major motor CNS tract within differentiated CNS tissue, and point to the clinical importance of CNS neurite growth inhibitors and their antagonists.

10.1. MATERIALS AND METHODS

10.1.1. PRE-OPERATIVE PREPARATION OF ANIMALS INCLUDING IMPLANTATION OF HYBRIDOMA CELLS

Young Lewis rats (P2–11) were injected unilaterally under ether anesthesia into the dorsal frontal cortex with 1 Mio. hybridoma cells in 1 or 2 µl. Control rats were injected with the same number of cells of a hybridoma line producing antibodies against horseradish peroxidase (HRP). Non-injected controls were also used. Hybridoma cells: IN-1 secreting cells were obtained by fusion of P3U myeloma cells with spleen cells of a BALB/c mouse immunized against the PAGE-purified 250 kD inhibitory protein fraction from rat spinal cord myelin as described by Caroni and Schwab (1988, Neuron 1:85–96); anti-HRP secreting cells were obtained by Dr. P. Streit, Zurich, according to the protocol of Semenenko et al. (1985 Histochem. 83:405–408) using the same myeloma line (P3U) as for IN-1. In all hybridoma-injected rats, tumors formed within a few days as solid, well delineated tumors often spanning the entire thickness of the neocortex and contacting the lateral ventricle (FIGS. 26A–B). Cyclosporin A injections (15 µg/g body weight, 2 injections at 3 day intervals) helped to prevent tumor resorption which otherwise occurred after 2–3 weeks. Massive production of antibodies could be detected by staining brain sections with anti-mouse Ig-FITC (FITC-conjugated immunoglobulin) (FIG. 26B), and by the presence of In-1 antibodies in the serum (data not shown).

10.1.2. PROCEDURE FOR PERFORMING SPINAL CORD LESION

Spinal cord lesions were placed at 2–4 weeks of age (Table III, infra) at the thoracic level $T_{5-7}$ by slightly separating two vertebrae and transecting the dorsal two thirds of the spinal cord with iridectomy scissors. The lesion completely transsected the CSTs of both sides including the lateral projections into the dorsal gray matter, and also the central canal. Ventral and lateral white matter remained undisturbed, allowing the rats a seemingly normal behavior. Lesions were done at 15–29 days of age, i.e. 5–20 days after termination of axon growth in the CST (Table XIII). A U-shaped stainless steel wire was then implanted into the lesion site in order to assure complete transection of both CSTs and to mark the lesion site. (The wire was removed prior to embedding the fixed spinal cords for sectioning).

TABLE XIII

REGENERATION OF CORTICO-SPINAL TRACT
AXONS AFTER MID-THORACIC LESIONS IN
CONTROL AND ANTIBODY IN-1 TREATED RATS

| Tumor-type | Day of lesion | Survival time | Max. distance of regenerated CST axons caudal to lesion |
|---|---|---|---|
| none | P 14 | 19 d. | 0.1 |
|  |  |  | 0.2 |
|  |  |  | 0.2 |
|  |  |  | 0.5 |
| none | P 22 | 14 d. | 0.4 |
|  |  |  | 0.2 |
| none | P 22 | 11 d. | 0.7 |
|  |  |  | 0.6 |
| αHRP | P 15 | 14 d. | 0.4 |
|  |  |  | 1.0 |
|  |  |  | 1.8 |
|  |  |  | 2.6 |
| αHRP | P 18 | 16 d. | 0.1 |
|  |  |  | 0.2 |
|  |  |  | 0.2 |
|  |  |  | 0.3 |
|  |  |  | 0.4 |
|  |  |  | 0.5 |
|  |  |  | 0.8 |
| IN-1 | P 14 | 16 d. | 2 |
|  |  |  | >8* |
|  |  |  | 11 |
| IN-1 | P 15 | 15 d. | 4 |
|  |  |  | 4.5 |
|  |  |  | >5* |
|  |  |  | >5 |

TABLE XIII-continued

REGENERATION OF CORTICO-SPINAL TRACT
AXONS AFTER MID-THORACIC LESIONS IN
CONTROL AND ANTIBODY IN-1 TREATED RATS

| Tumor-type | Day of lesion | Survival time | Max. distance of regenerated CST axons caudal to lesion |
|---|---|---|---|
|  |  |  | >5 |
| IN-1 | P 18 | 18 d. | 2.5 |
| IN-1 | P 19 | 14 d. | 7.7 |
|  |  |  | 7.8 |
| IN-1 | P 28 | 14 d. | >4 |
|  |  |  | >4 |
| IN-1 | P 29 | 27 d. | >2.5 |

Methods as described in FIG. 27. Only rats with regenerative CST sprouts caudal to the lesion were included in this analysis. Distances of regenerating fibers are measured from the caudal edge of the lesion caverns.
*Minimal distance as regenerating fibers reach the caudal end of the tissue block.

10.1.3. POST-LESION EVALUATION

After survival times of 14–28 days (Table XIII), the frontal and parietal cortex contralateral to the tumor was injected with a 5% solution of WGA-HRP (1 μl). Twenty-four hours later, rats were perfused through the heart with 1.25% glutaraldehyde and 1% formaldehyde in 0.1 M phosphate buffer for 10 minutes. The dissected spinal cords (10–15 mm) were postfixed in the same fixative for 1 hour, extensively washed, and embedded for cryostat sectioning. Complete longitudinal section series were mounted on gelatin-coated slides, and reacted for HRP using TMB as a substrate (Mesulam, 1978, J. Histochem. & Cytochem. 26:106–117). Sections were viewed under dark-field illumination in polarized light. Only rats with complete bilateral CST lesions and with sprouts appearing on the caudal side of the lesion were evaluated.

10.2. RESULTS: REGENERATION OF CORTICOSPINAL TRACT (CST) FIBERS OVER LONG DISTANCES IN RATS BEARING IN-1 SECRETING TUMORS

Two weeks after the lesions, at or beyond 1 month of age, the CST was labeled by anterograde transport of WGA-HRP from the frontal and parietal cortex. The histological examination of the lesion site in transverse and longitudinal sections showed a very similar picture in all animals: usually several small caverns were present and communicated with the central canal, a feature which probably greatly enhanced the local access and penetration of the antibodies carried down by the cerebrospinal fluid. The tissue was locally altered, but no dense glial scars were present. Labeled CST fibers approached the lesion as a dense and compact bundle from which massive sprouting occurred 0.5–1 mm proximal to the lesion. In most animals, controls or IN-1-injected, fiber plexus and bundles were seen in and across the lesion area, most often circumventing the lesion caverns ventrally or laterally, but rarely also growing through tissue bridges that had reformed in the wire tract. Fibers leaving the lesion site and travelling in a caudal direction could frequently be observed. In animals without tumors and in rats with anti-HRP-producing tumors, the travelling distances measured on longitudinal sections from the distal edge of the lesion were in most instances below 1 mm (Table XIII, FIGS. 27,28A–G). Even relatively thick fascicles seemed to end abruptly. Very much in contrast, animals bearing IN-1 secreting tumors consistently showed labelled fascicles and fibers at much longer distances caudal to the lesion (FIGS. 27,28A–G). 2.5–5 mm were measured in most animals, 8 and 11 mm were seen in 2 rats (Table XIII). Anatomically, these long distance regenerating CST fibers were most often found close to or in the original CST location, with some fibers also in the gray matter and a few fibers in more dorsal regions corresponding to the sensory tracts.

10.3. DISCUSSION

In the rat, the CST is known to grow down the spinal cord during the first 10 postnatal days, the last axons being added at P9–P10 (Joosten et al., 1987, Dev. Brain Res. 36:121–139; Schreyer and Jones, 1988 Dev. Brain Res. 38:103–119). Lesions of the tract up to P4–P5 lead to a circumvention of the lesion site and to long-distance, often ectopic growth of CST fibers (Schreyer and Jones, 1983, Neurosci. 9:31–40; Bernstein and Stelzner, 1983, J. Comp. Neurol. 221:382–400). No regeneration in the CST has been seen after P6. A very similar lesion response has been observed in hamster and cat (Kalil and Reh, 1982, J. Comp. Neurol. 211:265–275; Tolbert and Der, 1987, J. Comp. Neurol. 260:299–311). For the cat it was demonstrated that these fibers are mostly late-arriving, newly-growing, rather than regenerating axons (Tolbert and Der, 1987, J. Comp. Neurol. 211:265–275). The present results demonstrate that at least a small proportion of CST neurites at 2–3 weeks of age can be induced to regenerate and elongate over long distances inside the spinal cord. The maximal speed of elongation is in the range of 0.5–1 mm/day.

Differentiated CNS tissue of mammals is a nonpermissive substrate for neurite growth beyond a sprouting distance of between 0.2–1 mm (Cajal, 1959, in "Degeneration and Regeneration of the Nervous System," ed. Hafner, New York, p. 1928; David, 1981, Science 214:931–933; and Vidal-Sanz et al., 1987, J. Neurosci. 7:2894–2909). This property is expressed (far more by CNS white matter than CNS gray matter, as shown by culture experiments and by transplantation studies (Schwab and Thoenen, 1985, J. Neurosci. 5:2415–2423; Carbonetto et al., 1987, J. Neurosci. 7:610–620; Savio and Schwab, 1989, in press). Transplantations of fetal adrenergic or serotoninergic neurons of defined fetal ages into adult spinal cords or hippocampus represent up to now the only other experiments where elongation of axons in adult CNS tissue was observed at an anatomical level (Nornes et al., 1983 Cell Tissues Res. 230:15–35; Foster et al., 1985 Exp. Brain Res. 60:427–444 and Bjorklund et al., 1979 Brain Res. 170:409–426). These elongating axons were almost exclusively localized to gray matter areas.

Two oligodendrocyte- and myelin-associated membrane proteins, NI-35 (35 kD) and NI-250 (250 kD), with potent inhibitory effects on neurite growth, were identified by in vitro and biochemical studies (Schwab and Caroni, 1988 J. Neurosci. 8:2381–2393; Caroni and Schwab, 1988, J. Cell. Biol. 106:1281–1288). Monoclonal antibody IN-1, which neutralizes the activity of these constituents in various in vitro systems including adult rat optic nerve explants (Caroni and Schwab, 1988, Neuron 1:85–96), is shown here to lead to true regeneration of cortico-spinal axons in young rats over distances of up to 5–11 mm distal to a spinal cord lesion within 2 weeks. The continuous supply of high levels of antibodies via the cerebrospinal fluid by an antibody-secreting tumor in the cortex, and the local conditions of the lesion probably helped the penetration of the antibodies into the tissue. The absence of axon elongation distal to the lesion in spite of massive sprouting around the lesion site in animals bearing control antibody tumors confirms the specificity of the effect observed. These results clearly demonstrate the ability of antibodies directed toward the myelin-associated neurite growth inhibitor protein to induce neuron fiber regeneration over long distances, as well as the crucial role of the myelin-associated neurite growth inhibitors for the absence of regeneration of lesioned CNS fiber tracts observed under normal conditions.

11. DEPOSIT OF MICROORGANISMS

The following hybridomas, producing the indicated monoclonal antibodies, have been deposited Oct. 28, 1998 with the European Collection of Animal Cell Cultures (ECACC), PHLS Centre for Applied Microbiology and Research, Porton Down, Salisbury, Wiltshire, United Kingdom, and have been assigned the listed accession numbers.

| Hybridoma | Antibody | Accession Number |
|---|---|---|
| Cell line IN-1 | IN-1 | 88102801 |
| Cell line IN-2 | IN-2 | 88102802 |

The present invention is not be limited in scope by the cell lines deposited or the embodiments disclosed in the examples which are intended as illiustrations of a few aspects of the invention and any embodiment which are functionally equivalent are within the scope of this invention. Indeed, various modifications of the invention in addition to those shown and described herein will become apparent to those skilled in the art and are intended to fall within the scope of the appended claims.

What is claimed is:

1. A method for treating a patient with a malignant tumor that originates in the central nervous system comprising administering a therapeutically effective amount of a metalloprotease inhibitor to the patient.

2. The method according to claim 1 in which the malignant tumor is a glioblastoma.

3. The method according to claim 1 in which the metalloprotease inhibitor is selected from the group consisting of 1,10 phenanthroline, ethylenediamine tetraacetate, ethyleneglycol-bis (β-aminoethyl ether) N, N, N'-N'-tetraacetate, carbobenzoxy-tyrosine-tyrosine, carbobenzoxy-glycine-phenylalanine-amide, carbobenzoxy-phenylalanine-tyrosine-amide, carbobenzoxy-phenylalanine-phenylalanine-amide, and carbobenzoxy-glycine-phenylalanine-phenylalanine-amide.

4. The method according to claim 1 in which the patient is a human.

5. A method for treating a patient with a malignant tumor that originates in the central nervous system comprising administering a therapeutically effective amount to the patient of a compound which inhibits the metalloprotease activity of a neurite growth regulatory factor, said factor consisting of a molecule isolated from glioblastoma cells and characterized by the following properties:

(a) metalloprotease activity; and (b) neutralizes the nonpermissive substrate property of the CNS myelin of a higher vertebrate, in which the neutralization is detected by observing the ability of the CNS myelin in the presence of the factor to support neurite outgrowth or fibroblast spreading in vitro.

6. The method according to claim 5 in which the compound inhibits C6 cell spreading and migration on CNS myelin of a higher vertebrate wherein the inhibition can be reversed by a substance which neutralizes the nonpermissive substrate property of the CNS myelin of a higher vertebrate.

7. The method according to claim 6 in which the inhibition of C6 cell spreading and migration by the compound can be reversed by monoclonal antibody IN-1, as produced by cell line IN-1, as deposited with the ECACC and assigned accession number 88102801.

8. The method according to claim 5 in which the tumor is a glioblastoma.

9. The method according to claim 5 in which the compound is selected from the group consisting of 1,10-phenanthroline, ethylenediamine tetraacetate, ethyleneglycol-bis (β-aminoethyl ether) N, N, N'-N'-tetraacetate, carbobenzoxy-tyrosine-tyrosine, carbobenzoxy-glycine-phenylalanine-amide, and carbobenzoxy-phenylalanine-tyrosine-amide, carbobenzoxy-phenylalanine-phenylalanine-amide, and carbobenzoxy-glycine-phenylalanine-phenylalanine-amide.

10. The method according to claim 5 in which the patient is a human.

* * * * *